(12) United States Patent
Townsend et al.

(10) Patent No.: US 11,236,391 B2
(45) Date of Patent: Feb. 1, 2022

(54) GENE EXPRESSION MARKERS AND TREATMENT OF MULTIPLE SCLEROSIS

(71) Applicant: Genentech, Inc., South San Francisco, CA (US)

(72) Inventors: Michael Townsend, San Jose, CA (US); Alvernia Francesca Setiadi, San Carlos, CA (US); Tracy Staton, Stanford, CA (US)

(73) Assignee: Genentech, Inc., South San Francisco, CA (US)

( * ) Notice: Subject to any disclaimer, the term of this patent is extended or adjusted under 35 U.S.C. 154(b) by 13 days.

(21) Appl. No.: 15/662,079

(22) Filed: Jul. 27, 2017

(65) Prior Publication Data
US 2018/0080080 A1   Mar. 22, 2018

Related U.S. Application Data

(63) Continuation of application No. PCT/US2016/015344, filed on Jan. 28, 2016.

(60) Provisional application No. 62/108,914, filed on Jan. 28, 2015.

(51) Int. Cl.
| | |
|---|---|
| *A61K 39/395* | (2006.01) |
| *C07K 16/24* | (2006.01) |
| *C07K 16/28* | (2006.01) |
| *C12Q 1/6883* | (2018.01) |
| *G01N 33/564* | (2006.01) |
| *A61K 39/00* | (2006.01) |

(52) U.S. Cl.
CPC ........ *C12Q 1/6883* (2013.01); *A61K 39/3955* (2013.01); *C07K 16/244* (2013.01); *C07K 16/2866* (2013.01); *G01N 33/564* (2013.01); *A61K 2039/505* (2013.01); *C07K 2317/76* (2013.01); *C12Q 2600/106* (2013.01); *C12Q 2600/118* (2013.01); *C12Q 2600/158* (2013.01); *G01N 2333/47* (2013.01); *G01N 2333/522* (2013.01); *G01N 2333/535* (2013.01); *G01N 2333/5412* (2013.01); *G01N 2333/5421* (2013.01); *G01N 2333/8146* (2013.01); *G01N 2800/285* (2013.01); *G01N 2800/50* (2013.01); *G01N 2800/52* (2013.01)

(58) Field of Classification Search
CPC ............ C12Q 1/6883; C12Q 2600/158; A61K 39/3955; G01N 33/564; G01N 2800/285
See application file for complete search history.

(56) References Cited

U.S. PATENT DOCUMENTS

| | | |
|---|---|---|
| 3,773,919 A | 11/1973 | Boswell et al. |
| 4,275,149 A | 6/1981 | Litman et al. |
| 4,318,980 A | 3/1982 | Boguslaski et al. |
| 4,376,110 A | 3/1983 | David et al. |
| 4,485,045 A | 11/1984 | Regen |
| 4,544,545 A | 10/1985 | Ryan et al. |
| 4,676,980 A | 6/1987 | Segal et al. |
| 4,737,456 A | 4/1988 | Weng et al. |
| 4,816,567 A | 3/1989 | Cabilly et al. |
| 5,013,556 A | 5/1991 | Woodie et al. |
| 5,116,964 A | 5/1992 | Capon et al. |
| 5,229,275 A | 7/1993 | Goroff |
| 5,500,362 A | 3/1996 | Robinson et al. |
| 5,527,307 A | 6/1996 | Srisathapat et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,186 A | 10/1996 | Peter et al. |
| 5,569,825 A | 10/1996 | Lonberg et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,637,095 A | 6/1997 | Nason et al. |
| 5,641,870 A | 6/1997 | Rinderknecht et al. |
| 5,661,016 A | 8/1997 | Lonberg et al. |
| 5,821,337 A | 10/1998 | Carter et al. |
| 6,194,551 B1 | 2/2001 | Idusogie et al. |
| 6,242,195 B1 | 6/2001 | Idusogie et al. |
| 6,283,761 B1 | 9/2001 | Joao |
| 6,528,624 B1 | 3/2003 | Idusogie et al. |
| 6,538,124 B1 | 3/2003 | Idusogie et al. |
| 6,602,684 B1 | 8/2003 | Umaña et al. |
| 7,807,155 B2 | 10/2010 | Di Padova et al. |
| 7,833,527 B2 | 11/2010 | Tocker et al. |
| 7,838,638 B2 | 11/2010 | Allan et al. |
| 8,519,107 B2 | 8/2013 | Almagro et al. |

(Continued)

FOREIGN PATENT DOCUMENTS

| | | |
|---|---|---|
| EP | 0 404 097 A2 | 12/1990 |
| WO | WO 91/00360 A1 | 1/1991 |

(Continued)

OTHER PUBLICATIONS

Mohsenin et al., FASEB J., 2007, vol. 21:1026-1036.*

(Continued)

*Primary Examiner* — Xiaozhen Xie

(74) *Attorney, Agent, or Firm* — Baker Botts L.L.P.

(57) ABSTRACT

The present invention concerns markers of multiple sclerosis, their use, and treatment with IL-17 antagonists, including IL-17 antibodies, of subjects with increased levels of such markers.

18 Claims, 28 Drawing Sheets

Specification includes a Sequence Listing.

(56) References Cited

U.S. PATENT DOCUMENTS

| | | | |
|---|---|---|---|
| 8,580,265 | B2 | 11/2013 | Adams et al. |
| 8,715,669 | B2 | 5/2014 | Masternak et al. |
| 2002/0004587 | A1 | 1/2002 | Miller et al. |
| 2002/0177188 | A1 | 11/2002 | Chen et al. |
| 2003/0157108 | A1 | 8/2003 | Presta |
| 2004/0093621 | A1 | 5/2004 | Shitara et al. |
| 2005/0014934 | A1 | 1/2005 | Hinton et al. |
| 2005/0266467 | A1 | 12/2005 | Sushmita |
| 2008/0183395 | A1 | 7/2008 | Bevilacqua et al. |
| 2010/0266609 | A1* | 10/2010 | Adams .............. C07K 16/244 424/158.1 |
| 2011/0136113 | A1 | 6/2011 | Hitoshi et al. |
| 2011/0177578 | A1 | 7/2011 | Yoshikazu |
| 2014/0193827 | A1 | 7/2014 | Schwartz |
| 2014/0314743 | A1 | 10/2014 | Rommelaere et al. |

FOREIGN PATENT DOCUMENTS

| | | |
|---|---|---|
| WO | WO 1991/10741 A1 | 7/1991 |
| WO | WO 92/203 73 A1 | 11/1992 |
| WO | WO 93/08829 A1 | 5/1993 |
| WO | WO 93/11161 A1 | 6/1993 |
| WO | WO 93/16185 A2 | 8/1993 |
| WO | WO 94/04690 A1 | 3/1994 |
| WO | WO 96/27011 A1 | 9/1996 |
| WO | WO 1996/3 3 73 5 A1 | 10/1996 |
| WO | WO 1996/34096 A1 | 10/1996 |
| WO | WO 1997/17852 A1 | 3/1997 |
| WO | WO 97/30087 A1 | 8/1997 |
| WO | WO 97/38731 A1 | 10/1997 |
| WO | WO 1998/24893 A2 | 6/1998 |
| WO | WO 98/58964 A1 | 12/1998 |
| WO | WO 99/22764 A1 | 5/1999 |
| WO | WO 99/51642 A1 | 10/1999 |
| WO | WO 00/42072 A2 | 7/2000 |
| WO | WO 01/46420 A2 | 6/2001 |
| WO | WO 03/011878 A2 | 2/2003 |
| WO | WO 2010/005387 A1 | 1/2010 |
| WO | WO 2011/053763 A2 | 5/2011 |

OTHER PUBLICATIONS

Leon et al., Mayo Clin. Proc., 2004, vol. 79(7):945-956.*
Nunemaker et al., J. Endocrinol., 2014, vol. 222(2):267-276.*
Lee et al., Brain, 1999, vol. 122(Pt. 2):191-197.*
Haas, M.J., SciBX, 2013, vol. 6(31):1-2.*
Karabudak et al., J. Neurol., 2004, vol. 251:279-283.*
Kurtuncu et al., Cytokine, 2012, vol. 59(2):400-402.*
Kostic et al., Scand. J. Immunol., 2014, vol. 79(3):181-186.*
Anderson, Medscape—Oct. 17, 2012.*
"Current Protocols in Molecular Biology" (F.M. Ausubel et al., eds., (1987), Table of Contents.
"PCR: The Polymerase Chain Reaction," (Mullis et al., eds., 1994), Table of Contents.
Acar et al., "Serum MMP-2, MMP-9, TIMP-1 and TIMP-2 levels in multiple sclerosis clinical subtypes and their diagnostic value in the progressive disease course," Biomedical Research 25(3):343-350 (2014).
Adamson et al., "Tissue Inhibitor of Metalloproteinase 1 Is Preferentially Expressed in Th1 and Th17 T-Helper Cell Subsets and Is a Direct Stat Target Gene," PLoS ONE 8(3):e59367 (2013).
Aggarwal et al., "IL-17: prototype member of an emerging cytokine family," J Leukoc Biol. 71:1-8 (2002).
Aggarwal et al., "Interleukin-23 Promotes a Distinct CD4 T Cell Activation State Characterized by the Production of Interleukin-17," J. Biol. Chem., 278(3):1910-1914 (2003).
Ausubel et al., "Characteristics of Amino Acids" Appendix 1C, Current Protocols in Molecular Biology, vol. 5, John Wiley and Sons (1997).
Barbas III et al., "In vitro evolution of a neutralizing human antibody to human immunodeficiency virus type 1 to enhance affinity and broaden strain cross-reactivity," PNAS USA 91:3809-3813 (1994).

Brennan et al., "Preparation of Bispecific Antibodies by Chemical Recombination of Monoclonal Immunoglobulin G1 Fragments," Science 229:81-83 (1985).
Brodeur et al., "Mouse-Human Myeloma Partners for the Production of Heterohybridomas," Monoclonal Antibody Production Techniques and Applications, pp. 51-63 (Marcel Dekker, Inc., New York, 1987).
Bruggemann et al., "Designer Mice: The Production of Human Antibody Repertoires in Transgenic Animals," Year Immuno., 7:33-40 (1993).
Cai et al., "Regulation of granulocyte colony-stimulating factor gene expression by interleukin-17," Immunol. Lett, 62:51-58 (1998).
Capel et al., "Heterogeneity of Human IgG Fc Receptors," Immunomethods 4:25-34 (1994).
Caron et al., "Engineered Humanized Dimeric Forms of IgG are More Effective Antibodies," J. Exp. Med. 176:1191-1195 (1992).
Carter et al., "High Level Escherichia Coli Expression and Production of a Bivalent Humanized Antibody Fragment," Bio/Technology 10:163-167 (1992).
Carter et al., "Humanization of an anti-p185HER2 antibody for human cancer therapy," PNAS USA, 89:4285-4289 (1992).
Chabaud et al., "Enhancing Effect of IL-17 on IL-1-Induced IL-6 and Leukemia Inhibitory Factor Production by Rheumatoid Arthritis Synoviocytes and Its Regulation by Th2 Cytokines," J. Immunol. 161:409-414 (1998).
Chothia et al., "Canonical Structures for the Hypervariable Regions of Immunoglobulins," J. Mol. Biol. 196:901-917 (1987).
Clackson et al., "Making antibody fragments using phage display libraries," Nature 352:624-628 (1991).
Clynes et al., "Fc receptors are required in passive and active immunity to melanoma," PNAS (USA) 95:652-656 (1998).
Cunningham et al., "High-Resolution Epitope Mapping of hGH-Receptor Interactions by Alanine-Scanning Mutagenesis," Science 244:1081-1085 (1989).
Daeron, "Fc Receptor Biology," Annu. Rev. Immunol. 15:203-234 (1997).
De Haas et al., "Fcγ receptors of phagocytes," J Lab Clin Med 126(4):330-341 (1995).
Eppstein et al., "Biological activity of liposome-encapsulated murine interferon γ is mediated by a cell membrane receptor," PNAS USA 82:3688-3692 (1985).
Fellouse et al., "Synthetic antibodies from a four-amino-acid code: A dominant role for tyrosine in antigen recognition," PNAS USA 101(34):12467-12472 (2004).
Fishwild et al., "High-avidity human IgGκ monoclonal antibodies from a novel strain of miniloocus transgenic mice," Nature Biotechnology 14:845-851 (1996).
Fossiez et al., "T Cell Interleukin-17 Induces Stromal Cells to Produce Proinflammatory and Hematopoietic Cytokines," J. Exp. Med., 183:2593-2603 (1996).
Gazzano-Santoro et al., "A non-radioactive complement-dependent cytotoxicity assay for anti-CD20 monoclonal antibody," J. Immunol. Methods 202:163-171 (1997).
Goding, "Production of Monoclonal Antibodies," Chapter 3 in Monoclonal Antibodies: Principles and Practice, pp. 56-103 (Academic Press, 1983).
Griffiths et al., "Human anti-self antibodies with high specificity from phage display libraries," The EMBO Journal 12(2):725-734 (1993).
Gruber et al., "Efficient Tumor Cell Lysis Mediated by a Bispecific Single Chain Antibody Expressed in Escherichia coli," J. Immunol. 152:5368 (1994).
Guyer et al., "Immunoglobulin Binding by Mouse Intestinal Epithelial Cell Receptors," J. Immunol. 117(2):587-593 (1976).
Hammerling et al., "Production of Antibody-Producing Hybridomas in the Rodent Systems," in Monoclonal Antibodies and T-Cell Hybridomas. pp. 563-681, (Elsevier, N.Y., 1981).
Harlow et al., Antibodies: A Laboratory Manual, (Cold Spring Harbor Laboratory Press, 2nd ed. 1988) Table of Contents.
Hawkins et al., "Selection of Phage Antibodies by Binding Affinity. Mimicking Affinity Maturation," J. Mol. Biol. 226:889-896 (1992).
Heid et al., "Real Time Quantitative PCR," Genome Research 6:986-994 (1996).

(56) References Cited

OTHER PUBLICATIONS

Hollinger et al., "'Diabodies': Small bivalent and bispecific antibody fragments," PNAS USA 90:6444-6448 (1993).
Hwang et al., "Hepatic uptake and degradation of unilamellar sphingomyelin/cholesterol liposomes: A kinetic study," PNAS USA 77(7):4030-4034 (1980).
Hymowitz et al., "IL-17s adopt a cystine knot fold: structure and activity of a novel cytokine, IL-17F, and implications for receptor binding," The EMBO Journal 20(19):5332-5341 (2001).
International Search Report dated Sep. 22, 2016 in International Application No. PCT/US2016/015344.
Isaac et al., "Multiple sclerosis: A serial study using MRI in relapsing patients," Neurology 38:1511-1515 (1988).
Jackson et al., "In Vitro Antibody Maturation," J. Immunol. 154:3310-3319 (1995).
Jakobovits et al., "Analysis of homozygous mutant chimeric mice: Deletion of the immunoglobulin heavy-chain joining region blocks B-cell development and antibody production," PNAS USA, 90:2551-2555 (1993).
Jakobovits et al., "Germ-line transmission and expression of a human-derived yeast artificial chromosome," Nature 362:255-258 (1993).
Johnson et al., "Human antibody engineering," Current Opinion in Structural Biology 3:564-571 (1993).
Jones et al., "Replacing the complementarity-determining regions in a human antibody with those from a mouse," Nature 321:522-525 (1986).
Jovanovic et al., "IL-17 Stimulates the Production and Expression of Proinflammatory Cytokines, IL-β and TNF-α, by Human Macrophages," J. Immunol., 160:3513-3521 (1998).
Kabat et al., Sequences of Proteins of Immunological Interest, 5th Ed. Public Health Service, National Institutes of Health, Bethesda, MD. (1991), Table of Contents.
Kennedy et al., "Mouse IL-17: A Cytokine Preferentially Expressed by αβTCR+CD4-CD8-T Cells," J. Interferon Cytokine Res., 16:611-617 (1996).
Kohler et al., "Continuous cultures of fused cells secreting antibody of predefined specificity," Nature 256:495-497 (1975).
Kostelny et al., "Formation of a Bispecific Antibody by the Use of Leucine Zippers," J. Immunol., 148(5):1547-1553 (1992).
Kozbor et al., "A Human Hybrid Myeloma for Production of Human Monoclonal Antibodies," J. Immunol., 133(6):3001-3005 (1984).
Kuestner et al., "Identification of the IL-17 Receptor Related Molecule IL-17RC as the Receptor for IL-17F," J. Immunol. 179:5462-5473 (2007).
Kurasawa et al., "Increased Interleukin-17 Production in Patients with Systemic Sclerosis," Arthritis Rheu 43(11):2455-2463 (2000).
Laan et al., "Neutrophil Recruitment by Human IL-17 Via C-X-C Chemokine Release in the Airways," J. Immunol., 162:2347-2352 (1999).
Lee et al., "Bivalent antibody phage display mimics natural immunoglobulin," J. Immunol. Methods 284:119-132 (2004).
Lee et al., "High-affinity Human Antibodies from Phage-displayed Synthetic Fab Libraries with a Single Framework Scaffold," J. Mol. Biol. 340:1073-1093 (2004).
Lee et al., "Serum gelatinase B, TIMP-1 and TIMP-2 levels in multiple sclerosis: A longitudinal clinical and MRI study," Brain 122(2):191-197 (1999).
Lehninger, Chapter 4, The Amino Acid Building Blocks of Proteins in Biochemistry, 2nd ed., pp. 73-75, Worth Publishers, Inc. New York (1975).
Linden et al., "Airway neutrophils and interleukin-17," Eur Respir J. 15:973-977 (2000).
Liu et al., "Crystal structures of interleukin 17A and its complex with IL-17 receptor A," Nature Communications 4:1888 (2013).
Lonberg et al., "Antigen-specific human antibodies from mice comprising four distinct genetic modifications," Nature 368:856-859 (1994).
Lonberg et al., "Human Antibodies from Transgenic Mice," Intern. Rev. Immunol., 13:65-93 (1995).

Lublin et al., "Defining the clinical course of multiple sclerosis," Neurology 83:278-286 (2014).
Marks et al., "By-passing Immunization. Human Antibodies from V-gene Libraries Displayed on Phage," J. Mol. Biol. 222:581-597 (1991).
Marks et al., "By-Passing Immunization: Building High Affinity Human Antibodies by Chain Shuffling," Bio/Technology 10:779-783 (1992).
Martin et al., "Irreversible Coupling of Immunoglobulin Fragments to Preformed Vesicles," J. Biol. Chem., 257:286-288 (1982).
Matusevicius et al., "Interleukin-17 mRNA expression in blood and CSF mononuclear cells is augmented in multiple sclerosis," Multiple Sclerosis 5:101-104 (1999).
McCafferty et al., "Phage antibodies: filamentous phage displaying antibody variable domains," Nature 348:552-553 (1990).
McFarland et al., "The role of MRI as a surrogate outcome measure in multiple sclerosis," Multiple Sclerosis 8:40-51 (2002).
Milstein et al., "Hybrid hybridomas and their use in immunohistochemistry," Nature 305:537-539 (1983).
Miyajima et al., "Leucine-Rich a2-Glycoprotein Is a Novel Biomarker of Neurodegenerative Disease in Human Cerebrospinal Fluid and Causes Neurodegeneration in Mouse Cerebral Cortex," PLoS ONE 8(9):e74453 (2013).
Molecular Cloning: A Laboratory Manual, 2nd edition (Sambrook et al., 1989), Table of Contents.
Moore et al., "Astrocytic Tissue Inhibitor of Metalloproteinase-1 (TIMP-1) Promotes Oligodendrocyte Differentiation and Enhances CNS Myelination," J. Neuroscience 31(16):6247-6254 (2011).
Morimoto et al., "Single-step purification of F(ab')2 fragments of mouse monoclonal antibodies (immunoglobulins G1) by hydrophobic interaction high performance liquid chromatography using TSK gel Phenyl-5PW," Journal of Biochemical and Biophysical Methods 24:107-117(1992).
Morrison et al., "Chimeric human antibody molecules: Mouse antigen-binding domains with human constant region domains," PNAS USA 81:6851-6855 (1984).
Morrison, "Success in specification," Nature 368:812-813 (1994).
Munson et al., "Ligand: A Versatile Computerized Approach for Characterization of Ligand-Binding Systems," Anal. Biochem. 107:220-239 (1980).
Neuberger, "Generating high-avidity human Mabs in mice," Nature Biotechnology 14:826 (1996).
O'Sullivan et al., "Methods for the Preparation of Enzyme-Antibody Conjugates for Use in Enzyme Immunoassay," Methods in Enzymology 73:147-166 (1981).
Presta et al., "Humanization of an Antibody Directed Against IgE," J. Immunol. 151(5):2623-2632 (1993).
Presta, "Antibody engineering," Curr. Op. Struct. Biol. 2:593-596 (1992).
Ravetch et al., "Fc Receptors," Annu. Rev. Immunol 9:457-492 (1991).
Riechmann et al., "Reshaping human antibodies for therapy," Nature 332:323-329 (1988).
Schier et al., "Identification of functional and structural amino-acid residues by parsimonious mutagenesis," Gene 169:147-155 (1996).
Shalaby et al., "Development of Humanized Bispecific Antibodies Reactive with Cytotoxic Lymphocytes and Tumor Cells Overexpressing the HER2 Protooncogene," J. Exp. Med., 175:217-225 (1992).
Shopes, "A Genetically Engineered Human IgG Mutant with Enhanced Cytolytic Activity," J. Immunol. 148(9):2918-2922 (1992).
Sidhu et al., "Phage-displayed Antibody Libraries of Synthetic Heavy Chain Complementarity Determining Regions," J. Mol. Biol. 338:299-310 (2004).
Sims et al., "A Humanized CD 18 Antibody Can Block Function without Cell Destruction," J. Immunol., 151(4):2296-2308 (1993).
Starnes et al., "Cutting Edge: IL-17F, a Novel Cytokine Selectively Expressed in Activated T Cells and Monocytes, Regulates Angiogenesis and Endothelial Cell Cytokine Production," J Immunol. 167:4137-4140 (2001).
Stevenson et al., "A Chimeric antibody with dual Fc regions (bisFabFc) prepared by manipulations at the IgG hinge," Anti-Cancer Drug Design 3:219-230 (1989).

(56) References Cited

OTHER PUBLICATIONS

Suresh et al., "Bispecific Monoclonal Antibodies from Hybrid Hybridomas," Methods in Enzymology, 121:210-228 (1986).
Tomioka et al., "Biomarkers for multiple sclerosis," Internal Medicine 53(5):361-365 (2014).
Toy et al., "Cutting Edge: Interleukin 17 Signals through a Heteromeric Receptor Complex," J. Immunol. 177:36-39 (2006).
Van Bezooijen et al., "Interleukin-17: A New Bone Acting Cytokine In Vitro," J. Bone Miner. Res., 14(9):1513-1521 (1999).
Velculescu et al., "Characterization of the Yeast Transcriptome," Cell 88:243-251 (1997).
Velculescu et al., "Serial Analysis of Gene Expression," Science 270:484-487 (1995).
Verhoeyen et al., "Reshaping Human Antibodies: Grafting an Antilysozyme Activity," Science 239:1534-1536 (1988).
Wang et al., "LRG1 promotes angiogenesis by modulating endothelial TGF-β signaling," Nature 499:306-311 (2013).
Waterhouse et al., "Combinatorial infection and in vivo recombination: a strategy for making large phage antibody repertoires," Nuc. Acids. Res., 21(9):2265-2266 (1993).
Wolff et al., "Monoclonal Antibody Homodimers: Enhanced Antitumor Activity in Nude Mice," Cancer Research 53:2560-2565 (1993).
Yao et al., "Herpesvirus Saimiri Encodes a New Cytokine, IL-17, Which Binds to a Novel Cytokine Receptor," Immunity 3:811-821 (1995).
Yao et al., "Human IL-17: A Novel Cytokine Derived from T Cells," J. Immunol., 155:5483-5486 (1995).
Yelton et al., "Affinity Maturation of the BR96 Anti-Carcinoma Antibody by Codon-Based Mutagenesis," J. Immunol. 155:1994-2004 (1995).
Zola, "Using Monoclonal Antibodies: Soluble Antigens," Chapter 6 in Monoclonal Antibodies: A Manual of Techniques, pp. 147-158 (CRC Press, Inc. 1987).

\* cited by examiner

NM_002190 (GenBank)

```
   1 gcaggcacaa actcatccat cccagttga ttgaagaaa caacgatgac tcctgggaag
  61 acctcattgg tgtcactgct actgctgctg agcctggagg ccatagtgaa ggcaggaatc
 121 acaatcccac gaaatccagg atgcccaaat tctgaggaca agaacttccc ccggactgtg
 181 atggtcaacc tgaacatcca taaccggaat acccacccga atcccaaaag gtcctcagat
 241 tactacaacc gatccacctc accttggaat ctccaccgca atgaggaccc tgagagatat
 301 ccctctgtga tctgggaggc aaagtgccgc cacttgggct gcatcaacgc tgatggaaac
 361 gtggactacc acatgaactc tgtcccatc cagcaagaga tctggtcct gcgcagggag
 421 cctccacact gccccaactc gccccaactc gccccaactc cttccggctg gagaagatac tggtgtccgt gggctgcacc
 481 tgtgtcaccc cgattgtcca ccatgtggcc taagagtct gggagccca cactcccaa
 541 agcagttaga ctatggagag ccgacccagc ccctcaggaa cctccatcct tcaaagacag
 601 cctcatttcg gactaaactc attagagttc ttaaggcagt ttgtccaatt aaagcttcag
 661 agtaacact tggccaagat atgagatctg ccctctttt cctcctttcc aagaaggaag
 721 gtttgactga gtaccaattt gcttcttgtt aacttgggg agggctttaa gttattatg
 781 tatttaatat gccctgagat cattgaattc catttaatg aattacctac
 841 tttatttgt ttgtctttt aaagaagata agattctggg cttggaatt tttattattta
 901 aaagtaaaa cctgtattta tttgagctat ttaagatct atttatgttt aagtatttag
 961 aaaaaaggtga aaaagcacta tcatcagttc tgcctagtta aatgtaagat agaattaaat
1021 ggcagtgcaa aatttctgag tctttacaac atacggatat acttttcct cctctttgtt
1081 tttaaaagtt ataacatggc tgaaaagaaa gattaaaact agtccaaatt gtattaattt
1141 aaattttgca attttgtgag gtttacaag agatacagca caagagaaaa tctgttccat
1201 taaaccccta taatataatc cttctgtaat aataaagttt caaaagaaaa tgtttatttg
1261 tttctcattaa atgtatttta gcaaactcag ctcttcccta ttgggaagag ttatgcaaat
1321 tctcctatata gcaaaacaaa gcatgtcttt gagtaacaat gactgaaaa tacccaaaat
1381 tccagttct cgattcaca tgccttcaag actgaacacc gactaaggtt ttcatactat
1441 tagccaatgc tgtagacaga agcattttga taggaataga gcaaataaga taatgccct
1501 gaggaatggc atgtcattat aaagatcat atggggaaaa tgaaaccctc cccaaatac
1561 aagaagttct gggaggagac attgtcttca gactacaatg tccagtttct ccctagact
1621 caggcttcct ttggagatta aggccccctca gagatcaaca gaccaacatt tttctcttcc
1681 tcaagcaaca ctcctagggc ctggcttctg tctgatcaag gcaccacaca accagaaag
1741 gagctgatgg ggcagaacga actttaagta tgagaaaagt tcagcccaag taaaataaaa
1801 actcaatcac attcaattcc agagtagttt caagtttcac atcgtaacca tttcgccc    (SEQ. ID NO:1)
```

FIG. 1A

NP_002181 (GenBank)

```
   1 mtpgktslvs lllslsleai vkagitiprn pgcpnsedkn fprtvmvln ihnrntntnp
  61 krssdyynrs tspwnihrne dperypsviw eakcrhlgci nadgnvdyhm nsvpiqqeil
 121 vlrrepphcp nsfrlekilv svgctcvtpi vhhva    (SEQ. ID NO:2)
```

FIG. 1B

```
AGCCACCAGCGCAACATGACAGTGAAGACCCTGCATGGCCCAGCCATGGTCAAGTACTTG
CTGCTGTCGATATTGGGGCTTGCCTTTCTGAGTGAGGCGGCAGCTCGGAAAATCCCCAAA
GTAGGACATACTTTTTTCCAAAAGCCTGAGAGTTGCCCGCCTGTGCCAGGAGGTAGTATG
AAGCTTGACATTGGCATCATCAATGAAAACCAGCGCGTTTCCATGTCACGTAACATCGAG
AGCCGCTCCACCTCCCCCTGGAATTACACTGTCACTTGGGACCCCAACCGGTACCCCTCG
GAAGTTGTACAGGCCCAGTGTAGGAACTTGGGCTGCATCAATGCTCAAGGAAAGGAAGAC
ATCTCCATGAATTCCGTTCCCATCCAGCAAGAGACCCTGGTCGTCCGGAGGAAGCACCAA
GGCTGCTCTGTTTCTTTCCAGTTGGAGAAGGTGCTGGTGACTGTTGGCTGCACCTGCGTC
ACCCCTGTCATCCACCATGTGCAGTAAGAGGTGCATATCCACTCAGCTGAAGAAG
```
(SEQ. ID NO:3)

FIG. 2A

```
MTVKTLHGPAMVKYLLLSILGLAFLSEAAARKIPKVGHTFFQKPESCPPVPGGSMKLDIG
IINENQRVSMSRNIESRSTSPWNYTVTWDPNRYPSEVVQAQCRNLGCINAQGKEDISMNS
VPIQQETLVVRRKHQGCSVSFQLEKVLVTVGCTCVTPVIHHVQ
```
(SEQ. ID NO:4)

```
4741 tactgtaggt caagaagttg ctagttgcgg agttttttct tgcagttaga ctttacctag
4801 tggtagcagg gccaccaaag ctctgtgtcc cagatggtgt atggcccata atccaccaa
4861 cagcagcaaa ggaccaggca aagagaaca ggagcagaag cctccagcc actagcctt
4921 tgggctcagt ctctccaata atcctggaga gggcttcgt gtgtctgga cacctaccat
4981 gcattctgtg accttttcct agcttccaat aaataactgt ttgacgccca gagtacagga
5041 taccacaatg ctactcttcct gcgtagagca catgttccca tctgctccca ttcctcagga
5101 accttgaatt ctagctctgc tggcctttga gccatgcca gtaaatgtcc tgatggcat
5161 tgcctactat ctccagggca gctgccttg agctttattg gagtacagtt
5221 cacttaccat acaatccaca attgaccctg cacaatttga tgccggttta gtatagtcac
5281 agttcagcag ccatcagcac agtcacctgc agattttact accccccaaa gaaatccagc
5341 ccccttagtc ccctcttctg acatgacata ccctaggcac cctaaaattc ctttgatctc
5401 tgtagactt cctctttctg acatgacata gagaaaggag tcataaattc tccaagtgt
5461 ctgttttctc tttaatgtca ttccctgttt ctcctcacac tccctcccca ttttctgggc
5521 ccagtctcac actggtcctt gcttaccccta aatgtatta attccatcac tctgagtgtg
5581 gtgttttgctg tccgctgaat gccaagagct tcaagagtgt gtgtaaataa agccacacc
5641 ttattttgt attattctga accatggcta ataaaattgtt tcaccaagaa atgtctctct
5701 aagaacaggt gccctccacg ctgtgccct cccacctctt cagctcgtct cctgagtgtg
5761 cagagtggt tccggttggg aaagaagcag cggagaagca aaccatgcct gtgtcagggc
5821 cgattatgca cgcagccacc aacaagctcc caactcccgc gtagagttc atgactttt
5881 cctgcctact atcttgatcc tagtttttt tttgttttt ttttttttaa ggaataatta
5941 cttgattca aaaccagttt gttgtttcgg ctctttctg cataggaagg tccttgaagg tgttagggt
6001 ctaaaaggg ctagtcttcc tgtatgatga atccattcag cagtttgagc tgggatctct
6061 gaatgcaagg gtatgatgga tatactttctt tcttgtcttt gttgtgttt ggttttttgt
6121 tttgtttaa gtcaggggtcc ctctgtcacc aggctgtatt acagtggtgc aatcatggct
6181 cactgcacag tcgaccctcc aggcctcaagc catcttcca cctcagccct ccagtgctta
6241 gaactacagg cgtgcaccac tgtgcccggg taattgtgt gctcaagcca tgtagaaatg
6301 gggtttcacc atgtttgtcc ggctggtcac gaactcctgg ctgagccccac tctgcccgcc
6361 tcatcctccc aaagtgctgg gattataggc ctgagccccac cgtgcctggc cttctgtt
6421 tatcttttgaa aattaaaatag ggcataaatag agaagaagat gtactaccaa tgcagtgggt
6481 ggttttaact ctatagcctt tgggctctgt ggttggtgct cccctccta aataaatgag
6541 gtgtatgcag gcccctcttc tgccttagcg gttggtgct cccctccta gcaaggcccg
6601 gggcacctga ggacagatg agatggaggg cccctgctcc tgggactcca cctgcatccc
6661 acaagtcaac tgtgtcggac agattagctt tacaaagaag agcagcagg gttgggggct
6721 ggccagctgc tgggtcctg gcaagcctgc aggatcatctgt aaagtggtg gggcaggagt
6781 tccacctca tgggtcctg gcaagcctgc agtatccccg agtgccacca gcctgttct
6841 gggcagagc agtttgtgcc cctgaggta gctactgatcc tcttcctg ctattaggta
6901 ttgctctctt tcaggtctc ttgcttttc agaattaga agttatatgt gttcccatat
6961 ttggcagtc tatgattcc atggtatact tttaagagag aatatgaaga aagacta
7021 atgcaacaa tatgacacaa aggaagtac accgacgct accccacgt tcccacgg
```

```
7141  ggcctcccct  cactctgaaa  tggcatccag  gtccatcttg  ccctccacct  ctgcatggct
7201  ctccatgccc  catcgcctct  cccagatcct  agcactgggt  ccacactctc  gccctgtcca
7261  tttaggttga  tgaaagcagg  cagtcaccg   ggtggccag   tcttgcctgt  gggaggaaca
7321  tgcagtctcc  tgtctcatgg  tttgaagtgt  gccaggaagc  ctggcccagc  ccactcccc
7381  ctggagtcct  tcccaggagg  aataacccct  taggtcattg  actataagat  gagttcgctc
7441  actgatcct   tcctctctga  tgagacagga  agaaggtaca  cagtgaccag  gtaggaggag
7501  gagagggagt  agaaaggagg  gatcgggtg   gctgtccct   gcatttgcct  gcttccctgc
7561  acgggtgtcc  cactgccgc   ctctgtcac   cagtgtcatg  ggattctctc  agaagatgaa
7621  aacagcccct  gcttttttgc  tagaatggct  gagcttcat   ggaaggaag   ctggaccaa
7681  gcaacagccg  actaccgaag  gttgcctgga  gcagtgcaga  tgtgggagga  agaagggcct
7741  tggtgcacac  tggcttttct  tcctgactgc  aatgtggcat  tgtgccagct  acctcctctt
7801  tctcggcctc  aggaaaatgg  agagaaagca  gccctgaagg  tggctgtgac  gagggaaggg
7861  gcagagggcc  tgacagtcaa  ccacgcgcta  tattttcctg  ttcttcctta  gggcaagaac
7921  tgcagtggca  aggctgtagg  aggctgctac  gtgggctggg  cattgcctac  acgtgaagag
7981  atcactccgc  gtccctactg  caccgtgtcc  aaagtgcctt  ctgatatgcc  tggcaaacca
8041  aaatcggtga  gcgccagctt  gctccctag   aagacatttc  taaatattca  taacatgctt
8101  gctcaaatca  atcaccttat  tttacatccg  ctccagggag  aaatgaagac  atggtcctac
8161  gttgtctgt   aattattttc  tatgtaaatt  ttgttcctg   ttacaattat  atatgtctta
8221  ggggaaagga  ccatttcaca  tgtgtcacct  catgtgattc  tcaccacagc  cctgtgattg
8281  ctcctgtttt  ataaataatg  acatagttcc  agttgatggc  caaagccaca  gctaacgaga
8341  ggcagagaga  gctcaggctc  ccaggagctt  ccactctcag  accttgcctc  ccggctgcc
8401  ctgagtgaaa  cgcctgctta  gcatttggca  cagccagaag  cagcaagcta  gggtcacaac
8461  acagagaggg  gctgtgtaat  actggctgcc  tctgtgctaa  gaaaaaaaaa  aaatcactgt
8521  gtgtttgttt  atttggtgc   aggcccagtg  ttcttgctta  gacttaatac  tacccttcat
8581  gttaaaataa  aaccaaacaa  aaaccccat                                       (SEQ. ID NO:5)
```

FIG. 3D

```
  1  mgaarsppsa  vpgpligill  lllgvlapgg  aslrlldhra  lvcsqpglnc  tvknstcldd
 61  swihprnltp  sspkdlqiql  hfahtqgqdl  fpvahiewtl  qtdasilyle  gaelsvlqln
121  tnerlcvrfe  flsklrhhhr  rwrftfshfv  vdpdgeyevt  vhhlpkpipd  gdpnhqsknf
181  lvpdceharm  kvttpcmssg  slwdpnitve  tleahqirvs  ftlwnesthy  qilltsfphm
241  enhscfehmh  hipaprpeef  hqrsnvtltl  rnlkgccrhq  vqiqpfissc  indclrhsat
301  vscpempdtp  epipdymplw  vywfitgisi  llvgsvilli  vcmtwriagp  gsekysddtk
361  ytdglpaadl  ippplkprkv  wliysadhpl  yvdvvlkfaq  flltacgtev  aldlleegai
421  seagvmtwvg  rqkqemveesn  skilvlcsrg  trakwqallg  rgapvrlrcd  hgkpvgdift
481  aammilpdf   krpacfgtyv  vcyfsevscd  gdvpdlfgaa  pryplmdrfe  evyfrlqdle
541  mfqpgrmhrv  gelsgdnylr  spggrqlraa  ldrfrdwqvr  cpdwfecenl  ysaddqdaps
601  ldeevfeepl  ippgtgivkr  aplvrepgsq  aclaidplvg  eegaavakl   ephlqprggp
661  apqihtlvl   aaeegalvaa  vepgpladga  avrialageg  eacpligspg  agrnsvlflp
721  vdpedsplgs  stpmaspdll  pedvrehleg  lmislfegsl  scqaggcsr   pamvltdpht
781  pyeeeqrqsv  qsdqgyisrs  spqppeglte  meeeeeeeqd  pgkpalplsp  edleslrslq
841  rqilfrqlqk  nsgwdtmgse  segpsa                                          (SEQ. ID NO:6)
```

FIG. 3E

```
ACACTGGCCAAACAAAAACGAAAGCACTCCGTGCTGGAAGTAGGAGGAGAGTCAGGACTC
CCAGGACAGAGAGTGCACAAACTACCCAGCACAGCCCCCTCCGCCCCCTCTGGAGGCTGA
AGAGGGATTCCAGCCCCTGCCACCCACAGACACGGGCTGACTGGGGTGTCTGCCCCCCTT
GGGGGGGGGCAGCACAGGGCCTCAGGCCTGGGTGCCACCTGGCACCTAGAAGATGCCTGT
GCCCTGGTTCTTGCTGTCCTTGGCACTGGGCCGAAGCCCAGTGGTCCTTTCTCTGGAGAG
GCTTGTGGGGCCTCAGGACGCTACCCACTGCTCTCCGGGCCTCTCCTGCCGCCTCTGGGA
CAGTGACATACTCTGCCTGCCTGGGGACATCGTGCCTGCTCCGGGCCCCGTGCTGGCGCC
TACGCACCTGCAGACAGAGCTGGTGCTGAGGTGCCAGAAGGAGACCGACTGTGACCTCTG
TCTGCGTGTGGCTGTCCACTTGGCCGTGCATGGGCACTGGGAAGAGCCTGAAGATGAGGA
AAAGTTTGGAGGAGCAGCTGACTCAGGGGTGGAGGAGCCTAGGAATGCCTCTCTCCAGGC
CCAAGTCGTGCTCTCCTTCCAGGCCTACCCTACTGCCCGCTGCGTCCTGCTGGAGGTGCA
AGTGCCTGCTGCCCTTGTGCAGTTTGGTCAGTCTGTGGGCTCTGTGGTATATGACTGCTT
CGAGGCTGCCCTAGGGAGTGAGGTACGAATCTGGTCCTATACTCAGCCCAGGTACGAGAA
GGAACTCAACCACACACAGCAGCTGCCTGCCCTGCCCTGGCTCAACGTGTCAGCAGATGG
TGACAACGTGCATCTGGTTCTGAATGTCTCTGAGGAGCAGCACTTCGGCCTCTCCCTGTA
CTGGAATCAGGTCCAGGGCCCCCCAAAACCCCGGTGGCACAAAAACCTGACTGGACCGCA
GATCATTACCTTGAACCACACAGACCTGGTTCCTGCCTCTGTATTCAGGTGTGGCCTCT
GGAACCTGACTCCGTTAGGACGAACATCTGCCCCTTCAGGGAGGACCCCCGCGCACACCA
GAACCTCTGGCAAGCCGCCCGACTGCGACTGCTGACCCTGCAGAGCTGGCTGCTGGACGC
ACCGTGCTCGCTGCCCGCAGAAGCGGCACTGTGCTGGCGGGCTCCGGGTGGGGACCCCTG
CCAGCCACTGGTCCCACCGCTTTCCTGGGAGAACGTCACTGTGGACAAGGTTCTCGAGTT
CCCATTGCTGAAAGGCCACCCTAACCTCTGTGTTCAGGTGAACAGCTCGGAGAAGCTGCA
GCTGCAGGAGTGCTTGTGGGCTGACTCCCTGGGGCCTCTCAAAGACGATGTGCTACTGTT
GGAGACACGAGGCCCCCAGGACAACAGATCCCTCTGTGCCTTGGAACCCAGTGGCTGTAC
TTCACTACCCAGCAAAGCCTCCACGAGGGCAGCTCGCCTTGGAGAGTACTTACTACAAGA
CCTGCAGTCAGGCCAGTGTCTGCAGCTATGGGACGATGACTTGGGAGCGCTATGGGCCTG
CCCCATGGACAAATACATCCACAAGCGCTGGGCCCTCGTGTGGCTGGCCTGCCTACTCTT
TGCCGCTGCGCTTTCCCTCATCCTCCTTCTCAAAAAGGATCACGCGAAAGGGTGGCTGAG
GCTCTTGAAACAGGACGTCCGCTCGGGGGCGGCCGCCAGGGGCCGCGCGGCTCTGCTCCT
CTACTCAGCCGATGACTCGGGTTTCGAGCGCCTGGTGGGCGCCCTGGCGTCGGCCCTGTG
CCAGCTGCCGCTGCGCGTGGCCGTAGACCTGTGGAGCCGTCGTGAACTGAGCGCGCAGGG
GCCCGTGGCTTGGTTTCACGCGCAGCGGCGCCAGACCCTGCAGGAGGGCGGCGTGGTGGT
CTTGCTCTTCTCTCCCGGTGCGGTGGCGCTGTGCAGCGAGTGGCTACAGGATGGGGTGTC
CGGGCCCGGGGCGCACGGCCCGCACGACGCCTTCCGCGCCTCGCTCAGCTGCGTGCTGCC
CGACTTCTTGCAGGGCCGGGCGCCCGGCAGCTACGTGGGGGCCTGCTTCGACAGGCTGCT
CCACCCGGACGCCGTACCCGCCCTTTTCCGCACCGTGCCCGTCTTCACACTGCCCTCCCA
ACTGCCAGACTTCCTGGGGGCCCTGCAGCAGCCTCGCGCCCCGCGTTCCGGGCGGCTCCA
AGAGAGAGCGGAGCAAGTGTCCCGGGCCCTTCAGCCAGCCCTGGATAGCTACTTCCATCC
CCCGGGGACTCCCGCGCCGGGACGCGGGTGGGACCAGGGGCGGGACCTGGGGCGGGGA
CGGGACTTAAATAAAGGCAGACGCTGTTTTTCTAAAAAAA
```
(SEQ. ID NO:7)

FIG. 4A

```
MPVPWFLLSLALGRSPVVLSLERLVGPQDATHCSPGLSCRLWDSDILCLPGDIVPAPGPV
LAPTHLQTELVLRCQKETDCDLCLRVAVHLAVHGHWEEPEDEEKFGGAADSGVEEPRNAS
LQAQVVLSFQAYPTARCVLLEVQVPAALVQFGQSVGSVVYDCFEAALGSEVRIWSYTQPR
YEKELNHTQQLPALPWLNVSADGDNVHLVLNVSEEQHFGLSLYWNQVQGPPKPRWHKNLT
GPQIITLNHTDLVPCLCIQVWPLEPDSVRTNICPFREDPRAHQNLWQAARLRLLTLQSWL
LDAPCSLPAEAALCWRAPGGDPCQPLVPPLSWENVTVDKVLEFPLLKGHPNLCVQVNSSE
KLQLQECLWADSLGPLKDDVLLLETRGPQDNRSLCALEPSGCTSLPSKASTRAARLGEYL
LQDLQSGQCLQLWDDDLGALWACPMDKYIHKRWALVWLACLLFAAALSLILLLKKDHAKG
WLRLLKQDVRSGAAARGRAALLLYSADDSGFERLVGALASALCQLPLRVAVDLWSRRELS
AQGPVAWFHAQRRQTLQEGGVVVLLFSPGAVALCSEWLQDGVSGPAHGPHDAFRASLSC
VLPDFLQGRAPGSYVGACFDRLLHPDAVPALFRTVPVFTLPSQLPDFLGALQQPRAPRSG
RLQERAEQVSRALQPALDSYFHPPGTPAPGRGVGPGAGPGAGDGT
```
(SEQ. ID NO:8)

FIG. 4B

SEQUENCE LISTING

```
<160> NUMBER OF SEQ ID NOS: 8

<210> SEQ ID NO 1
<211> LENGTH: 1859
<212> TYPE: DNA
<213> ORGANISM: Homo sapiens

<400> SEQUENCE: 1
gcaggcacaa actcatccat ccccagttga ttggaagaaa caacgatgac tcctgggaag      60
acctcattgg tgtcactgct actgctgctg agcctggagg ccatagtgaa ggcaggaatc     120
acaatcccac gaaatccagg atgcccaaat tctgaggaca agaacttccc ccggactgtg     180
atggtcaacc tgaacatcca taaccggaat accaatacca atcccaaaag gtcctcagat     240
tactacaacc gatccacctc accttggaat ctccaccgca atgaggaccc tgagagatat     300
ccctctgtga tctgggaggc aaagtgccgc cacttgggct gcatcaacgc tgatgggaac     360
gtggactacc acatgaactc tgtccccatc cagcaagaga tcctggtcct gcgcagggag     420
cctccacact gccccaactc cttccggctg gagaagatac tggtgtccgt gggctgcacc     480
tgtgtcaccc cgattgtcca ccatgtggcc taagagctct ggggagccca cactccccaa     540
agcagttaga ctatggagag ccgacccagc ccctcaggaa ccctcatcct tcaaagacag     600
cctcatttcg gactaaactc attagagttc ttaaggcagt ttgtccaatt aaagcttcag     660
aggtaacact tggccaagat atgagatctg aattacccttt ccctctttcc aagaaggaag     720
gtttgactga gtaccaattt gcttcttgtt tactttttta agggctttaa gttatttatg     780
tatttaatat gccctgagat aactttgggg tataagattc cattttaatg aattacctac     840
tttattttgt ttgtcttttt aaagaagata agattctggg cttgggaatt ttattattta     900
aaaggtaaaa cctgtattta tttgagctat ttaaggatct atttatgttt aagtatttag     960
aaaaaggtga aaaagcacta ttatcagttc tgcctaggta aatgtaagat agaattaaat    1020
ggcagtgcaa aatttctgag tctttacaac atacggatat agtatttcct cctctttgtt    1080
tttaaaagtt ataacatggc tgaaaagaaa gattaaacct actttcatat gtattaattt    1140
aaattttgca atttgttgag gttttacaag agatacagca agtctaactc tctgttccat    1200 taaacccttta taataaaatc cttctgtaat aataaagttt caaaagaaaa tgtttatttg    1260
ttctcattaa atgtatttta gcaaactcag ctcttcccta ttgggaagag ttatgcaaat    1320
tctcctataa gcaaaacaaa gcatgtcttt gagtaacaat gacctggaaa tacccaaaat    1380
```

| | | |
|---|---|---|
| tccaagttct cgatttcaca tgccttcaag actgaacacc gactaaggtt ttcatactat | 1440 | |
| tagccaatgc tgtagacaga agcattttga taggaataga gcaaataaga taatggccct | 1500 | |
| gaggaatggc atgtcattat taaagatcat atggggaaaa tgaaaccctc cccaaaatac | 1560 | |
| aagaagttct gggaggagac attgtcttca gactacaatg tccagtttct cccctagact | 1620 | |
| caggcttcct ttggagatta aggcccctca gagatcaaca gaccaacatt tttctcttcc | 1680 | |
| tcaagcaaca ctcctagggc ctggcttctg tctgatcaag caccacaca acccagaaag | 1740 | |
| gagctgatgg ggcagaacga actttaagta tgagaaaagt tcagcccaag taaaataaaa | 1800 | |
| actcaatcac attcaattcc agagtagttt caagtttcac atcgtaacca ttttcgccc | 1859 | |

<210> SEQ ID NO 2
<211> LENGTH: 155
<212> TYPE: PRT
<213> ORGANISM: Homo sapiens

<400> SEQUENCE: 2

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 3
<211> LENGTH: 535
<212> TYPE: DNA
<213> ORGANISM: Homo sapiens

<400> SEQUENCE: 3

| | |
|---|---|
| agccaccagc gcaacatgac agtgaagacc ctgcatggcc cagccatggt caagtacttg | 60 |
| ctgctgtcga tattggggct tgcctttctg agtgaggcgg cagctcggaa aatccccaaa | 120 |
| gtaggacata cttttttcca aaagcctgag agttgcccgc tgtgccagg aggtagtatg | 180 |
| aagcttgaca ttggcatcat caatgaaaac cagcgcgttt ccatgtcacg taacatcgag | 240 |
| agccgctcca cctcccctg gaattacact gtcacttggg accccaaccg gtacccctcg | 300 |
| gaagttgtac aggcccagtg taggaacttg gctgcatca atgctcaagg aaaggaagac | 360 |
| atctccatga attccgttcc catccagcaa gagaccctgg tcgtccggag gaagcaccaa | 420 |
| ggctgctctg tttctttcca gttggagaag gtgctggtga ctgttggctg cacctgcgtc | 480 |
| acccctgtca tccaccatgt gcagtaagag gtgcatatcc actcagctga agaag | 535 |

<210> SEQ ID NO 4
<211> LENGTH: 163
<212> TYPE: PRT
<213> ORGANISM: Homo sapiens

<400> SEQUENCE: 4

Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Arg Lys Ile
            20                  25                  30

Pro Lys Val Gly His Thr Phe Phe Gln Lys Pro Glu Ser Cys Pro Pro
        35                  40                  45

Val Pro Gly Gly Ser Met Lys Leu Asp Ile Gly Ile Ile Asn Glu Asn
    50                  55                  60

Gln Arg Val Ser Met Ser Arg Asn Ile Glu Ser Arg Ser Thr Ser Pro
65                  70                  75                  80

Trp Asn Tyr Thr Val Thr Trp Asp Pro Asn Arg Tyr Pro Ser Glu Val
                85                  90                  95

Val Gln Ala Gln Cys Arg Asn Leu Gly Cys Ile Asn Ala Gln Gly Lys
            100                 105                 110

Glu Asp Ile Ser Met Asn Ser Val Pro Ile Gln Gln Glu Thr Leu Val
        115                 120                 125

Val Arg Arg Lys His Gln Gly Cys Ser Val Ser Phe Gln Leu Glu Lys
    130                 135                 140

Val Leu Val Thr Val Gly Cys Thr Cys Val Thr Pro Val Ile His His
145                 150                 155                 160

Val Gln

<210> SEQ ID NO 5
<211> LENGTH: 8608
<212> TYPE: DNA
<213> ORGANISM: Homo sapiens

<400> SEQUENCE: 5
ctgggcccgg gctggaagcc ggaagcgagc aaagtggagc cgactcgaac tccaccgcgg      60
aaaagaaagc tcagaacgt tcgttcgctg cgtccccagc cggggccgag ccctccgcga     120
cgccagccgg gccatggggg ccgcacgcag cccgccgtcc gctgtcccgg ggcccctgct     180
ggggctgctc ctgctgctcc tgggcgtgct ggccccgggt ggcgcctccc tgcgactcct     240
ggaccaccgg gcgctggtct gctcccagcc ggggctaaac tgcacggtca agaatagtac     300
ctgcctggat gacagctgga ttcaccctcg aaacctgacc ccctcctccc caaaggacct     360
gcagatccag ctgcactttg cccacaccca acaaggagac ctgttcccg tggctcacat     420 cgaatggaca ctgcagacag acgccagcat cctgtacctc gagggtgcag agttatctgt     480
cctgcagctg aacaccaatg aacgtttgtg cgtcaggttt gagtttctgt ccaaactgag     540
gcatcaccac aggcggtggc gttttacctt cagccacttt gtggttgacc ctgaccagga     600
atatgaggtg accgttcacc acctgccaa gccatccct gatggggacc caaaccacca     660
gtccaagaat tccttgtgc ctgactgtga gcacgccagg atgaaggtaa ccacgccatg     720
catgagctca ggcagcctgt gggaccccaa catcaccgtg gagaccctgg aggcccacca     780
gctgcgtgtg agcttcaccc tgtggaacga atctacccat taccagatcc tgctgaccag     840
ttttccgcac atggagaacc acagttgctt tgagcacatg caccacatac ctgcgcccag     900

-continued

```
accagaagag ttccaccagc gatccaacgt cacactcact ctacgcaacc ttaaagggtg      960
ctgtcgccac caagtgcaga tccagcccct cttcagcagc tgcctcaatg actgcctcag     1020
acactccgcg actgtttcct gcccagaaat gccagacact ccagaaccaa ttccggacta     1080
catgcccctg tgggtgtact ggttcatcac gggcatctcc atcctgctgg tgggctccgt     1140
catcctgctc atcgtctgca tgacctggag gctagctggg cctggaagtg aaaaatacag     1200
tgatgacacc aaatacaccg atggcctgcc tgcggctgac ctgatccccc caccgctgaa     1260
gcccaggaag gtctggatca tctactcagc cgaccacccc ctctacgtgg acgtggtcct     1320
gaaattcgcc cagttcctgc tcaccgcctg cggcacggaa gtggccctgg acctgctgga     1380
agagcaggcc atctcggagg caggagtcat gacctgggtg ggccgtcaga agcaggagat     1440
ggtggagagc aactctaaga tcatcgtcct gtgctcccgc ggcacgcgcg ccaagtggca     1500
ggcgctcctg ggccggggggg cgcctgtgcg gctgcgctgc gaccacggaa agcccgtggg     1560
ggacctgttc actgcagcca tgaacatgat cctcccggac ttcaagaggc cagcctgctt     1620
cggcacctac gtagtctgct acttcagcga ggtcagctgt gacggcgacg tccccgacct     1680
gttcggcgcg cgccgccggt acccgctcat ggacaggttc gaggaggtgt acttccgcat     1740
ccaggacctg agatgttcc agccgggccg catgcaccgc gtaggggagc tgtcggggga     1800
caactacctg cggagcccgg gcggcaggca gctccgcgcc gccctggaca ggttccggga     1860
ctggcaggtc cgctgtcccg actggttcga atgtgagaac ctctactcag cagatgacca     1920
ggatgccccg tccctggacg aagaggtgtt tgaggagcca ctgctgcctc cgggaaccgg     1980
catcgtgaag cggcgccccc tggtgcgcga gcctggctcc caggcctgcc tggccataga     2040
cccgctggtc ggggaggaag gaggagcagc agtggcaaag ctggaacctc acctgcagcc     2100
ccggggtcag ccagcgccgc agcccctcca caccctggtg ctcgccgcag aggagggggc     2160
cctggtggcc gcggtggagc ctgggcccct ggctgacggt gccgcagtcc ggctggcact     2220
ggcgggggag ggcgaggcct gcccgctgct gggcagcccg ggcgctgggc gaaatagcgt     2280
cctcttcctc cccgtggacc ccgaggactc gccccttggc agcagcaccc ccatggcgtc     2340
tcctgacctc cttccagagg acgtgaggga gcacctcgaa ggcttgatgc tctcgctctt     2400
cgagcagagt ctgagctgcc aggcccaggg gggctgcagt agacccgcca tggtcctcac     2460
agacccacac acgccctacg aggaggagca gcggcagtca gtgcagtctg accagggcta     2520
catctccagg agctcccgc agccccccga gggactcacg gaaatggagg aagaggagga     2580
agaggagcag gacccaggga agccggccct gccactctct cccgaggacc tggagagcct     2640
gaggagcctc cagcggcagc tgcttttccg ccagctgcag aagaactcgg gctgggacac     2700
gatggggtca gagtcagagg ggcccagtgc atgagggcgg ctcccagggg accgcccaga     2760
tcccagcttt gagagaggag tgtgtgtgca cgtattcatc tgtgtgtaca tgtctgcatg     2820
tgtatatgtt cgtgtgtgaa atgtaggctt taaaatgtaa atgtctggat tttaatccca     2880
ggcatccctc ctaactttc tttgtgcagc ggtctggtta tcgtctatcc caggggaat      2940
ccacacagcc cgctcccagg agctaatggt agagcgtcct tgaggctcca ttattcgttc     3000
attcagcatt tattgtgcac ctactatgtg cgggcattt gggataccaa gataaattgc      3060
atgcggcatg gccccagcca tgaaggaact taaccgctag tgccgaggac acgttaaacg     3120
aacaggatgg gccgggcacg gtggctcacg cctgtaatcc cagcacactg ggaggccgag     3180
gcaggtggat cactctgagg tcaggagttt gagccagcct ggccaacatg gtgaaacccc     3240
atctccacta aaaatagaaa aattagccgg gcatggtgac acatgcctgt agtcctagct     3300
```

-continued

| | |
|---|---|
| acttgggagg ctgaggcagg agaattgctt gaatctggga ggcagaggtt gcagtgagcc | 3360 |
| gagattgtgc cattgcactg cagcctggat gacagagcga gactctatct caaaaaaaaa | 3420 |
| aaaaaaaaaa gatggtcacg cgggatgtaa acgctgaatg ggccaggtgc agtggctcat | 3480 |
| gcttgtaatc ccagcacttt gggaaggcga ggcaggtgga ttgcttgagc tcaggagttc | 3540 |
| aagaccagcc tgggcgacat agtgagacct catctctacc taaattttt tttagtcagt | 3600 |
| catggtggca catgcctgta gtcccagcta ctcgggaggc tgatgccaga tgatcacttg | 3660 |
| agcccaggag gtagaggctg cagtgagcta taatggtacc attgcaatcc agcctgggca | 3720 |
| gcagagtgag accctgtctc aaaaaaaata aaaagtagaa agatggagt ggaagcctgc | 3780 |
| ccagggttgt gagcatgcac gggaaaggca cccaggtcag gggggatccc cgaggagatg | 3840 |
| cctgagctga aggattgtgg ttggggaaag cgtagtccca gcaaggaagc agtttgtggg | 3900 |
| taagtgctgg gaggtgagtg gagtgagctt gtcagggagc tgctggtgga gcctggaggg | 3960 |
| gaaggaggga ggcagtgaga gagatcgggg tgggggtgg ggggatgtcg ccagagctca | 4020 |
| ggggtgggga cagccttgtg cgcatcagtc ctgaggcctg gggcaccttt cgtctgatga | 4080 |
| gcctctgcat ggagagaggc tgagggctaa acacagctgg atgtcacctg agttcattta | 4140 |
| taggaagaga gaaatgtcga ggtgaaacgt aaaagcatct ggcaggaagg tgagtctgaa | 4200 |
| gccctgcacc cgcgttccga ctatcagtgg ggagctgtta gcacgtagga ttcttcagag | 4260 |
| cagctgggct ggagctcccc tgagctcagg aagccccagg gtgcaagggc aaggaaatga | 4320 |
| ggggtggtgg gtcagtgaag atctgggcag accttgtgtg gggaaggggt gctgctgtga | 4380 |
| cttcagggtc tgaggtccaa agacagcatt tgaaaagagg ctctgaagcc agtgtttgaa | 4440 |
| gaatttgttc ctgaagtacc tcctgggggt aggctagagg cttctggctt cagggtcctg | 4500 |
| aagaacacat tgaggtgccg tctgacactg gaatagggtg cccttcattc ctatgcctga | 4560 |
| gtccttaact atatttccaa cctccagtga ggaggagaag attcggaaat gtgacaggag | 4620 |
| agcaaacagg acagtttgca tgtgtgtgtg cgcacacata catgtgcgtg aaagattatc | 4680 |
| aataaaagtg cataaatttg ttgatctggt aagagtttct agcaggaagg tcgagccact | 4740 |
| tactgtaggt caagaagttg ctagttgcgg agttttttct tgcagttaga ctttacctag | 4800 |
| tggtagcagg gccaccaaag ctctgtgtcc cagatggtgt atggcccata atccacccaa | 4860 |
| cagcagcaaa ggaccaggca aaggagaaca ggagcagaag cctcccagcc actagccttt | 4920 |
| tgggctcagt ctctccaata atcctggaga ggggcttcgt tgggtctgga cacctaccat | 4980 |
| gcattctgtg acctttccct agcttccaat aaataactgt ttgacgccca gagtacagga | 5040 |
| taccacaatg cactcttcct gcgtagagca catgttccca tctgctccca ttcctcagga | 5100 |
| accttgaatt ctagctctgc tggcctttga gcccatgcca gtaaatgtcc tgatgggcat | 5160 |
| tgcctactat ctccagggca gctgcctttg tcctcctaac agctttattg gagtacagtt | 5220 |
| cacttaccat acaatccaca attgaccctg cacaatttga tgccggttta gtatagtcac | 5280 |
| agttcagcag ccatcagcac agtcagtctt agagtttact accccaaaa gaaatccagc | 5340 |
| ccccttagt caccacccca acctcccat ccctaggcac ccctaggcta ctttgatctc | 5400 |
| tgtagacttg cctcttctgg acatgacata gagaaaggag tcataaattc tccaaggtgt | 5460 |
| ctgtttcttc tttaatgtca ttccctgttt ctcctcacat tccctcccca tttcctgggc | 5520 |
| ccagtctcac actggtcctt gcttacccta aatgctatta attccatcac tctgagtatg | 5580 |
| gtgtttgctg tccgctgaat gccaagagct tcaagagtgt gtgtaaataa agccacacct | 5640 |

```
ttatttttgt attattctga accatggcta ataaattgtt tcaccaagaa atgtctctct    5700
aagaacaggt gccctccacg ctgtgcccct cccacctctt cagctcgtct cctgagtgtg    5760
cagaggtggt tccggttggg aaagaagcag cggagcatct aaccatgcct gtgtccaggc    5820
cgattatgca cgcagccacc aacaagctcc caactcccgc gtagagtttc atgactttt     5880 cctgcctact atcttgatcc tagttttttt tttgttttt ttttttttaa ggaataatta     5940
ctttgattca aaaccagttt ctcttttctg cataggaagg tccttgaagg tgtttagggt    6000
ctaaaagggt tggtgttcgg tctctgaaac atccattcag cagtttgagc tgggatctct    6060
gaatgcaagg gtatgatgga tatacttctt tcttgctttt gttgtgtttt ggttttttgt    6120 ttgttttaa gtcagggtct ctctgtcacc aggctgtatt acagtggtgc aatcatggct      6180
cactgcagcc tcgacctccc aggctcaagc catctttcca cctcagcctg ccagtggcta    6240
gaactacagg cgtgcaccac tgtgcccggc taatttgtgt gtatatattt tgtagaaatg    6300
gggtttcacc atgttgtcca ggctggtcac gaactcctgg gctcaagcca tctgcccgcc    6360
tcatcctccc aaagtgctgg gattataggc ctgagcccac cgtgcctggc cttcctgtt    6420 tatctttgaa aattaaatag ggcataagag agaagaagat gtacttacaa tgcagtgggt    6480
ggttttaact ctatagcctt tgggctctgt ggttggtgct ccccttccta aataaatgag    6540
gtgtatgcag ggccctcttc tgccttagcg ccctgccagc tgggactcca gcaaggcccg    6600
gggcacctga ggacagagtg agatggaggg ccgctgctcc agcagccggg cctgcatccc    6660
acaagtcaac tgtgtcggac agaggatcct tacaaagaag aggcagcagg gttggggct      6720 ggccagctgc tcgtccgccc taggtagctt gctcatctgt aaagtgggtg gggcaggagt    6780
tcccacctca tggggtcctg gcaagcctgc agtatccccg agtggcacca gcctgcttct    6840
ggggcagagc agtttgtgcc ccctgaggta ccactgatcc tctttccctg ctattaggta    6900
ttgctctctt cctccggtgt ttgccttttc agattataga agtaatatgt gttcccatat    6960
ttggcgtctc tcaggagctc aggaagtact tggctgagtg aacatgtcca ttgtggaaaa    7020
atggcaacaa tatggattcc atgggtatat tttatagaag aatatgaaga aaagcagcta    7080
cccctaaacc cattgcacaa gctgttcatg ttaattctgt acccgacgct ttccccacgg    7140
ggcctcccct cactctgaaa tggcatccag gtccatcttg ccctccacct ctgcatggct    7200
ctccatgccc catcgcctct cccagatcct agcactgggt ccacactctc gccctgtcca    7260
tttaggttga tgaaagcagg cagtcacccg ggtgggccag tcttgcctgt gggaggaaca    7320
tgcagtctcc tgtctcatgg tttgaagtgt gccaggaagc ctggcccagc ccacctcccc    7380
ctggagtcct tcccaggagg aataacccct taggtcattg actataagat gagttcgctc    7440
actggatcct tcctctctga tgagacagga agaaggtaca cagtgaccag gtaggaggag    7500
gagagggagt agaaaggagg gatgcgggtg gctggtccct gcatttgcct gcttccctgc    7560
acgggtgtcc cactggccgc ctctgctcac cagtgtcatg ggattctctc agaagatgaa    7620
aacagcccct gctttttgc tagaatggct gagctttcat ggaaaggaag ctggacccaa      7680
gcaacagccg actaccgaag gttgcctgga gcagtgcaga tgtgggagga agaagggcct    7740
tggtgcacac tggcttttct tcctgactgc aatgtgcat tgtgccagct acctcctctt       7800
tctcggcctc aggaaaatgg agagaaagca gccctgaagg tggctgtgac gagggaaggg    7860
gcagagggcc tgcagtcaa ccacgcgcta tattttcctg ttcttcctta gggcaagaac      7920
tgcatggcca gactcaggca aggcctaggt gtgggctggg cattgcctac acgtgaagag    7980
atcactccgc gtccctactg cacctgtcac aaagtgcctt ctgatatgcc tggcaaacca    8040
```

```
aaatcggtga gcgccagctt gcttccctag aagacatttc taaatattca taacatgctt    8100
gctcaaatca atcaccttat tttacatccg ctccagggag aaatgaagac atggtcctac    8160
gttgttctgt aattattttc tatgtaaatt ttgttccttg ttacaattat atatgtctta    8220
ggggaaagga ccatttcaca tgtgtcacct catgtgattc tcaccacagc cctgtgattg    8280
ctcctgtttt ataaataatg acatagttcc agttgatggc caaagccaca gctaacgaga    8340
ggcagagaga gctcaggctc ccaggagctt ccactctcag accttgcctc ccgggctgcc    8400
ctgagtgaaa cgcctgctta gcatttggca cagccagaag cagcaagcta gggtcacaac    8460
acagagaggg gctgtgtaat actggctgcc tctgtgctaa gaaaaaaaaa aaatcactgt    8520
gtgtttgttt attttggtgc aggcccagtg ttcttgctta gacttaatac taccttcat    8580 gttaaaataa aaccaaacaa aaacccat                                      8608
```

<210> SEQ ID NO 6
<211> LENGTH: 866
<212> TYPE: PRT
<213> ORGANISM: Homo sapiens

<400> SEQUENCE: 6

```
Met Gly Ala Ala Arg Ser Pro Pro Ser Ala Val Gly Pro Leu Leu
1               5                   10                  15

Gly Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270
```

```
Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
                340                 345                 350

Glu Lys Tyr Ser Asp Asp Thr Lys Tyr Thr Asp Gly Leu Pro Ala Ala
            355                 360                 365

Asp Leu Ile Pro Pro Pro Leu Lys Pro Arg Lys Val Trp Ile Ile Tyr
        370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
            435                 440                 445

Arg Gly Thr Arg Ala Lys Trp Gln Ala Leu Leu Gly Arg Gly Ala Pro
        450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
                500                 505                 510

Val Pro Asp Leu Phe Gly Ala Ala Pro Arg Tyr Pro Leu Met Asp Arg
            515                 520                 525

Phe Glu Glu Val Tyr Phe Arg Ile Gln Asp Leu Glu Met Phe Gln Pro
        530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
                580                 585                 590

Ala Asp Asp Gln Asp Ala Pro Ser Leu Asp Glu Glu Val Phe Glu Glu
            595                 600                 605

Pro Leu Leu Pro Pro Gly Thr Gly Ile Val Lys Arg Ala Pro Leu Val
        610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
            660                 665                 670

Glu Glu Gly Ala Leu Val Ala Ala Val Glu Pro Gly Pro Leu Ala Asp
        675                 680                 685
```

| | | | | | | | | | | | |
|---|---|---|---|---|---|---|---|---|---|---|---|
|Gly|Ala|Ala|Val|Arg|Leu|Ala|Leu|Ala|Gly|Glu|Gly|Glu|Ala|Cys|Pro|
| |690| | | |695| | | |700| | |

Leu Leu Gly Ser Pro Gly Ala Gly Arg Asn Ser Val Leu Phe Leu Pro
705                710                 715                 720

Val Asp Pro Glu Asp Ser Pro Leu Gly Ser Ser Thr Pro Met Ala Ser
             725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
            755                 760                 765

Ser Arg Pro Ala Met Val Leu Thr Asp Pro His Thr Pro Tyr Glu Glu
770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
            835                 840                 845

Gln Lys Asn Ser Gly Trp Asp Thr Met Gly Ser Glu Ser Glu Gly Pro
850                 855                 860

Ser Ala
865

<210> SEQ ID NO 7
<211> LENGTH: 2380
<212> TYPE: DNA
<213> ORGANISM: Homo sapiens

<400> SEQUENCE: 7

```
acactggcca acaaaaacg aaagcactcc gtgctggaag taggaggaga gtcaggactc      60
ccaggacaga gagtgcacaa actacccagc acagccccct ccgccccctc tggaggctga    120
agagggattc cagcccctgc cacccacaga cacgggctga ctggggtgtc tgccccctt     180
ggggggggggc agcacagggc ctcaggcctg ggtgccacct ggcacctaga agatgcctgt   240
gccctggttc ttgctgtcct tggcactggg ccgaagccca gtggtccttt ctctggagag    300
gcttgtgggg cctcaggacg ctacccactg ctctccgggc ctctcctgcc gcctctggga    360
cagtgacata ctctgcctgc ctggggacat cgtgcctgct ccgggccccg tgctggcgcc    420
tacgcacctg cagacagagc tggtgctgag gtgccagaag gagaccgact gtgacctctg    480
tctgcgtgtg gctgtccact tggccgtgca tgggcactgg gaaagagcctg aagatgagga    540
aaagtttgga ggagcagctg actcagggta ggaggagcct aggaatgcct ctctccaggc    600
ccaagtcgtg ctctccttcc aggcctaccc tactgcccgc tgcgtcctgc tggaggtgca    660
agtgcctgct gccttgtgc agtttggtca gtctgtgggc tctgtggtat atgactgctt     720
cgaggctgcc ctagggagtg aggtacgaat ctggtcctat actcagccca ggtacgagaa    780
ggaactcaac cacacacagc agctgcctgc cctgccctgg ctcaacgtgt cagcagatgg    840
tgacaacgtg catctggttc tgaatgtctc tgaggagcag cacttcggcc tctccctgta    900
ctggaatcag gtccagggcc ccccaaaacc ccggtggcac aaaaaacctga ctggaccgca    960
gatcattacc ttgaaccaca cagacctggt tccctgcctc tgtattcagg tgtggcctct   1020
ggaacctgac tccgttagga cgaacatctg ccccttcagg gaggaccccc gcgcacacca    1080
```

```
gaacctctgg caagccgccc gactgcgact gctgaccctg cagagctggc tgctggacgc    1140
accgtgctcg ctgcccgcag aagcggcact gtgctggcgg gctccgggtg gggacccctg    1200
ccagccactg gtcccaccgc tttcctggga gaacgtcact gtggacaagg ttctcgagtt    1260
cccattgctg aaaggccacc ctaacctctg tgttcaggtg aacagctcgg agaagctgca    1320
gctgcaggag tgcttgtggg ctgactccct ggggcctctc aaagacgatg tgctactgtt    1380
ggagacacga ggcccccagg acaacagatc cctctgtgcc ttggaaccca gtggctgtac    1440
ttcactaccc agcaaagcct ccacgagggc agctcgcctt ggagagtact tactacaaga    1500
cctgcagtca ggccagtgtc tgcagctatg gacgatgac ttgggagcgc tatgggcctg     1560
ccccatggac aaatacatcc acaagcgctg ggccctcgtg tggctggcct gctactcctt    1620
tgccgctgcg ctttccctca tcctccttct caaaaaggat cacgcgaaag ggtggctgag    1680
gctcttgaaa caggacgtcc gctcgggggc ggccgccagg ggccgcgcgg ctctgctcct    1740
ctactcagcc gatgactcgg gtttcgagcg cctggtgggc ccctggcgt cggccctgtg     1800 ccagctgccg ctgcgcgtgg ccgtagacct gtggagccgt cgtgaactga gcgcgcaggg    1860
gcccgtggct tggtttcacg cgcagcgcg ccagaccctg caggagggcg cgtggtggt     1920 cttgctcttc tctcccggtg cggtggcgct gtgcagcgag tggctacagg atggggtgtc    1980
cgggcccggg gcgcacggcc cgcacgacgc cttccgcgcc tcgctcagct gcgtgctgcc    2040
cgacttcttg cagggccggg cgcccggcag ctacgtgggg gcctgcttcg acaggctgct    2100
ccacccggac gccgtacccg cccttttccg caccgtgccc gtcttcacac tgccctccca    2160
actgccagac ttcctgggg ccctgcagca gcctcgcgcc ccgcgttccg gcggctcca     2220 agagagagcg gagcaagtgt cccgggccct tcagccagcc ctggatagct acttccatcc    2280
cccggggact cccgcgccgg gacgcgggt gggaccaggg gcgggacctg gggcggggga     2340
cgggacttaa ataaaggcag acgctgtttt tctaaaaaaa                          2380
```

<210> SEQ ID NO 8
<211> LENGTH: 705
<212> TYPE: PRT
<213> ORGANISM: Homo sapiens

<400> SEQUENCE: 8

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140
```

```
Pro Ala Ala Leu Val Gln Phe Gly Gln Ser Val Gly Ser Val Val Tyr
145                 150                 155                 160

Asp Cys Phe Glu Ala Leu Gly Ser Glu Val Arg Ile Trp Ser Tyr
        165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
                195                 200                 205

Val Leu Asn Val Ser Glu Glu Gln His Phe Gly Leu Ser Leu Tyr Trp
210                 215                 220

Asn Gln Val Gln Gly Pro Lys Pro Arg Trp His Lys Asn Leu Thr
225                 230                 235                 240

Gly Pro Gln Ile Ile Thr Leu Asn His Thr Asp Leu Val Pro Cys Leu
                    245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
        275                 280                 285

Ala Arg Leu Arg Leu Leu Thr Leu Gln Ser Trp Leu Leu Asp Ala Pro
290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
            325                 330                 335

Val Asp Lys Val Leu Glu Phe Pro Leu Leu Lys Gly His Pro Asn Leu
                340                 345                 350

Cys Val Gln Val Asn Ser Ser Glu Lys Leu Gln Leu Gln Glu Cys Leu
            355                 360                 365

Trp Ala Asp Ser Leu Gly Pro Leu Lys Asp Asp Val Leu Leu Leu Glu
370                 375                 380

Thr Arg Gly Pro Gln Asp Asn Arg Ser Leu Cys Ala Leu Glu Pro Ser
385                 390                 395                 400

Gly Cys Thr Ser Leu Pro Ser Lys Ala Ser Thr Arg Ala Ala Arg Leu
                405                 410                 415

Gly Glu Tyr Leu Leu Gln Asp Leu Gln Ser Gly Gln Cys Leu Gln Leu
                420                 425                 430

Trp Asp Asp Asp Leu Gly Ala Leu Trp Ala Cys Pro Met Asp Lys Tyr
        435                 440                 445

Ile His Lys Arg Trp Ala Leu Val Trp Leu Ala Cys Leu Leu Phe Ala
        450                 455                 460

Ala Ala Leu Ser Leu Ile Leu Leu Leu Lys Lys Asp His Ala Lys Gly
465                 470                 475                 480

Trp Leu Arg Leu Leu Lys Gln Asp Val Arg Ser Gly Ala Ala Ala Arg
                485                 490                 495

Gly Arg Ala Ala Leu Leu Leu Tyr Ser Ala Asp Asp Ser Gly Phe Glu
                500                 505                 510

Arg Leu Val Gly Ala Leu Ala Ser Ala Leu Cys Gln Leu Pro Leu Arg
                515                 520                 525

Val Ala Val Asp Leu Trp Ser Arg Arg Glu Leu Ser Ala Gln Gly Pro
            530                 535                 540

Val Ala Trp Phe His Ala Gln Arg Arg Gln Thr Leu Gln Glu Gly Gly
545                 550                 555                 560
```

-continued

```
Val Val Val Leu Leu Phe Ser Pro Gly Ala Val Ala Leu Cys Ser Glu
            565                 570                 575

Trp Leu Gln Asp Gly Val Ser Gly Pro Gly Ala His Gly Pro His Asp
            580                 585                 590

Ala Phe Arg Ala Ser Leu Ser Cys Val Leu Pro Asp Phe Leu Gln Gly
            595                 600                 605

Arg Ala Pro Gly Ser Tyr Val Gly Ala Cys Phe Asp Arg Leu Leu His
            610                 615                 620

Pro Asp Ala Val Pro Ala Leu Phe Arg Thr Val Pro Val Phe Thr Leu
625                 630                 635                 640

Pro Ser Gln Leu Pro Asp Phe Leu Gly Ala Leu Gln Gln Pro Arg Ala
            645                 650                 655

Pro Arg Ser Gly Arg Leu Gln Glu Arg Ala Glu Gln Val Ser Arg Ala
            660                 665                 670

Leu Gln Pro Ala Leu Asp Ser Tyr Phe His Pro Pro Gly Thr Pro Ala
            675                 680                 685

Pro Gly Arg Gly Val Gly Pro Gly Ala Gly Pro Gly Ala Gly Asp Gly
            690                 695                 700

Thr
705
```

GENE EXPRESSION MARKERS AND TREATMENT OF MULTIPLE SCLEROSIS

CROSS REFERENCE TO RELATED APPLICATION

This application is a continuation of International Application No. PCT/US2016/015344 having an international filing date of Jan. 28, 2016, the entire contents of which are incorporated herein by reference, and which relates to and claims the benefit of priority under 35 U.S.C. § 119 to U.S. Provisional Application No. 62/108,914 filed Jan. 28, 2015, which is herein incorporated by reference in its entirety.

SEQUENCE LISTING

The instant application contains a Sequence Listing which has been submitted electronically in ASCII format and is hereby incorporated by reference in its entirety. Said ASCII copy, created on Jul. 25, 2017, is named P32496US1SeqList.txt and is 34,389 bytes in size.

FIELD OF THE INVENTION

The present invention concerns markers of multiple sclerosis and use of the markers in identifying patients with MS, at risk of developing MS, and/or for treatment with IL-17 antagonists, such as anti-IL-17 antibodies.

DESCRIPTION OF THE RELATED ART

Multiple Sclerosis

Multiple sclerosis (MS) is a demyelinating disease affecting the central nervous system, in which episodes of inflammation result in a highly variable course and progression of symptoms (Compston, A. et al., Lancet 372:1502-1517 (2008)). Onset is typically between the ages of 30-50, with higher prevalence in women and great geographic variability (Rosati, G., Neurol Sci 22:117-139 (2001)). There are a broad range of symptoms, reflecting the diverse anatomical targets of demyelination, but typical syndromes include: weakness, fatigue, loss of vision, cognitive impairment and impaired balance and coordination (Compston, supra). MS episodes are erratic in timing as well, leading to the general principle that MS lesions are disseminated in both space (location) and time (Adams, R et al., Principles of Neurology sixth edn, (McGraw-Hill, 1997)). These symptoms can often be sufficient to make the diagnosis of MS, but magnetic resonance imaging (MRI) is also helpful, along with analysis of cerebrospinal fluid and nerve evoked potential measurements. MS typically begins with reversible neurological deficits (relapsing-remitting phase, or RRMS), that progress eventually to fixed disability in later life (secondary progressive phase) (Adams et al., supra). Like other aspects of the disease, the pattern, severity and timing of this progression can be very different among patients, with some experiencing profound disability with rapid progression at the outset (primary progressive MS or PPMS), while a small number of other patients have isolated, relatively mild symptoms.

There is currently no cure for MS, and despite some recent progress in novel treatments, the disease remains a therapeutic challenge (Kieseier, B. C., et al., Curr Opin Neurol 20:286-293 (2007)). Standard treatment includes corticosteroids aimed at suppressing the inflammatory response during acute relapse, sometimes with plasmaphoresis to remove circulating antibodies from the bloodstream (Giovannoni, G. et al., Curr Opin Neurol 20:261-268 (2007)). Glatiramer acetate and interferonβ1a are also used in RRMS, but are not particularly effective in PPMS, nor in altering the eventual course of MS, even with early intervention (Compston et al., supra; Kieseier et al., supra). A more specific immunotherapy uses monoclonal antibodies to target particular surface molecules involved in MS. Natalizumab binds to α4 integrin on white blood cells, thereby reducing their numbers, but due to adverse reactions of progressive multifocal leukoencephalopathy (PML), this drug is used only when other treatments have failed (Kieseier et al., supra). Other monoclonal antibodies, rituximab (an anti-CD20 antibody) and daclizumab (targeting CD-25), have a similar rationale, but again are not curative, and have other immunological side-effects.

IL-17

Interleukin-17A (IL-17A, often referred to as IL-17 in the field) is a T-cell derived pro-inflammatory molecule that stimulates epithelial, endothelial and fibroblastic cells to produce other inflammatory cytokines and chemokines including IL-6, IL-8, G-CSF, and MCP-1 (see, Yao, Z. et al., J. Immunol., 122(12):5483-5486 (1995); Yao, Z. et al, Immunity, 3(6):811-821 (1995); Fossiez, F., et al., J. Exp. Med., 183(6): 2593-2603 (1996); Kennedy, J., et al., J. Interferon Cytokine Res., 16(8):611-7 (1996); Cai, X. Y., et al., Immunol. Lett, 62(1):51-8 (1998); Jovanovic, D. V., et al., J. Immunol., 160(7):3513-21 (1998); Laan, M., et al., J. Immunol., 162(4):2347-52 (1999); Linden, A., et al., Eur Respir J, 15(5):973-7 (2000); and Aggarwal, S. and Gurney, A. L., J Leukoc Biol. 71(1):1-8 (2002)). IL-17 also synergizes with other cytokines including TNF-α and IL-1β to further induce chemokine expression (Chabaud, M., et al., J. Immunol. 161(1):409-14 (1998)). IL-17A exhibits pleitropic biological activities on various types of cells. IL-17A also has the ability to induce ICAM-1 surface expression, proliferation of T cells, and growth and differentiation of CD34$^+$ human progenitors into neutrophils. IL-17A has also been implicated in bone metabolism, and has been suggested to play an important role in pathological conditions characterized by the presence of activated T cells and TNF-α production such as rheumatoid arthritis and loosening of bone implants (Van Bezooijen et al., J. Bone Miner. Res., 14: 1513-1521 (1999)).

Interleukin 17A has been recognized as the prototype member of an emerging family of cytokines. The large scale sequencing of the human and other vertebrate genomes has revealed the presence of additional genes encoding proteins clearly related to IL-17A, thus defining a new family of cytokines. There are at least 6 members of the IL-17 family in humans and mice including IL-17A, IL-17B, IL-17C, IL-17D, IL-17E and IL-17F (see WO01/46420 published Jun. 28, 2001). Both IL-17A and IL-17F are secreted as disulphide linked homodimers ("IL-17AA" and "IL-17FF," respectively). In addition, a heterodimeric species consisting of disulphide-linked IL-17A and IL-17F has also been identified ("IL-17A/F"). Initial characterization suggests that, like IL-17A, several of these newly identified IL-17 molecules have the ability to modulate immune function. The potent inflammatory actions that have been identified for several of these factors and the emerging associations with major human diseases suggest that these proteins may have significant roles in inflammatory processes and may offer opportunities for therapeutic intervention.

The gene encoding human IL-17F is located adjacent to IL-17A (Hymowitz, S. G., et al., Embo J, 20(19):5332-41 (2001)). IL-17A and IL-17F share about 44% amino acid identity whereas the other members of the IL-17 family share a more limited 15-27% amino acid identity suggesting that IL-17A and IL-17F form a distinct subgroup within the IL-17 family (Starnes, T., et al., J Immunol. 167(8):4137-40 (2001); Aggarwal, S. and Gurney, A. L., J. Leukoc Biol, 71(1):1-8 (2002)). IL-17F appears to have similar biological actions as IL-17A, and is able to promote the production of IL-6, IL-8, and G-CSF from a wide variety of cells. Similarly to IL-17A, it is able to induce cartilage matrix release and inhibit new cartilage matrix synthesis (see U.S. 2002-0177188-A1 published Nov. 28, 2002). Thus, like IL-17A, IL-17F may potentially contribute to the pathology of inflammatory disorders. It has been reported that both IL-17A and IL-17F are induced in T cells by the action of interleukin 23 (IL-23) (Aggarwal, S., et al., J. Biol. Chem., 278(3):1910-4 (2003)). More specifically, both IL-17A and IL-17F have been implicated as contributing agents to progression and pathology of a variety of inflammatory and autoimmune diseases in humans and mouse models of human diseases. If fact, IL-17A, and to a lesser extent, IL-17F, have been implicated as effector cytokines that trigger inflammatory responses and thereby contribute to a number of autoinflammatory (autoimmune) diseases, including multiple sclerosis (MS) (Matusevicius et al., Mult. Scler., 5: 101-104 (1999); Kurasawa, K., et al., Arthritis Rheu 43(11):2455-63 (2000)).

The amino acid sequence of the human receptor for IL-17A, IL-17RA, is available under NCBI GenBank Accession No. NP_055154.3. To date, at least four additional receptors have been identified in the IL-17R family based on sequence homology to IL-17RA (IL-17RB, IL-17RC, IL-17RD, and IL-17RE) and among them, IL-17RC has been shown to physically associate with IL-17RA, suggesting that it may be a functional component in the IL-17R complex (Toy, D. et al., J. Immunol. 177: 36-39 (2006)). It has been reported that IL-17RC is a receptor for both IL-17A and IL-17F (Presnell, et al., J. Immunol. 179(8):5462-73 (2007)).

SUMMARY OF THE INVENTION

In one aspect, the present invention provides a method of identifying a mammalian subject having or at risk of developing multiple sclerosis (MS), comprising measuring, in a biological sample obtained from said subject, the expression level of one or more genes selected from the group TIMP1, LRG1, CXCL1, CXCL5, CXCL10, IL-8, NFκBIZ, YKL40, and G-CSF; wherein an increased level of expression relative to a control indicates that the subject has or is at risk of developing multiple sclerosis.

In another aspect, the present invention provides a method of identifying or predicting a mammalian subject having multiple sclerosis (MS) or at risk of developing MS, who is likely to be responsive to treatment with an IL-17 antagonist, comprising measuring, in a biological sample obtained from said subject, the expression level of one or more genes selected from the group TIMP1, LRG1, CXCL1, CXCL5, CXCL10, IL-8, NFκBIZ, YKL40, and G-CSF; and determining that the subject is likely to be responsive to treatment if the expression level of the one or more genes is increased relative to a control.

In another aspect, the present invention provides a method of identifying or predicting a mammalian subject having multiple sclerosis (MS) or at risk of developing MS, who is less likely to be responsive to treatment with an IL-17 antagonist, comprising measuring, in a biological sample obtained from said subject, the expression level of one or more genes selected from the group TIMP1, LRG1, CXCL1, CXCL5, CXCL10, IL-8, NFκBIZ, YKL40, and G-CSF; and determining that the subject is less likely to be responsive to treatment if the expression level of the one or more genes is decreased or at the same level relative to a control.

In a further aspect, the present invention provides a method of monitoring a mammalian subject with multiple sclerosis (MS) being treated with an IL-17 antagonist, comprising measuring, in a biological sample obtained from said subject, the expression level of one or more genes selected from the group TIMP1, LRG1, CXCL1, CXCL5, CXCL10, IL-8, NFκBIZ, YKL40, and G-CSF, and determining whether the expression level of the one or more genes is increased relative to a control. In an embodiment of the invention, an increased level of expression relative to a control indicates that treatment with the IL-17 antagonist is to be continued.

In another aspect, the present invention also provides a method of treating a mammalian subject having or at risk of developing multiple sclerosis (MS), comprising measuring, in a biological sample obtained from said subject, the expression level of one or more genes selected from the group TIMP1, LRG1, CXCL1, CXCL5, CXCL10, IL-8, NFκBIZ, YKL40, and G-CSF; and administering to the subject having an increased expression level of said one or more genes, relative to a control, an effective amount of an IL-17 antagonist.

In a further aspect, the present invention provides a method of detecting in a mammalian subject suspected of having relapsing-remitting multiple sclerosis (RRMS) or at risk of developing RRMS an expression level of one or more genes, comprising obtaining a biological sample from the subject; and measuring in the biological sample the expression level of one or more genes selected from the group TIMP1, LRG1, CXCL1, CXCL5, CXCL10, IL-8, NFκBIZ, YKL40, and G-CSF. In an embodiment of the invention, the method further comprises determining that the subject has or is at risk of developing RRMS if the expression level is increased relative to a control.

In an embodiment of any aspect of the present invention, the mammalian subject is a human patient. In another embodiment, the multiple sclerosis is characterized by an increased level of IL-17. In a particular embodiment, the level of IL-17 is elevated in the cerebrospinal fluid (CSF) of the subject. In a further embodiment, the multiple sclerosis is relapsing-remitting multiple sclerosis (RRMS). In yet another embodiment, the IL-17 is IL-17AA. In a further embodiment, the expression level of the RNA transcript of one or more genes is measured, and in another embodiment, the expression level of the protein product of one or more genes is measured.

In another embodiment of any aspect of the present invention, the biological sample is a biological fluid. In one embodiment, the biological fluid is cerebrospinal fluid (CSF). In another embodiment, the biological fluid is serum, and in yet another embodiment, the biological fluid is plasma.

In yet another embodiment of any aspect of the present invention, the expression level of TIMP1 is measured. In another embodiment, the expression level of LRG1 is measured. In yet another embodiment, the expression level of the RNA transcript of NFκBIZ is measured. In an embodiment of the invention, the expression level of G-CSF is measured in the serum. In another embodiment, the expression level of one or more genes selected from the group CXCL1, CXCL5, and CXCL10, is measured in the plasma. In a further embodiment, the expression levels of two or more of said genes are measured, and in another embodiment, the expression levels of three or more of said genes are measured.

In another embodiment of any aspect of the present invention, the expression levels of TIMP1 and at least one or more genes selected from the group LRG1, CXCL1, CXCL5, CXCL10, IL-8, NFκBIZ, YKL40, and G-CSF are measured. In a further embodiment, the expression levels of LRG1 and at least one or more genes selected from the group TIMP1, CXCL1, CXCL5, CXCL10, IL-8, NFκBIZ, YKL40, and G-CSF are measured. In a particular embodiment, the expression levels of TIMP1 and LRG1 are measured. In another embodiment, the expression levels of TIMP1 and LRG1 are measured in the CSF. In a further embodiment, the expression levels of TIMP1 and/or LRG1 and G-CSF are measured. In yet another embodiment, the expression levels of TIMP1 and/or LRG1 are measured in the CSF and the expression level of G-CSF is measured in serum. In another embodiment, the expression levels of TIMP1, LRG1, and G-CSF are measured.

In another embodiment of any aspect of the present invention, the methods of the invention further comprise administering to the subject identified as having MS, predicted to having MS, or at risk of developing MS an effective amount of an IL-17 antagonist. In a particular embodiment of any aspect of the present invention, the methods of the invention comprise further administering an effective amount of an IL-17 antagonist to a subject determined to have an increased level of expression of one or more of the disclosed genes relative to a control. In an embodiment of the invention, the IL-17 antagonist is an antibody or an antigen-binding fragment thereof. In a particular embodiment, the antibody is an IL-17 antibody or an IL-17 receptor antibody. In an embodiment, the antibody is at least one antibody selected from the group brodalumab, secukinumab, ixekizumab, bimekizumab, CNTO 6785, ALX-0761, and afasevikumab. In a further embodiment, the antibody is an IL-17 antibody and the IL-17 antibody binds to an IL-17A homodimer, IL-17F homodimer, and/or IL-17AF heterodimer. In an embodiment, the antibody is an IL-17 antibody that binds to IL-17A homodimer. In another embodiment, the IL-17 antibody binds to IL-17AA and IL-17AF. In yet another embodiment, the antibody is an IL-17 antibody that binds to IL-17F homodimer. In a further embodiment, the antibody is an IL-17 antibody that binds IL-17A/F heterodimer. In another embodiment, the antibody is a monoclonal antibody. In yet another embodiment, the antibody is a chimeric, humanized, or human antibody. In a yet further embodiment, the antibody is a bispecific, multi specific, or cross-reactive antibody.

In yet another embodiment of any aspect of the present invention, the methods of the invention further comprises administering an effective amount of a multiple sclerosis (MS)-treating agent. In an embodiment of the invention, the MS-treating agent is at least one agent selected from the group dimethyl fumarate, FTY-720, natalizumab, corticosteroids, β-interferon, glatiramer acetate, teriflunomide, mitoxantrone, and anti-CD20 antibody.

In another aspect, the present invention provides a kit for detecting an expression level of one or more genes in a mammalian subject having or is at risk of developing multiple sclerosis (MS), comprising at least one container comprising one or more reagents for detecting the expression level of one or more genes selected from the group TIMP1, LRG1, CXCL1, CXCL5, CXCL10, IL-8, NFκBIZ, YKL40, and G-CSF. In an embodiment of the invention, the one or more reagents comprise reagents for detecting the expression level of the RNA transcript and/or the expression level of the protein product of the one or more genes. In another embodiment, the reagents comprise one or more gene specific primers or probes of the one or more genes. In a further embodiment, the one or more reagents comprise reagents for detecting the expression level of the protein product of the one or more genes. In yet another embodiment, the reagents comprise one or more antibodies, or antigen-binding fragments thereof, that bind the protein product of the one or more genes. The kits of the present invention may further comprise a container comprising an IL-17 antagonist and a label or instructions for administering said IL-17 antagonist to said subject. In an embodiment, the IL-17 antagonist is an antibody, or an antigen-binding fragment thereof. In another embodiment, the antibody is an IL-17 antibody or an IL-17 receptor antibody. In a further embodiment, the antibody is an IL-17 antibody that binds to an IL-17A homodimer, IL-17F homodimer, and/or IL-17AF heterodimer. In various embodiments of the invention, MS is relapsing-remitting MS (RRMS).

BRIEF DESCRIPTION OF THE DRAWINGS

FIG. 1A-1B show (A) a nucleotide sequence (SEQ ID NO:1) of a native human IL-17A cDNA and (B) the amino acid sequence (SEQ ID NO:2) of native human IL-17A derived from the coding sequence of SEQ ID NO:1 shown in FIG. 1A. The signal peptide is underlined.

FIG. 2A-2B show (A) a nucleotide sequence (SEQ ID NO:3) of a native human IL-17F cDNA and (B) the amino acid sequence (SEQ ID NO:4) of native human IL-17F derived from the coding sequence of SEQ ID NO:3 shown in FIG. 2A. The signal peptide is underlined.

FIG. 3A-3E show (A-D) a nucleotide sequence (SEQ ID NO:5) of a native human IL-17RA cDNA and (E) the amino acid sequence (SEQ ID NO:6) of native IL-17RA derived from the coding sequence of SEQ ID NO:4 shown in FIGS. 3A-3C.

FIG. 4A-4B show (A) a nucleotide sequence (SEQ ID NO:7) of a native human IL-17RC cDNA and (B) the amino acid sequence (SEQ ID NO:8) of native human IL-17RC derived from the coding sequence of SEQ ID NO:8 shown in FIG. 4A.

DETAILED DESCRIPTION

Definitions

Figure 5:
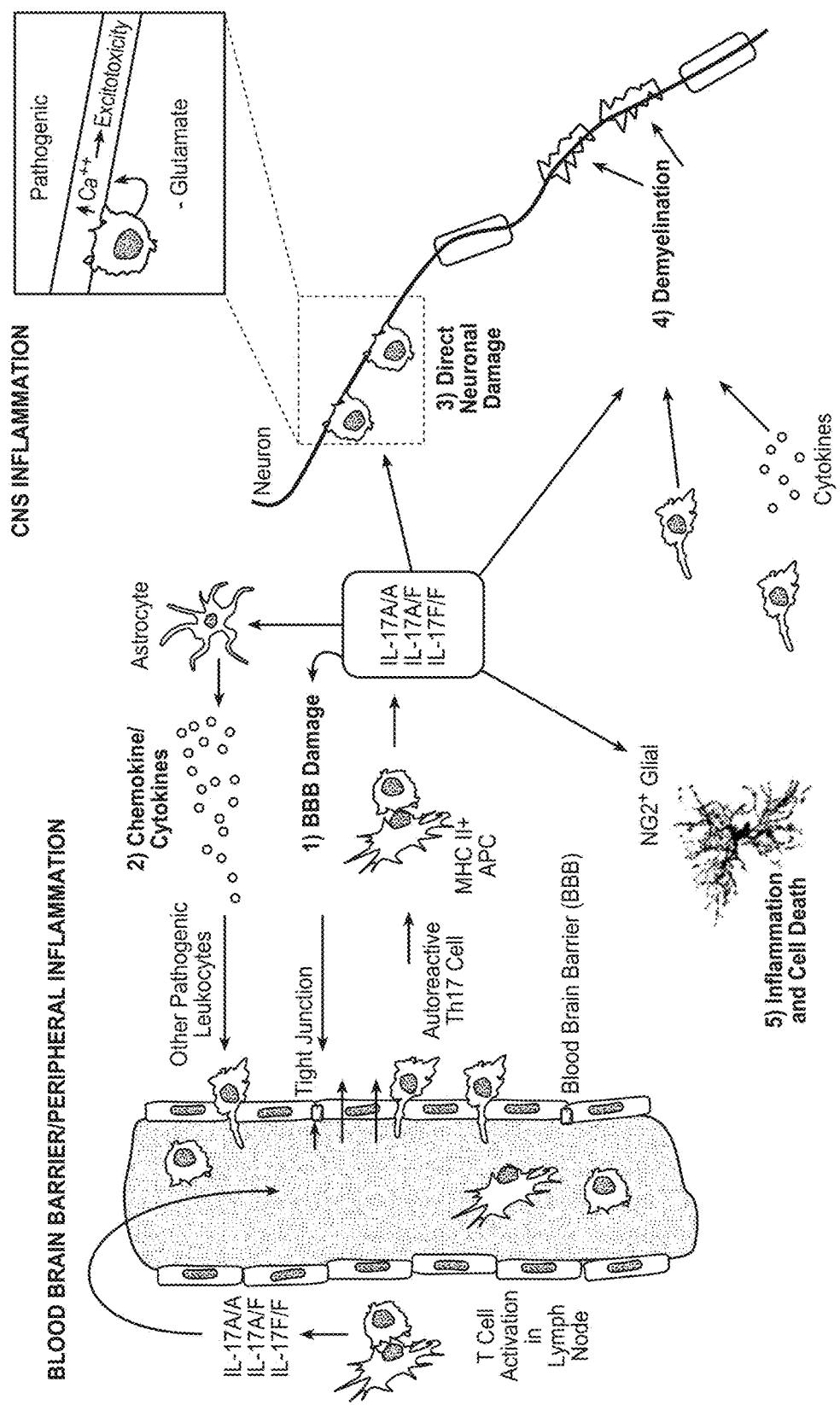
FIG. 5 shows the possible role of the IL-17 pathway in the pathogenesis of MS.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "IL-17" is used herein to refer to IL-17A and/or IL-17F, unless otherwise indicated, as well as their homodimers and heterodimers, and refers to any native IL-17 from any vertebrate source, including mammals such as primates (e.g. humans) and rodents (e.g., mice and rats), unless otherwise indicated. The term encompasses full-length, unprocessed IL-17, as well as any form of IL-17 that results from processing in the cell, including the precursor form and the mature form of the protein. The term also encompasses naturally occurring variants of IL-17, e.g., splice variants or allelic variants. Both IL-17A and IL-17F are secreted as disulfide linked homodimers ("IL-17AA" and "IL-17FF," respectively), in addition to a heterodimeric species consisting of disulfide-linked IL-17A and IL-17F ("IL-17A/F"). Thus, the term also encompasses the homodimers and heterodimers of IL-17. "IL-17AA" as used herein refers to the IL-17A homodimer, and "IL-17FF" refers to the IL-17F homodimer. "IL-17A/F" or "IL-17AF" refers to the IL-17A and IL-17F heterodimer. "IL-17A" as used herein refers to the IL-17A homodimer (IL-17AA) unless specified otherwise, and "IL-17F" refers to the IL-17F homodimer (IL-17FF) unless otherwise specified. In an embodiment of the invention, IL-17 is IL17-AA. In another embodiment of the invention, IL-17 is IL-17FF. In yet another embodiment, IL-17 is IL-17A/F. Full-length polypeptide chains of human IL-17A and IL-17F comprising the amino acid sequences are shown in FIGS. 1B and 2B (SEQ ID NOs: 2 and 4), respectively, and their corresponding nucleic acid sequences are shown in FIGS. 1A and 2A (SEQ ID NOs: 1 and 3), respectively. Start and stop codons are shown in bold font and underlined in the figures.

Figure 3A:
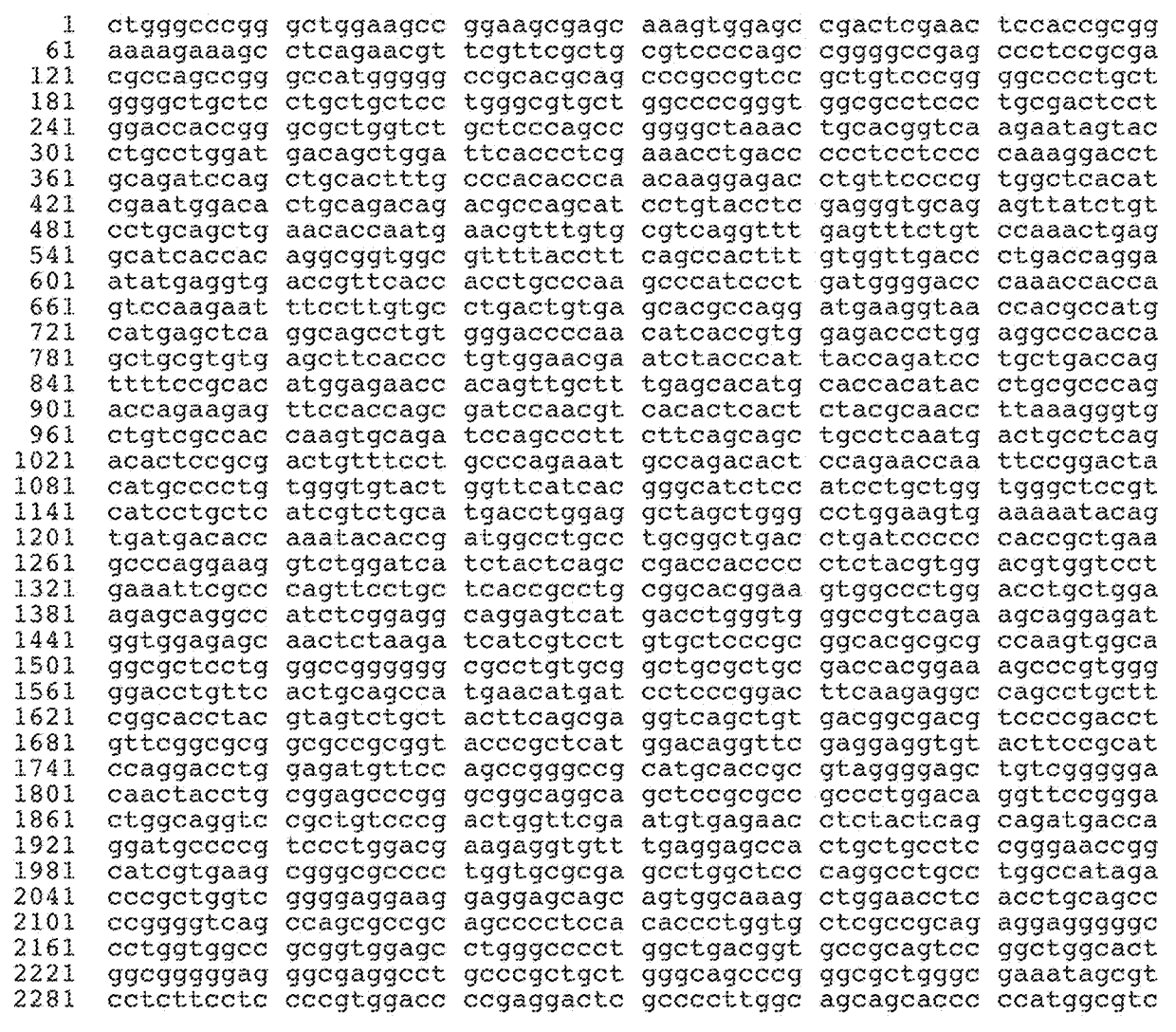
Figure 3B:
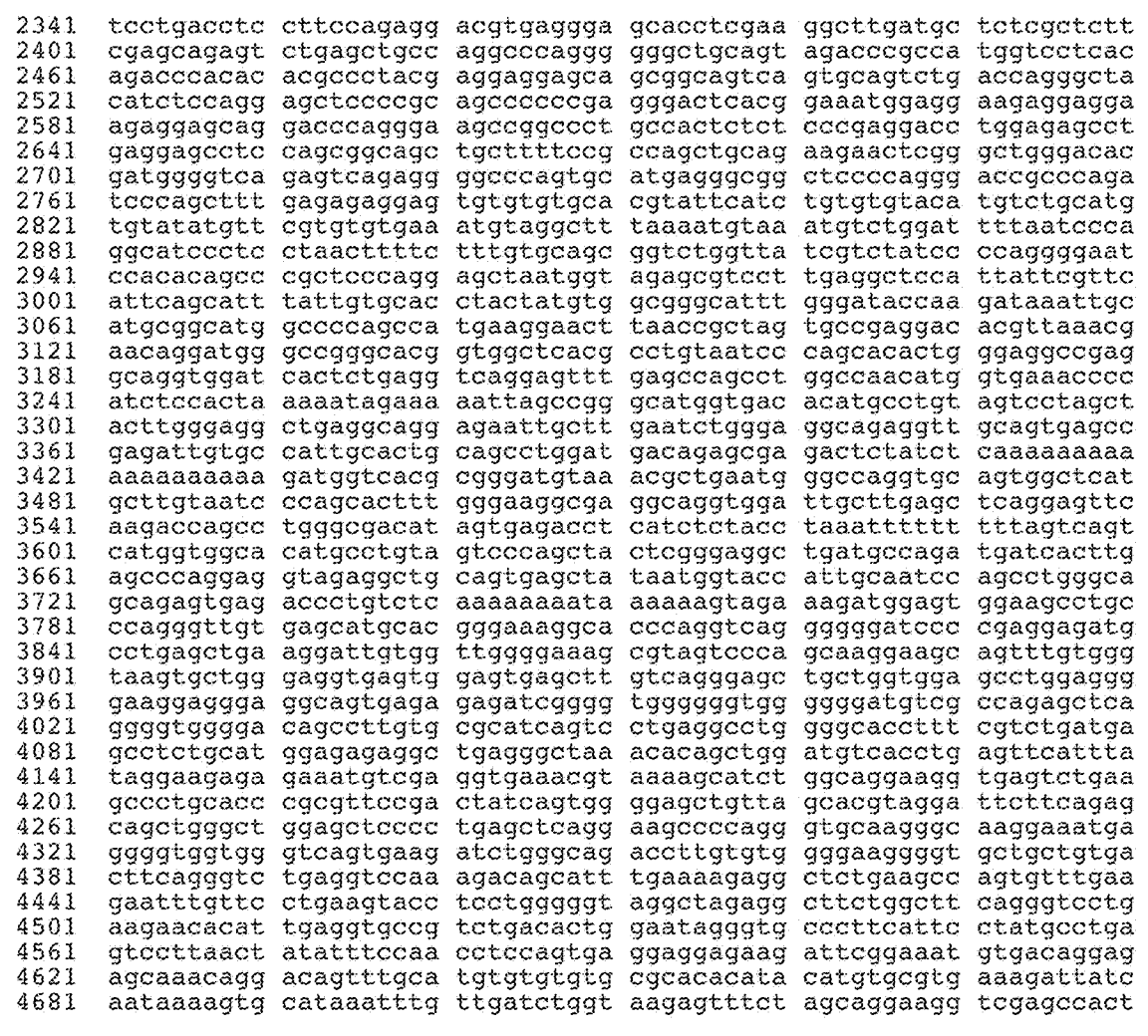

The term "IL-17 receptor" is used to refer generally to members of the IL-17 receptor family, including IL-17RA, IL-17RB, IL-17RC, IL-17RD, and L-17RE, and their complexes, and refers to any native IL-17 receptor from any vertebrate source, including mammals such as primates (e.g. humans) and rodents (e.g., mice and rats), unless otherwise indicated. The term encompasses full-length, unprocessed IL-17 receptor, as well as any form of IL-17 receptor that results from processing in the cell, including mature IL-17 receptor, soluble IL-17 receptors, such as a soluble IL-17RA and/or soluble IL-17RC. The term also encompasses naturally occurring variants of IL-17 receptor, e.g., splice variants or allelic variants. The nucleotide sequence of a native sequence IL-17RA polypeptide is shown in FIGS. 3A-D and its amino acid sequence is shown in FIG. 3E (SEQ ID NOs: 5 and 6), respectively. The nucleotide sequence of a native sequence IL-17RC polypeptide is shown in FIG. 4A and its amino acid sequence is shown in FIG. 4B (SEQ ID NOs: 7 and 8), respectively.

An "IL-17 antagonist" as used herein includes any molecule that interferes with the function or binding of IL-17, blocks, and/or neutralizes a relevant activity of IL-17. Thus, an IL-17 antagonist includes an anti-IL-17 antibody, an anti-IL-17 receptor antibody, including an anti-IL-17RA antibody and anti-IL-17RC antibody, or a soluble IL-17 receptor, including a soluble IL-17RA and a soluble IL-17RC.

An "IL-17 antibody," "anti-IL-17 antibody," or "antibody that binds to IL-17" refers to an antibody, or an antigen-binding fragment thereof, that is capable of binding to IL-17A homodimer, IL-17F homodimer, and/or IL-17AF heterodimer, or a portion thereof, with sufficient affinity such that the antibody is useful as a detection, analytical, diagnostic and/or therapeutic agent in targeting IL-17. The IL-17 antibody may further interfere with IL-17 activities. In addition, the IL-17 antibody may interfere with expression of other genes or proteins. In an embodiment, the IL-17 antibody is capable of binding to IL-17AA, IL-17FF, and/or IL-17AF. In some embodiments, an anti-IL17 antibody is capable of binding IL-17A homodimer. In some embodiments, an anti-IL17 antibody is capable of binding IL-17A homodimer and IL-17AF heterodimer. In certain embodiments, an anti-IL-17 antibody is capable of binding to IL-17A homodimer and not capable of binding to IL-17AF heterodimer. In certain embodiments, an anti-IL-17 antibody is capable of binding to IL-17F homodimer and not capable of binding to IL-17AF heterodimer. In some embodiments, an anti-IL-17 antibody is capable of binding IL-17A homodimer, IL-17F homodimer, and IL-17AF heterodimer. In some such embodiments, an anti-IL-17 antibody that is capable of binding IL-17A homodimer, IL-17F homodimer, and IL-17AF heterodimer can also be referred to as an IL-17A and F antibody or IL-17A and IL-17F cross-reactive antibody or IL-17A/F cross-reactive antibody. In certain such embodiments, the IL-17A and F cross-reactive antibody binds to identical or similar epitopes on IL-17A, IL-17F and/or IL-17AF heterodimer. In certain embodiments, the IL-17A and F cross-reactive antibody binds to identical or similar epitopes on IL-17A, IL-17F and/or IL-17AF heterodimer with sufficient affinity. In certain advantageous embodiments, the IL-17A and F cross-reactive antibody binds to IL-17A, IL-17F and IL-17AF with high affinity. The structures of IL-17A and IL-17F have been reported. See Hymowitz et al., 2001, *Embo J*, 20(19):5332-41, Ely et al., 2009, *Nature Immunology* 10(12):1245-1252, and Liu et al., 2013, *Nature Communications* DOI: 10.1038/ncomms2880. Similar or identical epitopes comprising amino acid resides present in the surface area of IL-17A and IL-17F can be deduced from the structures.

An "IL-17 receptor antibody," "anti-IL-17 receptor antibody," or "antibody that binds to IL-17 receptor" refers to an antibody that is capable of binding to an IL-17 receptor, or a portion thereof, with sufficient affinity such that the antibody is useful as a diagnostic and/or therapeutic agent in targeting IL-17 receptor. Additionally, the IL-17 receptor antibody may interfere with IL-17 receptor activities, such as downstream signaling. The IL-17 receptor antibody may also interfere with expression of other genes or proteins. In an embodiment, the IL-17 receptor antibody is capable of binding to IL-17RA and/or IL-17RC. In other embodiments, the IL-17 receptor antibody is capable of binding to IL-17RA. In some other embodiments, the IL-17 receptor antibody is capable of binding to IL-17RC. In certain embodiments, the IL-17 receptor antibody is capable of binding to IL-17RA and IL-17RC.

An antibody, oligopeptide or other organic molecule that "binds" an antigen of interest, e.g. an IL-17 antibody that binds to IL-17A homodimer, IL-17F homodimer, and/or IL-17AF heterodimer, is one that binds the antigen with sufficient affinity such that the antibody, oligopeptide or other organic molecule does not bind other unrelated proteins non-specifically. In one embodiment, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis, radioimmunoprecipitation (RIA), or other means. In certain embodiments, an antibody that binds to IL-17 or IL-17 receptor has a dissociation constant (Kd) of at least about $10^{-4}$M, alternatively at least about $10^{-5}$M, alternatively at least about $10^{-6}$M, alternatively at least about $10^{-7}$M, alternatively at least about $10^{-8}$M, alternatively at least about $10^{-9}$M, alternatively at least about $10^{-10}$ M, alternatively at least about $10^{-11}$M, alternatively at least about $10^{-12}$ M, or greater.

The term "antibody" herein is used in the broadest sense and specifically covers monoclonal antibodies, polyclonal antibodies, multispecific antibodies (e.g. bispecific antibodies), and antigen-binding fragments, so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., *Nature*, 352:624-628 (1991); Marks et al., *J. Mol. Biol.*, 222:581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569, 825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

An "intact antibody" as used herein is one which comprises two antigen binding regions, and an Fc region. Preferably, the intact antibody has a functional Fc region.

"Antigen-binding fragments" comprise a portion of an intact antibody comprising the antigen binding region thereof. Examples of antigen-binding fragments include Fab, Fab', F(ab')$_2$, and Fv fragments; diabodies; linear antibodies; single-chain antibody molecules; and multispecific antibodies formed from antibody fragment(s).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

The term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)), and regulates homeostasis of immunoglobulins.

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies,* vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A "naked antibody" is an antibody that is not conjugated to a heterologous molecule, such as a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g. deamidated antibody variant), a basic variant, an antibody with an amino-terminal leader extension (e.g. VHS-) on one or two light chains thereof, an antibody with a C-terminal lysine residue on one or two heavy chains thereof, etc., and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moieties attached thereto which differ from one or more carbohydrate moieties attached to a main species antibody.

Where the antibody has an Fc region, an oligosaccharide structure may be attached to one or two heavy chains of the antibody, e.g. at residue 299 (298, Eu numbering of residues).

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

A "deamidated" antibody is one in which one or more asparagine residues thereof has been derivatized, e.g. to an aspartic acid, a succinimide, or an iso-aspartic acid.

As used herein, the term "expression level" as applied to a gene refers to the level of a gene product, e.g. the value determined for the level of an RNA transcript of the gene or for the level of a protein product of the gene.

The terms "down-regulated," "decreased," and "reduced" are used interchangeably and mean that the expression, activity, or level of a gene, or RNA transcripts or protein products of the gene, is less than relative to one or more controls, such as, for example, one or more positive and/or negative controls.

The term "up-regulated," "increased," or "elevated" is used to mean that the expression, activity, or level of a gene, or RNA transcripts or protein products of the gene, is greater than relative to one or more controls, such as, for example, one or more positive and/or negative controls.

A "subject" includes a mammalian and a human subject. A mammal includes, but is not limited to, humans, rodents, sport, zoo, pet and domestic or farm animals such as dogs, cats, cattle, sheep, pigs, horses, and non-human primates, such as monkeys. Preferably the rodents are mice or rats. Preferably, the mammal is a human, also called herein a patient.

"Treatment" refers to the management and care of a subject for the purpose of combating any of the diseases or conditions targeted in accordance with the present invention, including, without limitation, multiple sclerosis, and in particular, relapsing-remitting multiple sclerosis (RRMS). Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, IL-17 antagonists of the invention are used to delay development of a disease or to slow the progression of a disease.

"Multiple sclerosis" or "MS" is also known as disseminated sclerosis or encephalomyelitis disseminata, an inflammatory disease in which the insulating covers of nerve cells in the brain and spinal cord are damaged or demyelinated. MS is categorized into four general types, including relapsing-remitting (RRMS), secondary progressive (SPMS), primary progressive (PPMS), and progressive relapsing MS. RRMS is characterized by unpredictable relapses followed by periods of months to years of remission with no new signs of disease activity, and is the initial course of a majority of individuals with MS. Those with RRMS may later develop SPMS and experience progressive neurologic decline between acute attacks without any definite periods of remission. PPMS is characterized by progression of disability from onset, with no, or only occasional and minor, remissions and improvements. Progressive relapsing MS is the most uncommon type and is characterized by a steady neurologic decline from onset and clear superimposed attacks. See Lublin et al., Neurology 83:278-286 (2014).

"Multiple sclerosis (MS)-treating agent" refers to an agent other than an IL-17 antagonist that is used to treat MS, such as, for example, dimethyl fumarate (TECFIDERA®), FTY-720 (fingolimod, GILENYA®), nataluzimab (TYSABRI®), corticosteroids, β-interferons, glatiramer acetate (COPAXONE®), teriflunomide (AUBAGIO®), mitoxantrone, and anti-CD20 antibody, such as ocrelizumab, rituximab, and ofatumumab.

The term "effective amount" refers to an amount of a drug, such as an IL-17 antagonist, effective to treat multiple sclerosis in the patient.

In the context of the present invention, reference to "at least one," "at least two," "at least three," "at least four," "at least five," etc. of the genes listed in any particular gene set means any one or any and all combinations of the genes listed.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Multiple sclerosis (MS) is a demyelinating inflammatory disorder of the central nervous system (CNS), which involves autoimmune responses to myelin antigens. Studies in experimental autoimmune encephalomyelitis (EAE), an animal model for MS, have provided evidence that T cells specific for self-antigens mediate pathology in these diseases. Until recently, T helper type 1 (Th1) cells were thought to be the main effector T cells responsible for the autoimmune inflammation. However, more recent studies suggest a pathogenic role for CD4$^+$ T cells that secrete IL-17, termed Th17. See FIG. 5. It is thought that the activated myelin-specific T cells enter the bloodstream and enter the central nervous system (CNS). Breakdown of the blood-brain barrier (BBB) occurs, allowing recruitment of other inflammatory cells into the CNS. T cells entering the CNS encounter their cognate myelin antigens and become reactivated by local APC. T cells expand and release inflammatory mediators which help recruit other immune cells to the site of inflammation. Activation of local microglial cells and infiltrating cells results in production of proteases, glutamate, reactive oxygen species and other cytotoxic agents which promote inflammation, cell death, direct neuronal damage, and demyelination. Damage to the myelin sheath surrounding axons is followed by axonal damage and neurological impairment.

The present invention is based, at least in part, on the finding that IL-17, in particular, IL-17AA, was found to be elevated in the cerebrospinal fluid (CSF) of a subset of multiple sclerosis patients, particularly in patients with relapsing-remitting MS (RRMS). Accordingly, the expression level of IL-17, in particular, IL-17AA, in MS patients may serve as a biomarker for identifying patients with MS, at risk of developing MS, and who are likely to be responsive to treatment with an IL-17 antagonist, such as IL-17 antibodies. These patients may also benefit from novel combination treatments of an IL-17 antagonist in combination with other multiple sclerosis-treating agents.

Surrogate markers, the expression of which are positively or negatively coordinately regulated with the expression of IL-17, in particular, IL-17AA, are also suitable as biomarkers of MS. Surrogate markers include genes that are positive regulators of the same pathway as the pathway positively regulated by IL-17, in particular, IL-17AA, or a downstream pathway. The increased expression of such genes relative to a control can identify patients who have MS, at risk of developing MS, and/or who are likely to be responsive to treatment with an IL-17 antagonist, such as an IL-17 antibody. Surrogate markers also include genes the expression of which inversely correlates with the expression of IL-17, in particular, IL-17AA. The decreased expression of such genes relative to a control may also identify patients who have MS, at risk of developing MS, and/or who are likely to be responsive to treatment with an IL-17 antagonist, such as an IL-17 antibody. Accordingly, the present invention sought surrogate biomarkers to IL-17, in particular, to IL-17AA.

Surrogate Markers of IL-17AA in Multiple Sclerosis

According to the present invention, the following genes have been identified as being associated with increased levels of IL-17AA in RRMS patients: TIMP1, LRG1, CXCL1, CXCL5, CXCL10, IL8, NFκBIZ, YKL40 (CHI3L1), and G-CSF (CSF3). These genes are also listed in Table 1, which list selected genes analyzed herein, along with their representative NCBI GenBank accession numbers. Increased expression level of the RNA transcript, or its protein product, of one or more of these genes in a biological sample obtained from a subject, relative to control, indicates that the subject may have MS, is at risk of developing MS, and/or may be more likely to be responsive to treatment with an IL-17 antagonist, such as IL-17 antibodies. Decreased expression level relative to a control, or the same level relative to a control, of one or more of the disclosed genes indicates that the subject may not have MS, is not at risk of developing MS, and/or may be less likely to be responsive to treatment with an IL-17 antagonist.

The control may, for example, be the expression of a gene, present in the same cell, which is known to be up-regulated in patients in multiple sclerosis (positive control). Alternatively, or in addition, the control can be the expression of the same gene as the marker gene in a normal cell of the same cell type (negative control). Expression levels can also be normalized, for example, to the expression levels of housekeeping genes, such as glyceraldehyde-3-phosphate-dehydrogenase (GAPDH) and/or β-actin, or to the expression levels of all genes in the sample tested. The control value can be a predetermined, average value obtained from a relevant general population. These and other controls and methods are well known in the art, and are apparent to those skilled in the art.

The genes disclosed have been surprisingly found to be associated with increased levels of IL-17AA in RRMS patients. TIMP1, for example, is a well-recognized endogenous regulator of the matrix metalloproteinase (MMP) family of extracellular proteases but its role in myelin pathology is still unclear as TIMP1 appears to exhibit both positive and negative effects in CNS myelin injury. Some report that TIMP1 plays a protective role in inhibiting MMP-mediated pathogenesis by promoting remyelination in response to CNS myelin injury (see e.g., Ichiyama et al., J. Neuroimmunology 172:182-186, 2006; Moore et al., J. Neuroscience 31:6247-6254, 2011) while others have suggested that TIMP1 secreted by T cells promotes neuropathology (see e.g. Adamson et al., PLoS ONE 8:e59367. doi:10.1371/journal.pone.0059367, 2013). LRG1 is a protein shown to be involved in protein-protein interaction, signal transduction, and cell adhesion and development and is produced by inflammation (see e.g., Wang et al., Nature 499:306-311, 2013; Miyajima et al., PLoS ONE 8:e74453.doi:10.1371/journal.pone.0074453, 2013). While LRG1 has been associated with Parkinson's disease with demential (PDD) and progressive supranuclear palsy (PSP) (see e.g. Miyajima supra), there are no known reports of an association between LRG1 and multiple sclerosis, in particular, RRMS.

fluid, or derivatives such as blood serum and blood plasma, and the like. In one aspect, the expression level measured is the expression level of the RNA transcript of the gene. In another aspect, the expression level measured is the expression level of the protein product of the gene. The expression levels of the RNA transcripts or the protein products of one, two, three, four, or five, six, seven, eight, or more genes may be measured. In an embodiment of the invention, the expression level of the RNA transcript of TIMP1, or its protein product, may be measured. In a particular embodiment, the expression level of the RNA transcript of TIMP1, or its protein product, and at least one or more genes selected from the group LRG1, CXCL1, CXCL5, CXCL10, IL8, NFκBIZ, YKL40, and G-CSF, may be measured. In another embodiment, the expression level of the RNA transcript of LRG1, or its protein product, may be measured. In another particular embodiment, the expression level of the RNA transcript

TABLE 1

| Gene | Name | Exemplary Accession No. and sequences |
|---|---|---|
| IL-17A | Interleukin 17A | NP_002181 |
| IL-17F | Interleukin 17F | NM_052872 |
| IL-17RA | Interleukin 17 receptor A | NP_005154.3 |
| IL-17RC | Interleukin 17 receptor C | AY359098 |
| TIMP1 | Tissue inhibitor of metalloproteinase 1 | NM_003254 |
| LRG1 | Leucine-rich alpha-2-glycoprotein 1 | NM-052972.2 |
| CXCL1 | Chemokine (C—X—C motif) ligand 1 | NM_001511.3 |
| CXCL5 | Chemokine (C—X—C motif) ligand 5 | NM_002994.3 |
| CXCL10 | Chemokine (C—X—C motif) ligand 10 | NM_001565.3 |
| IL8 | Interleukin 8 | AF385628.2 |
| NFκBIZ | Nuclear factor of kappa light polypeptide gene enhancer in B-cells inhibitor, zeta | NM_031419.3 |
| YKL40 (CHI3L1) | Chitinase 3-like 1 | NM_001276.2 |
| G-CSF (CSF3) | Colony stimulating factor 3 | NM_000759.3 |
| TARC (CCL17) | Chemokine (C-C motif) ligand 17 | NM_002987.2 |
| MCP4 (CCL13) | Chemokine (C-C motif) ligand 13 | NM_005408.2 |
| IL-6 | Interleukin 6 | NM_000600.3 |
| CD4 | CD4 molecule | NM_000616.4 |
| CD45 (PTPRC) | Protein tyrosine phosphatase, receptor type, C | NM_002838.4 |
| Mobp | Myelin-associated oligodendrocytic basic protein | NM_001278322.1 |
| Mog | Myelin oligodendrocyte glycoprotein | NM_206809.3/NM_002433.4 |
| Eotaxin (CCL11) | Chemokine (C-C motif) ligand 11 | NM_002986.2 |

Diagnosis and Prognosis

In various aspects, the invention provides a method of identifying subjects with MS, at risk of developing MS, and/or likely to be responsive to treatment with an IL-17 antagonist. The method includes the step of measuring the expression level of one or more genes selected from the group TIMP1, LRG1, CXCL1, CXCL5, CXCL10, IL8, NFκBIZ, YKL40 (CHI3L1), and G-CSF (CSF3) in a biological sample obtained from the subject. The method may further include comparing the level of expression of the gene(s) to the level of expression of a control gene. An increased level of expression relative to the control indicates that the subject has MS, is at risk of developing MS, and/or is likely to be responsive to treatment with an IL-17 antagonist. Alternatively, decreased level of expression, or the same level of expression, relative to the control indicates that the subject does not have MS, is not at risk of developing MS, and/or is less likely to be responsive to treatment with an IL-17 antagonist.

The biological sample may be, for example, a biopsy tissue sample or a biological fluid, including, without limitation, cerebrospinal fluid (CSF), blood, urine, saliva, ascites of LRG1, or its protein product, and at least one or more genes selected from the group TIMP1, CXCL1, CXCL5, CXCL10, IL8, NFκBIZ, YKL40, and G-CSF, may be measured. In yet another embodiment, the expression levels of the RNA transcripts of TIMP1 and LRG1, or their protein products, are measured. In a further embodiment, the expression levels of the RNA transcripts of TIMP1 and/or LRG1, and G-CSF, or their protein products are measured. In a particular embodiment, the expression levels of the RNA transcripts of TIMP1, LRG1, and G-CSF, or their protein products, are measured. In a further embodiment, when the method includes measuring the expression level of any one of the genes selected from the group TIMP1, LRG1, CXCL1, CXCL5, CXCL10, IL8, YKL40, and G-CSF, its protein product is measured. When the method includes measuring the expression level of NFκBIZ, its RNA transcript is measured.

In one embodiment, the expression level of one or more of the genes selected from the group TIMP1, LRG1, CXCL1, CXCL5, CXCL10, IL8, NFκBIZ, YKL40, and G-CSF may be measured from the CSF obtained from an MS patient. In a particular embodiment, when the method includes measuring the expression level of one or more genes selected from CXCL1, CXCL5, and CXCL10, its RNA transcript or protein product may be measured from blood plasma obtained from an MS patient. In another embodiment, when the method includes measuring the expression level of G-CSF, its RNA transcript or protein product may be measured from the blood serum obtained from an MS patient. In a particular embodiment, the expression level of the protein product of G-CSF is measured from the blood serum.

In any of the methods and embodiments, MS may be RRMS.

Methods for Measuring Expression Levels

Various methods for determining the expression level of an RNA transcript (eg. mRNA) or protein include, but are not limited to, gene expression profiling, polymerase chain reaction (PCR) including quantitative real time PCR (qRT-PCR), microarray analysis that can be performed by commercially available equipment, following manufacturer's protocols, such as by using the Affymetrix GenChip technology, serial analysis of gene expression (SAGE) (Velculescu et al., *Science* 270:484-487 (1995); and Velculescu et al., *Cell* 88:243-51 (1997)), MassARRAY, Gene Expression Analysis by Massively Parallel Signature Sequencing (MPSS) (Brenner et al., *Nature Biotechnology* 18:630-634 (2000)), proteomics, immunohistochemistry (IHC), etc. In an embodiment of the invention, mRNA is quantified. In a further embodiment, such mRNA analysis is performed using the technique of polymerase chain reaction (PCR), or by microarray analysis. Where PCR is employed, a preferred form of PCR is quantitative real time PCR (qRT-PCR).

General methods for mRNA extraction are well known in the art and are disclosed in standard textbooks of molecular biology, including Ausubel et al., *Current Protocols of Molecular Biology*, John Wiley and Sons (1997). RNA isolation may be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA may also be isolated, for example, by cesium chloride density gradient centrifugation. After analysis of the RNA concentration, RNA repair and/or amplification steps may be included, if necessary, and RNA is reverse transcribed using gene specific promoters followed by PCR. Preferably, real time PCR is used, which is compatible both with quantitative competitive PCR, where internal competitor for each target sequence is used for normalization, and with quantitative comparative PCR using a normalization gene contained within the sample, or a housekeeping gene for RT-PCR. For further details see, e.g. "PCR: The Polymerase Chain Reaction", Mullis et al., eds., 1994; and Held et al., *Genome Research* 6:986-994 (1996).

Expression levels can also be determined at the protein level, for example, using various types of immunoassays or proteomics techniques.

In immunoassays, the target diagnostic protein marker is detected by using an antibody specifically binding to the markers. The antibody typically will be labeled with a detectable moiety. Numerous labels are available which can be generally grouped into the following categories:

1) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al. (1991) Ed. Wiley-Interscience, New York, N.Y., Pubs. for example and radioactivity can be measured using scintillation counting.

2) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

3) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. (1981) Methods for the Preparation of Enzyme-Antibody Conjugates for use in Enzyme Immunoassay, in *Methods in Enzym.* (ed J. Langone & H. Van Vunakis), Academic press, New York 73:147-166.

Examples of enzyme-substrate combinations include, for example:

a) horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

b) alkaline phosphatase (AP) with para-Nitrophenyl phosphate as chromogenic substrate; and c) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In other versions of immunoassay techniques, the antibody need not be labeled, and the presence thereof can be detected using a labeled antibody which binds to the antibody.

The immunoassays described herein may be in any assay format, including, for example, competitive binding assays, direct and indirect sandwich assays, and immunoprecipitation assays. Zola, *Monoclonal Antibodies: A Manual of Techniques*, pp. 147-158 (CRC Press, Inc. 1987).

Competitive binding assays rely on the ability of a labeled standard to compete with the test sample analyte for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Protein levels can also be detected using proteomics techniques. The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable alternatives or supplements to other methods of gene expression profiling, and can be used, alone or in combination with other methods, to detect the products of the tumor resistance markers of the present invention.

Measurement of biomarker expression levels may be performed by using a software program executed by a suitable processor. Suitable software and processors are well known in the art and are commercially available. The program may be embodied in software stored on a tangible medium such as CD-ROM, a floppy disk, a hard drive, a DVD, or a memory associated with the processor, but persons of ordinary skill in the art will readily appreciate that the entire program or parts thereof could alternatively be executed by a device other than a processor, and/or embodied in firmware and/or dedicated hardware in a well known manner.

Following the measurement of the expression levels of RNA transcripts, or their protein products, of one or more of the genes identified herein, the assay results, findings, diagnoses, predictions, prognoses and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

In a preferred embodiment, a diagnosis, prediction, prognosis and/or treatment recommendation based on the expression level in a test subject of one or more of the biomarkers disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

To facilitate diagnosis and/or treatment recommendation, the reference and/or subject biomarker profiles or expression level of one or more of the biomarkers presented herein of the present invention can be displayed on a display device, contained electronically, or in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history.

Methods of Treatment and Monitoring Treatment

The subjects identified in accordance with the present invention as expressing biomarkers correlating with IL-17, in particular, IL-17AA, are likely to be responsive to treatment with an IL-17 antagonist. Thus, the present invention provides a method of treating a subject with MS or at risk of developing MS by measuring in a biological sample obtained from the subject, the expression level of an RNA transcript, or its protein product, of one or more genes selected from the group TIMP1, LRG1, CXCL1, CXCL5, CXCL10, IL8, NFκBIZ, YKL40 (CHI3L1), and G-CSF (CSF3) as described above. The method may further include comparing the level of expression of the gene(s) to the level of expression of a control gene. A subject with an increased expression level of one of more of the genes, relative to a control, is treated with an effective amount of an IL-17 antagonist.

Additionally, the present invention provides a method for monitoring a subject with MS being treated with an IL-17 antagonist. The method comprises the step of measuring in a biological sample obtained from the subject, the expression level of an RNA transcript, or its protein product, of one or more genes selected from the group TIMP1, LRG1, CXCL1, CXCL5, CXCL10, IL8, NFκBIZ, YKL40 (CHI3L1), and G-CSF (CSF3) as described above, and determining whether the expression level of the one or more genes is increased relative to control. In an embodiment of the invention, an increased level of expression relative to control indicates that treatment with the IL-17 antagonist is to be continued in the subject. An embodiment of the invention provides further administration of the IL-17 antagonist to the subject.

In these methods of the invention, the biological sample used and/or obtained may be, for example, a biological fluid, including, without limitation, cerebrospinal fluid (CSF), blood, urine, saliva, ascites fluid, or derivatives such as blood serum and blood plasma, and the like. In one aspect of the invention, the expression level measured is the expression level of the RNA transcript of the gene. In another aspect, the expression level measured is the expression level of the protein product of the gene. The expression levels of the RNA transcripts or the protein products of one, two, three, four, or five, six, seven, eight, or more genes may be measured. In an embodiment of the invention, the expression level of the RNA transcript of TIMP1, or its protein product, may be measured. In a particular embodiment, the expression level of the RNA transcript of TIMP1, or its protein product, and at least one or more genes selected from the group LRG1, CXCL1, CXCL5, CXCL10, IL8, NFκBIZ, YKL40, and G-CSF, may be measured. In another embodiment, the expression level of the RNA transcript of LRG1, or its protein product, may be measured. In another particular embodiment, the expression level of the RNA transcript of LRG1, or its protein product, and at least one or more genes selected from the group TIMP1, CXCL1, CXCL5, CXCL10, IL8, NFκBIZ, YKL40, and G-CSF, may be measured. In yet another embodiment, the expression levels of the RNA transcripts of TIMP1 and LRG1, or their protein products, are measured. In a further embodiment, the expression levels of the RNA transcripts of TIMP1 and/or LRG1, and G-CSF, or their protein products are measured. In a particular embodiment, the expression levels of the RNA transcripts of TIMP1, LRG1, and G-CSF, or their protein products, are measured. In a further embodiment, when the method includes measuring the expression level of any one of the genes selected from the group TIMP1, LRG1, CXCL1, CXCL5, CXCL10, IL8, YKL40, and G-CSF, its protein product is measured. When the method includes measuring the expression level of NFκBIZ, its RNA transcript is measured.

In one embodiment, the expression level of one or more of the genes selected from the group TIMP1, LRG1, CXCL1, CXCL5, CXCL10, IL8, NFκBIZ, YKL40, and G-CSF may be measured from the CSF obtained from an MS patient. In a particular embodiment, when the method includes measuring the expression level of one or more genes selected from CXCL1, CXCL5, and CXCL10, its RNA transcript or protein product may be measured from blood plasma obtained from an MS patient. In another embodiment, when the method includes measuring the expression level of G-CSF, its RNA transcript or protein product may be measured from the blood serum obtained from an MS patient. In a particular embodiment, the expression level of the protein product of G-CSF is measured from the blood serum.

In any of the methods and embodiments described above, MS may be RRMS.

The effects of administration of the IL-17 antagonist on multiple sclerosis can be measured by a variety of assays or tests known in the art. A number of measures, including clinical measures, those based on MRI scans, and those based on quality of life, can be used to assess a product's efficacy in treating MS. The Expanded Disability Status Scale (EDSS) is an extensively used tool for tracking the course of disability in MS. It classifies the most common MS-associated neurological impairments into disability levels ranging from 0 to 10, with each successive step describing a worsening of disease. In the lower range of the EDSS scale, disease progression is primarily defined by increasing levels of disability in specific functional systems measured during neurological examination. Scores of 1.0 through 3.5 describe mild to moderate disability in the functional systems. Higher scores, in the range of 4.0 and above indicate increasingly severe disability that affects ambulation, including the need for assistive devices such as a cane (an EDSS of 6.0), a walker (an EDSS of 6.5), or a wheelchair (an EDSS of 7.0). Scores higher than 7.0 classify patients confined to bed.

The MS Functional Composite (MSFC) (Whitaker et al., Multiple Sclerosis 1:37-47 (1995)) is also used to assess efficacy. Unlike traditional MS clinical outcome measures that are derived from the standard neurological examination, the MSFC is based on quantitative tests of leg function/ ambulation (the Timed 25-Foot Walk), arm function (the Nine-Hole Peg Test), and cognitive function (the Paced Auditory Serial Addition Test (PASAT 3)) which expand upon the measurements of the EDSS and assess effects in clinical dimensions not well captured by this scale.

MRI is another tool for assessing efficacy in treating MS and can be used alone or to support clinical data to assess therapeutic effects on relapse and disability endpoints. MRI is a sensitive tool for monitoring disease activity, detecting approximately five to ten times more disease activity in both relapsing remitting MS and secondary progressive MS patients than is clinically apparent (Isaac et al., Neurology 38:1511-1515 (1988); Willoughby et al., Ann. Neurol. 25:43-44 (1989); Khoury et al., Neurology 44:2120-2124 (1994); Thompson et al., Ann. Neurol. 9:53-62 (1991); Thompson et al., Neurology 42:60-63 (1992)). T2-weighted sequences in MS patients detect new areas of acute demyelination, as well as more chronic areas of demyelination and gliosis. For this reason, T2-weighted MRI is a good technique for monitoring the accumulation of lesions over time, either as a count of active lesions or a change in the total volume of such lesions.

Infusion of gadolinium-diethylenetriamine pentaacetic acid (Gd-DPTA) during acquisition of T1-weighted sequences allows for visualization of blood-brain barrier breakdown secondary to the inflammation characteristic of acute MS lesions. The evidence to date suggests that gadolinium (Gd)-enhancement is a useful marker of disease activity that correlates with clinical relapse (Molyneux et al., Ann. Neurol. 43:332-339 (1998); Kappos et al., Lancet 353:964-969 (1999); McFarland et al., Multiple Sclerosis 8:40-51 (2002)).

New hypointense lesions on T1-weighted sequences in MS patients correspond either with inflammatory Gd-enhancing lesions (comprising edema, demyelination, axonal loss, or combinations of these pathologies) (Bruck et al., Ann. Neurol. 42:783-793 (1997)) or as chronic lesions with considerable axonal loss. Approximately half of the acute T1 hypointensities on MRI will evolve into chronic "T1 black holes," which correlate with disability progression (Simon et al., Neurology 55:185-192 (2000)).

IL-17 Antagonists

An IL-17 antagonist includes any molecule that inhibits, reduces or interferes with the function or binding of IL-17, such as IL-17AA, IL-17FF, and/or IL-17A/F to the receptor, blocks, and/or neutralizes a relevant activity of IL-17. The IL-17 antagonist may prevent the interaction between IL-17 (including IL-17AA, IL-17FF, and/or IL-17A/F) and one or more of its receptors. Such antagonists accomplish this effect by, for example, binding to IL-17, or a receptor of IL-17, with sufficient affinity and specificity to interfere with IL-17 activity. The term "IL-17 antagonist" is used to refer to any and all of antagonists of IL-17AA, IL-17FF, IL-17A/F, IL-17RA, and IL-17RC. In certain embodiments, the inhibition, reduction, interference, blocking or neutralization can be partial or full inhibition, reduction, interference, blocking or neutralization of an activity of IL-17AA, IL-17FF and/or IL-17AF. In certain other embodiments, the inhibition, reduction, interference, blocking or neutralization can be 10%, 20%, 30%, 40%, 50%, 60%, 70%, 80%, 90% or 100% inhibition, reduction, interference, blocking or neutralization of an activity of IL-17AA, IL-17FF and/or IL-17AF.

Included within this group of antagonists are, for example, antibodies directed against IL-17 or portions thereof, reactive with IL-17, or an IL-17 receptor or portions thereof, including antibodies that bind IL-17AA, IL-17FF, IL-17A/F, IL-17RA, and/or IL-17RC, and soluble molecules of the IL-17 receptor, such as soluble IL-17RA and soluble IL-17RC. The term antagonist also includes any agent that will interfere in the production of IL-17AA, IL-17FF, and/or IL-17A/F or antagonize an IL-17 receptor, such as IL-17RA and/or IL-17RC. Such antagonists may be in the form of chimeric hybrids, useful for combining the function of the agent with a carrier protein to increase the serum half-life of the therapeutic agent or to confer cross-species tolerance. Hence, examples of such antagonists include bioorganic molecules (e.g., peptidomimetics), antibodies, proteins, peptides, glycoproteins, glycopeptides, glycolipids, polysaccharides, oligosaccharides, nucleic acids, pharmacological agents and their metabolites, transcriptional and translation control sequences, and the like. In an embodiment, the antagonist is an IL-17 antibody capable of binding to IL-17AA, IL-17FF, and/or IL-17A/F, or an IL-17 receptor antibody capable of binding to IL-17RA and/or IL-17RC.

Exemplary IL-17 antibodies include secukinumab (e.g., U.S. Pat. No. 7,807,155), ixekizumab (e.g., U.S. Pat. No. 7,838,638), bimekizumab (e.g., U.S. Pat. No. 8,580,265), ALX-0761 (e.g., U.S. Pub. No. 20140314743), CNTO 6785 (e.g., U.S. Pat. No. 8,519,107) and afasevikumab (the anti-IL17 CDR sequences as shown in U.S. Pat. No. 8,715,669). An exemplary IL-17 receptor antibody includes brodalumab (e.g., U.S. Pat. No. 7,833,527).

Production of Antibodies

Exemplary techniques for the production antibodies used in accordance with the present invention are provided below. The antigen to be used for production of antibodies may be full length, or a portion thereof, containing the desired epitope. Alternatively, cells expressing the desired antigen or epitope at their cell surface may be used to generate antibodies. Other forms of antigens useful for generating antibodies will be apparent to those skilled in the art.

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Various methods for making monoclonal antibodies herein are available in the art. For example, the monoclonal antibodies may be made using the hybridoma method first described by Kohler et al., Nature, 256:495 (1975), by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807. Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Antigen-Binding Fragments

Various techniques have been developed for the production of antibody fragments comprising one or more antigen binding regions. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. For example, the antigen-binding fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a linear antibody, e.g., as described in U.S. Pat. No. 5,641,870. Such linear antibody fragments may be monospecific or bispecific.

Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991). According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in WO96/27011, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373). Heteroconjugate antibodies may be made using any convenient cross-linking methods. Suitable cross-linking agents are well known in the art, and are disclosed in U.S. Pat. No. 4,676,980, along with a number of cross-linking techniques. In certain embodiments, the IL-17 antibody is a bispecific or multispecific antibody that binds to IL-17AA, IL-17FF and/or IL-17AF. In certain other embodiments, the IL-17 antibody is a bispecific or multispecific antibody in which one antigen biding site binds to IL-17AA and IL-17AF and the other antigen binding site binds to IL-17FF; while in yet other embodiments, one antigen binding site binds to IL-17AA and the other antigen binding site binds to IL-17FF and IL-17AF. In certain other embodiments, one binding site binds to IL-17AF and IL-17FF and the other antigen binding site binds to IL-17AA, IL-17FF and IL-17AF. In certain other embodiments, one antigen binding site of the bispecific or multispecific antibody binds to IL-17AA, IL-17AF, and/or IL-17FF and the other antigen binding site binds to a second antigen. In some embodiments, the second antigen is an inflammatory mediator. In some embodiments, the second antigen is TNFα or IL-1, Techniques for generating bispecific antibodies from antibody fragments have also been described in the literature. For example, bispecific antibodies can be prepared using chemical linkage. Brennan et al., Science 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments can also be directly recovered from *E. coli*, and can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Nat. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al, J. Immunol, 152:5368 (1994).

Antibodies with more than two valencies are contemplated. For example, trispecific antibodies can be prepared. Tuft et al. J. Immunol. 147: 60 (1991).

Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in the following table, or as further described below in reference to amino acid classes, may be introduced and the products screened.

TABLE 2

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

non-polar: Ala (A), Val (V), Leu (L), Ile (I), Pro (P), Phe (F), Trp (W), Met (M)
uncharged polar: Gly (G), Ser (S), Thr (T), Cys (C), Tyr (Y), Asn (N), Gln (Q)
acidic: Asp (D), Glu (E)
basic: Lys (K), Arg (R), His (H)

Alternatively, naturally occurring residues may be divided into groups based on common side-chain properties:
hydrophobic: Norleucine, Met, Ala, Val, Leu, Ile;
neutral hydrophilic: Cys, Ser, Thr, Asn, Gln;
acidic: Asp, Glu;
basic: His, Lys, Arg;
residues that influence chain orientation: Gly, Pro;
aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fructose attached to an Fc region of the antibody are described in US Pat. Appl. No. US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues).

Engineered antibodies with three or more (preferably four) functional antigen binding sites are also contemplated (US Appln. No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Administration and Formulations

The IL-17 antagonist may be administered by any suitable route, including a parenteral route of administration such as, but not limited to, intravenous (IV), intramuscular (IM), subcutaneous (SC), and intraperitoneal (IP), as well as transdermal, buccal, sublingual, intrarectal, intranasal, and inhalant routes. IV, IM, SC, and IP administration may be by bolus or infusion, and in the case of SC, may also be by slow-release implantable device, including, but not limited to pumps, slow-release formulations, and mechanical devices. In an embodiment of the invention, administration is systemic.

In a particular embodiment, the method for administration of IL-17 antagonist is by subcutaneous infusion, particularly using a metered infusion device, such as a pump. Such pump can be reusable or disposable, and implantable or externally mountable. Medication infusion pumps that are usefully employed for this purpose include, for example, the pumps disclosed in U.S. Pat. Nos. 5,637,095; 5,569,186; and 5,527,307. The compositions can be administered continually from such devices, or intermittently.

Therapeutic formulations of IL-17 antagonists suitable for storage include mixtures of the antagonist having the desired degree of purity with pharmaceutically acceptable carriers, excipients, or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Examples of lyophilized anti-IL-17 antibody formulations are described in WO 97/04801. These compositions comprise antagonist to IL-17 containing from about 0.1 to 90% by weight of the active antagonist, preferably in a soluble form, and more generally from about 10 to 30%.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

The IL-17 antagonists, such as anti-IL-17 antibodies disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide interchange reaction.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

Any of the specific antagonists can be joined to a carrier protein to increase the serum half-life of the therapeutic antagonist. For example, a soluble immunoglobulin chimera, such as described herein, can be obtained for each specific IL-17 antagonist or antagonistic portion thereof, as described in U.S. Pat. No. 5,116,964. The immunoglobulin chimera are easily purified through IgG-binding protein A-Sepharose chromatography. The chimera have the ability to form an immunoglobulin-like dimer with the concomitant higher avidity and serum half-life.

The formulations to be used for in vivo administration must be sterile. This is readily accomplished by filtration through sterile filtration membranes.

The formulation herein may also contain more than one active compound as necessary for the particular indication being treated, preferably those with complementary activities that do not adversely affect each other. Also, such active compound can be administered separately to the mammal being treated.

For example, it may be desirable to further provide a multiple sclerosis-treating agent that is not an IL-17 antagonist. Multiple sclerosis (MS)-treating agents include, without limitation, dimethyl fumarate (TECFIDERA®), FTY-720 (fingolimod, GILENYA®), nataluzimab (TYSABRI®), corticosteroids, β-interferons, glatiramer acetate (COPAXONE®), teriflunomide (AUBAGIO®), mitoxantrone, and anti-CD20 antibody, such as ocrelizumab, rituximab, and ofatumumab. In a particular embodiment, the MS-treating agent is dimethyl fumarate. In another embodiment, the MS-treating agent is FTY-720.

The multiple sclerosis-treating agent may be administered together or separately from the IL-17 antagonist. Such multiple sclerosis-treating agents are suitably present or administered in combination in amounts that are effective for the purpose intended, typically less than what is used if they are administered alone without the IL-17 antagonist. If they are formulated together, they may be formulated in the amounts determined according to, for example, the type of indication, the subject, the age and body weight of the subject, current clinical status, administration time, dosage form, administration method, etc. For instance, a concomitant drug is used preferably in a proportion of about 0.0001 to 10,000 weight parts relative to one weight part of the IL-17 antagonist.

The dosages of antagonist administered to a subject with multiple sclerosis will be determined by the physician in light of the relevant circumstances, including the condition of the subject, the type of antagonist, the type of indication, and the chosen route of administration. The dosage ranges presented herein are not intended to limit the scope of the invention in any way. An "effective amount" for purposes herein for multiple sclerosis is determined by the above factors, but is generally about 0.01 to 100 mg/kg body weight/day. In an embodiment, the dose is about 0.1-50 mg/kg/day, more particularly about 0.1 to 25 mg/kg/day. Further, when the IL-17 antagonist is administered daily, the intravenous or intramuscular dose for a human may be about 0.3 to 10 mg/kg of body weight per day, more particularly, about 0.5 to 5 mg/kg. For subcutaneous administration, the dose may be greater than the therapeutically-equivalent dose given intravenously or intramuscularly. In an embodiment, the daily subcutaneous dose for a human is about 0.3 to 20 mg/kg, more particularly about 0.5 to 5 mg/kg.

The present invention contemplates a variety of dosing schedules. The invention encompasses continuous dosing schedules, in which the IL-17 antagonist is administered on a regular (daily, weekly, or monthly, depending on the dose and dosage form) basis without substantial breaks. In an embodiment, continuous dosing schedules include daily continuous infusion, where the IL-17 antagonist is infused each day, and continuous bolus administration schedules, where the IL-17 antagonist is administered at least once per day by bolus injection or inhalant or intranasal routes. The invention also encompasses discontinuous dosing schedules. The exact parameters of discontinuous administration schedules will vary according to the formulation, method of delivery, and clinical needs of the subject being treated. For example, if the IL-17 antagonist is administered by infusion, administration schedules may comprise a first period of administration followed by a second period in which IL-17 antagonist is not administered that is greater than, equal to, or less than the first period.

Where the administration is by bolus injection, especially bolus injection of a slow-release formulation, dosing schedules may also be continuous in that the IL-17 antagonist is administered each day, or may be discontinuous, with first and second periods as described above.

Continuous and discontinuous administration schedules by any method also include dosing schedules in which the dose is modulated throughout the first period, such that, for example, at the beginning of the first period, the dose is low and increased until the end of the first period, the dose is initially high and decreased during the first period, the dose is initially low, increased to a peak level, then reduced towards the end of the first period, and any combination thereof.

Kits

The materials for use in the methods of the present invention are suited for preparation of kits. The kits of the invention may include one or more gene-specific or gene-selective probes and/or primers for quantifying the expression level of the RNA transcripts of the genes disclosed herein. Such kits may optionally contain one or more reagents for the extraction of RNA from biological samples. The kits may comprise one or more containers, each with one or more of the various materials or reagents utilized in the methods, including, for example, chromatographic columns, pre-fabricated microarrays, buffers, the appropriate nucleotide triphospages, reverse transcriptase, DNA polymerase, RNA polymerase, and one or more probes and primers for quantifying the expression level of the RNA transcripts disclosed herein.

Alternatively, or additionally, the kits of the invention may include one or more reagents for quantifying the expression level of the protein products of the genes disclosed herein. Such reagents include antibodies specific for the protein products and may optionally be labeled.

The kits of the invention may additionally or separately comprise one or more containers comprising one or more IL-17 antagonists, such as IL-17 antibodies. The kits may further comprise a set of instructions, generally written instructions, relating to the use and dosage of the IL-17 antagonist(s) for the treatment of multiple sclerosis. The instructions included with the kit generally include information as to dosage, dosing schedule, and route of administration for the treatment of multiple sclerosis. The IL-17 antagonist(s) may be provided in unit doses, bulk packages (e.g., multi-dose packages), or sub-unit doses.

Further details of the invention will be described in the following non-limiting Examples.

Example 1

CSF IL17 Levels and Other Inflammatory Mediators are Elevated in RRMS Patients

IL-17AA, IL-17FF and various other proteins were measured in cerebrospinal fluid (CSF) and serum from 50 RRMS patients receiving standard-of-care therapies and 20 healthy donors (HD) using an immunoassay based on the Erenna® Immunoassay platform (Singulex, Inc.) in the case of IL-17A and IL-17F, or standard sandwich immunoassays. The IL-17A immunoassay specifically measured IL-17AA homodimer cytokine with approximately 30% cross reactivity with the IL-17AF heterodimer, while the IL-17F assay measured only IL-17FF homodimer with no detectable cross reactivity with IL-17AF or AA. All immunoassays employed monoclonal capture and detection antibodies.

Figure 6:
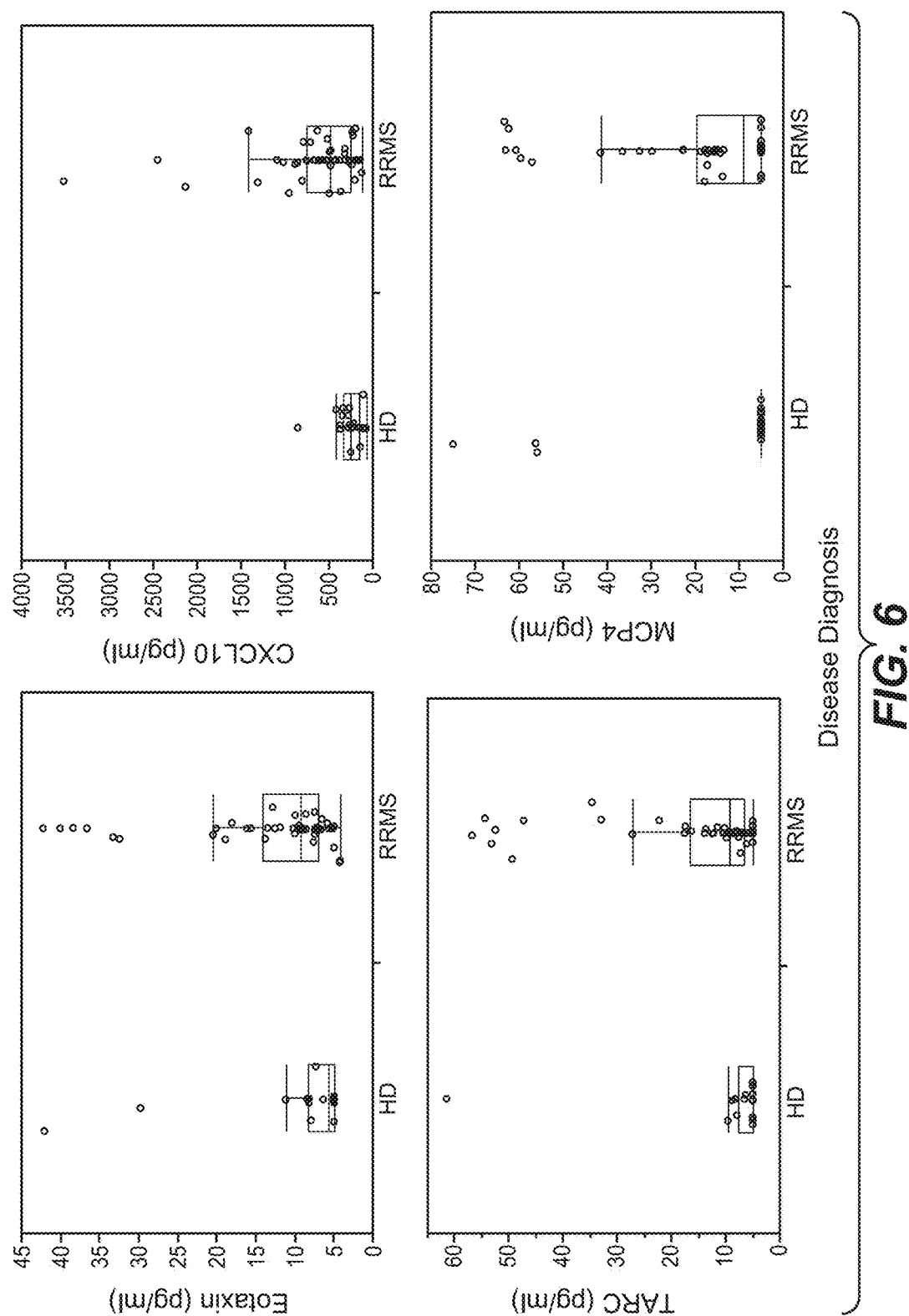
FIG. 6 shows multiple inflammatory mediators, eotaxin, CXCL10, TARC, and MCP4, elevated in RRMS CSF samples ($p<0.03$ vs. healthy donors (HD) for all analytes) as described in Example 1 below.

As shown in FIG. 6, multiple inflammatory mediators were elevated in some RRMS CSF samples, including eotaxin, CXCL10, TARC, and MCP4 ($p<0.03$ vs. healthy donor for all analytes).

Figure 7A:
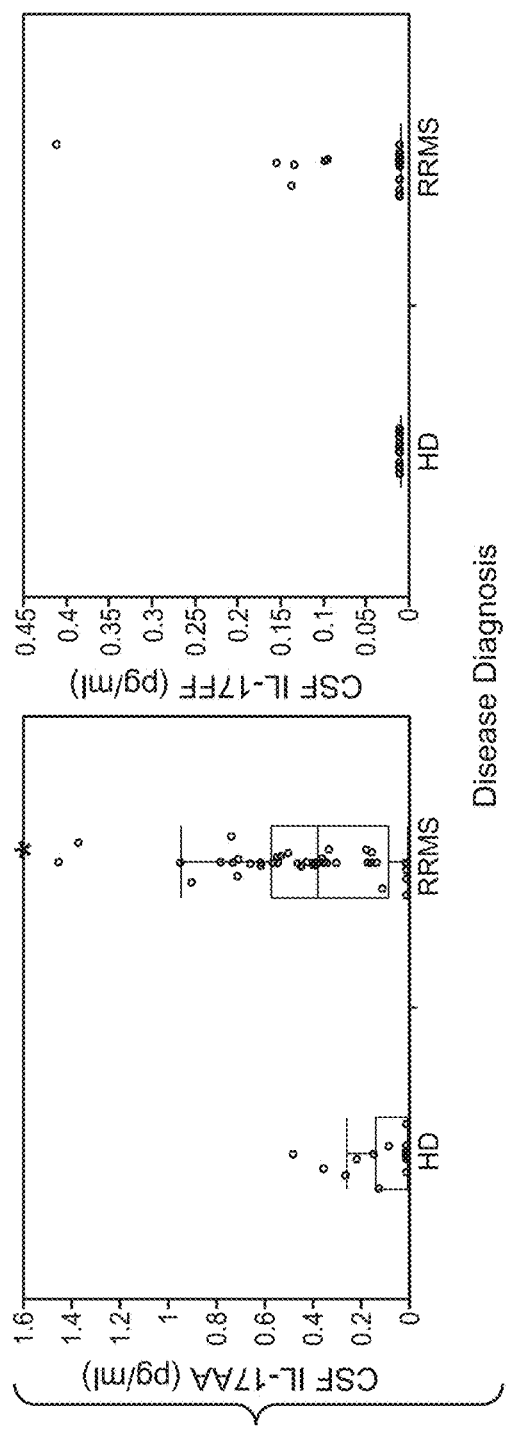
FIG. 7A-7B show (A) CSF IL-17AA and IL-17FF were elevated in RRMS patients vs healthy donors (HD) ($p<0.0001$, Wilcoxon test) and (B) no elevation of serum IL-17AA or IL-17FF in RRMS patients vs. HD, as described in Example 1 below.
Figure 7B:
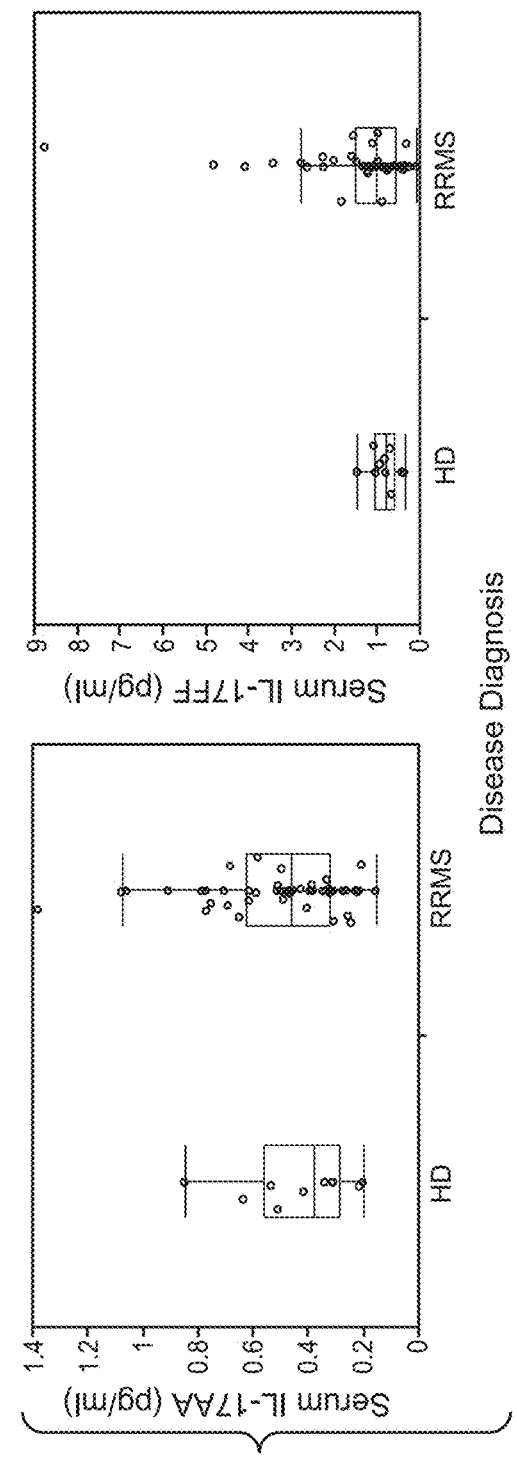

IL-17AA and IL-17FF levels were also analyzed in the CSF samples of RRMS patients. The results in FIG. 7 show that IL-17AA levels were higher in the CSF of RRMS patients than in the control subjects. Specifically, IL-17AA was detectable in 76% of RRMS patients versus 50% of control subjects, with a median CSF IL-17AA level of 0.4 pg/mL in RRMS patients versus 0.07 pg/mL in control subjects (with a dynamic range of about 10 fold). See FIG. 7A, left panel (*$p<0.0001$, Wilcoxon test). IL-17FF levels were detectable in the CSF of 12% of RRMS patients versus 0% in control patients. See FIG. 7A, right panel. In contrast, elevation of the levels of serum IL-17AA and IL-17FF in RRMS patients was not observed. See FIG. 7B.

However, the levels of IL-17AA and IL-17FF in CSF were still considered low to be useful biomarkers for in vitro diagnostics. Thus, surrogate biomarkers were sought for the subset of patients with RRMS who exhibit high IL-17AA levels.

Example 2

Upregulation of IL-17 Responsive Genes in Human Brain Endothelial Cells and Microglia In Vitro A hCMEC/D3 immortalized human brain endothelial cell line and SV40-transformed human microglia cell line were expanded using standard cell culture protocols, and then stimulated with TNFa, IL-6 plus sIL-6R, IL-17AA or combinations of these cytokines for 6 hours. RNA was then isolated from the cells and microarray analysis performed to compare gene expression induced by IL-17 with or without additional cytokines.

Figure 8A:
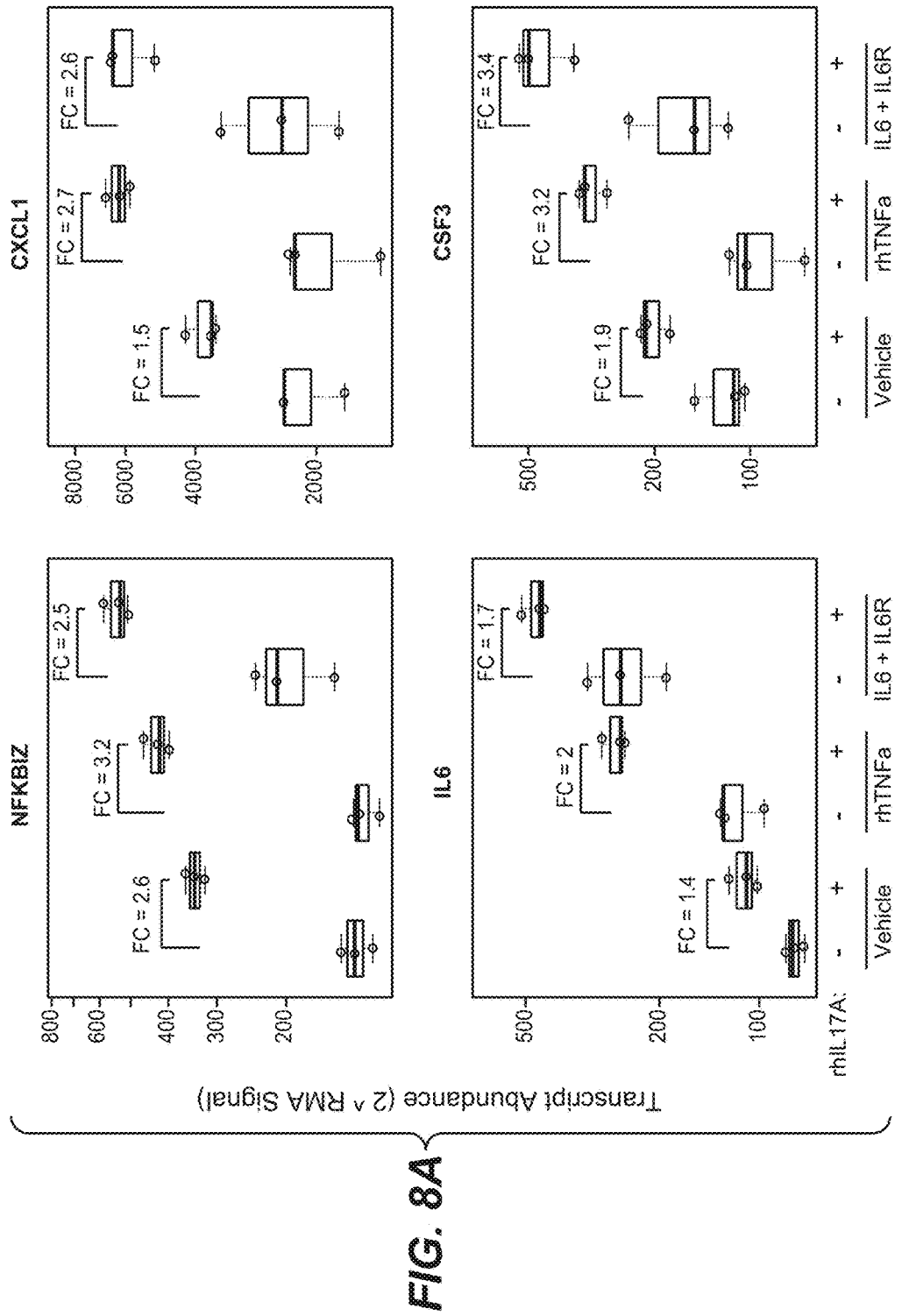
FIG. 8A-8B show upregulation of NFκBIZ, CXCL1, IL-6, and CSF3 in (A) human brain endothelial cells and (B) microglia upon stimulation with IL-17A, and further amplification in the presence of TNFa and IL-6+6R ($p<0.05$ (pairwise t-test) for all comparisons, except for those in brackets with "FC," which stands for "fold change"). See Example 2 below.
Figure 8B:
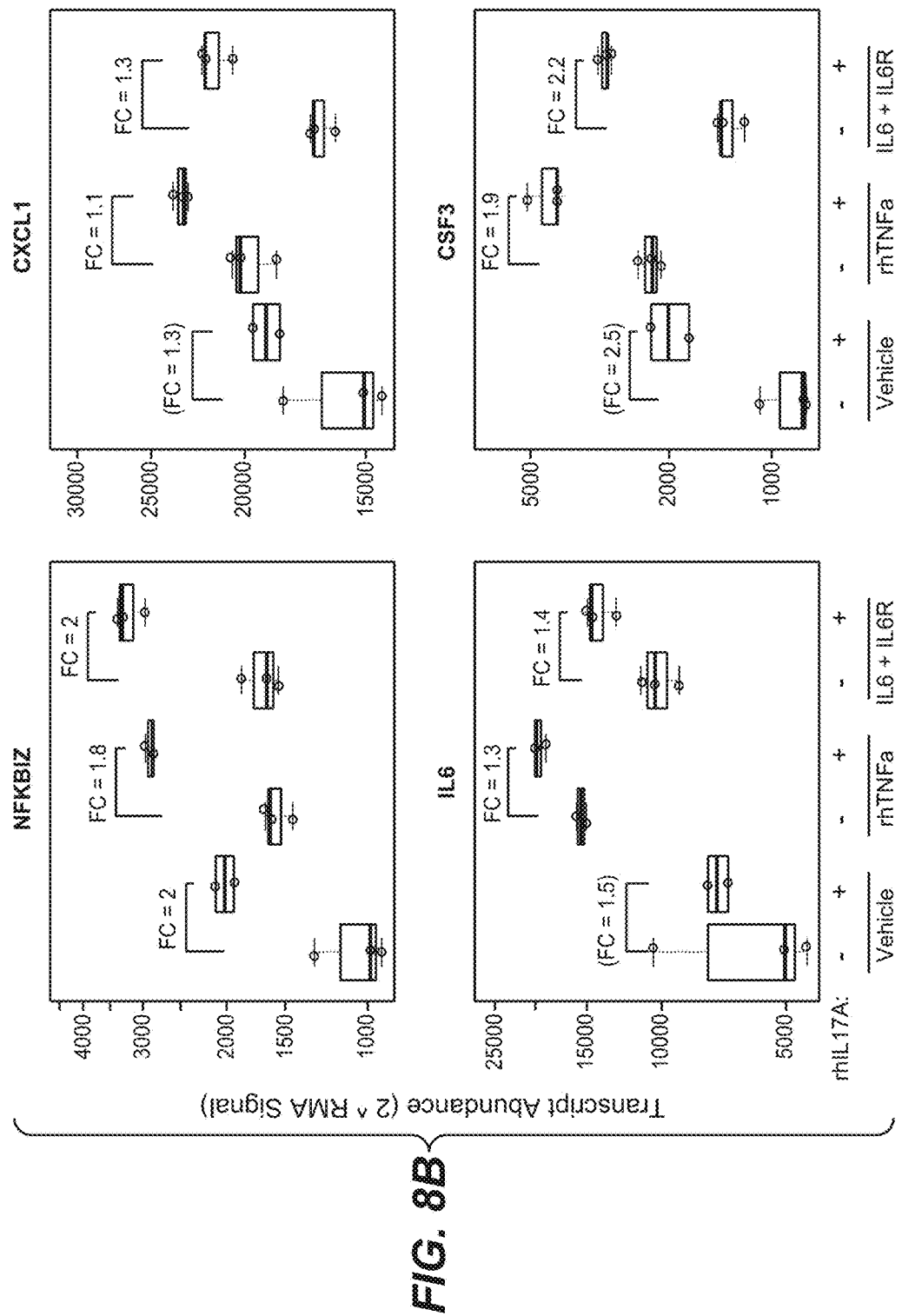

Human brain endothelial cells (see FIG. 8A) and microglia (see FIG. 8B) were stimulated with IL-17A in the presence or absence of TNFα and IL-6+6R. FIGS. 8A and 8B show that the amplification of gene expression related to STAT and NF-κB signaling, such as NFκBIZ, CXCL1, IL-6 and CSF3 (G-CSF), was elevated with IL-17A, but was further amplified in both cell types in the presence of TNFα or IL6+IL6R ($p<0.05$ (pairwise t-test) for all comparisons, except those in brackets with "FC," which stands for "fold change").

Example 3

Identification of RRMS Biomarkers in the EAE Model In Vivo

Experimental autoimmune encephalomyelitis (EAE) in mice is a $CD4^+$ T cell-mediated autoimmune disease characterized by perivascular $CD4^+$ T cell and mononuclear cell inflammation and subsequent primary demyelination of axonal tracks in the central nervous system (CNS), leading to progressive hind-limb paralysis. EAE provides a powerful model for the study of the pathogenesis and immune regulation of $CD4^+$ $T_H1/T_H17$-mediated tissue damage and is generally considered to be a relevant model for the human immune-mediated demyelinating disease multiple sclerosis. In the C57BL/6 mice, EAE can be induced by immunization with the peptide corresponding to the immunodominant epitope of MOG ($MOG_{35-55}$). The EAE model is useful for identifying biomarkers correlating with IL-17AA by determining the modulation of biomarkers by various IL-17 blocking antibodies.

Genome-wide expression analysis was performed on RNA isolated from spinal cord tissues from mice with active EAE after 48 hours of treatment with anti-IL-17 antibodies vs. controls. See FIG. 9. Specifically, C57BL/6 mice were immunized with 300 µg of $MOG_{35-55}$ in complete freunds adjuvant containing 800 µg of heat-inactivated *Mycobacterium tuberculosis* (Mtb) (day 0). In addition, 200 ng pertussis toxin (PTX) was administered on day 0 and day 2 post immunization. Mice (8 mice per group) were randomized at peak of disease (day 14) into the following treatment groups shown in Table 3:

TABLE 3

| Treatment | Dose |
| --- | --- |
| aIL-17AA (antibody specific to the IL-17AA homodimer) | 10 mg/kg 0.2 ml IP |
| aIL-17 FF (antibody specific to the IL-17FF homodimer) | 10 mg/kg 0.2 ml IP |
| aIL-17AA + FF (combination of aIL-17AA and aIL-17FF) | 10 mg/kg each 0.2 ml IP |
| aIL-17AA/AF (antibody specific for IL-17A and binds IL-17AA homodimer and the IL-17AF heterodimer) | 10 mg/kg 0.2 ml IP |
| aIL-17AA/AF + aIL-17FF (combination of aIL-17AA/AF and aIL-17FF) | 10 mg/kg each 0.2 ml IP |
| a-gp120 mIgG2a (control) | 10 mg/kg 0.2 ml IP |
| dimethyl fumarate (DMF) (TECFIDERA ®) | 30 mg/kg/day b.i.d. PO |
| vehicle | 5 ml/kg b.i.d. PO 5 ml/kg |
| FTY-720 (fingolimod, GILENYA ®) | 3 mg/kg IP QD (one a day) |
| peak of disease control | 0.2 ml |
| naïve control | |

The effects of the anti-IL-17 antibodies were compared to small molecule drugs approved for treatment of multiple sclerosis. Dimethyl fumarate (TECFIDERA®) is an oral therapy approved in the United States for the treatment of relapsing forms of multiple sclerosis, including RRMS. Dimethyl fumarate is not known to affect the IL-17 pathway. FTY-720 (fingolimod, GILENYA®) is a sphingosine 1-phosphate (S1P) modulator approved for the treatment of relapsing forms of MS, including RRMS.

Antibody-treatment groups (the anti-IL-17 antibodies and a control anti-gp120 antibody) were treated on day 14 according to the doses shown in Table 3 and taken down 48 hours later on day 16 (one dose overall). DMF and vehicle-treatment groups were dosed b.i.d. (twice a day) starting on day 14 through day 15 (pm dose; 4 doses total), and taken down on day 16. The FTY-120-treatment group was dosed QD (once a day) on day 14 through day 15 (2 doses total) and taken down on day 16.

Spinal cords and serum were harvested at takedown on day 16 and gene expression analysis was performed on spinal cord tissue RNA.

Figures 1, 10A:
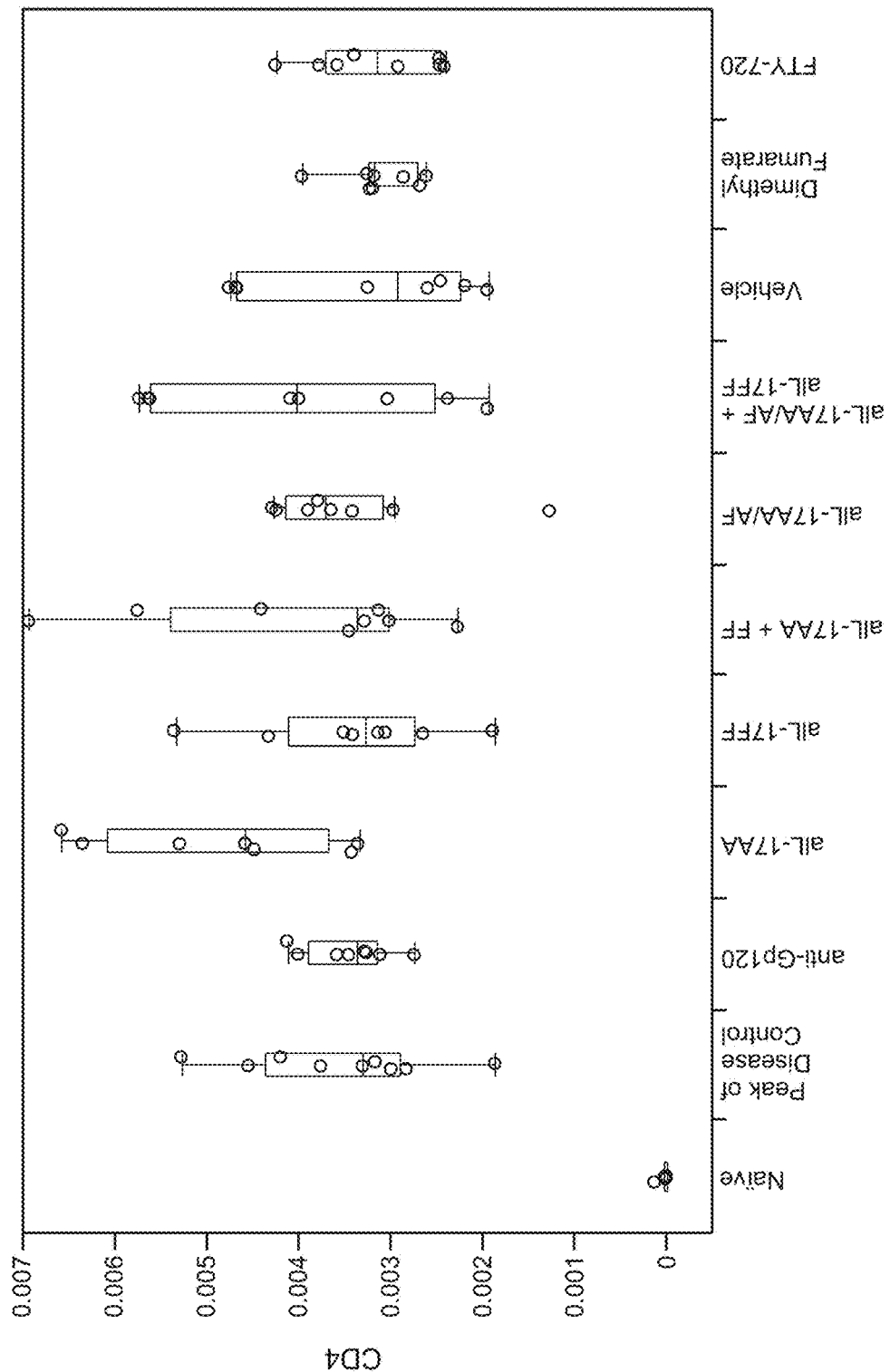
FIG. 10A-1 and FIG. 10A-2 shows increased lymphocyte (CD4 and CD45) and FIG. 10B-1 and FIG. 10B-2 show decreased myelin component (Mobp and Mog) gene expression at peak EAE disease as described in Example 3 below.
Figures 2, 10A:
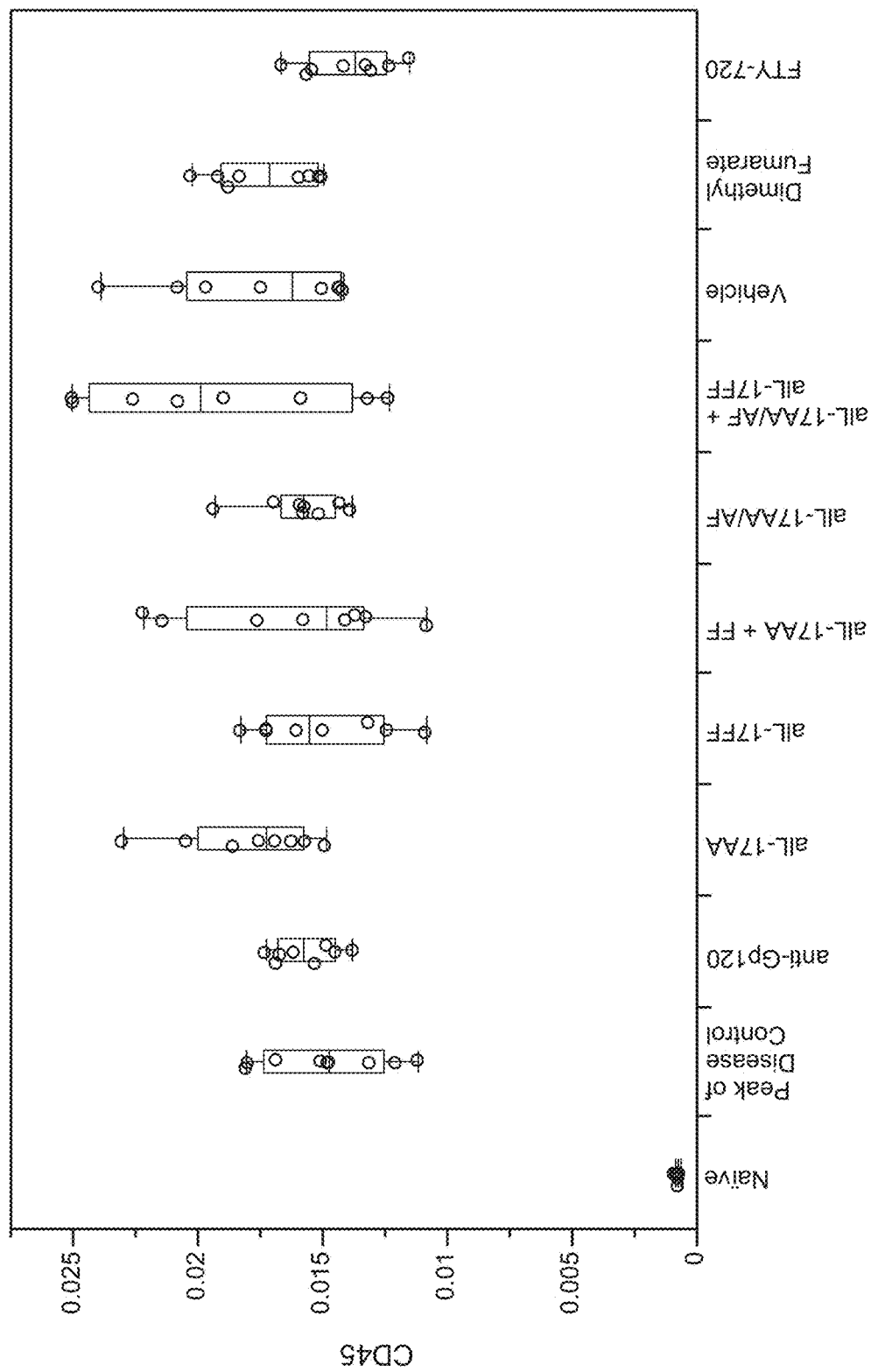
Figures 1, 10B:
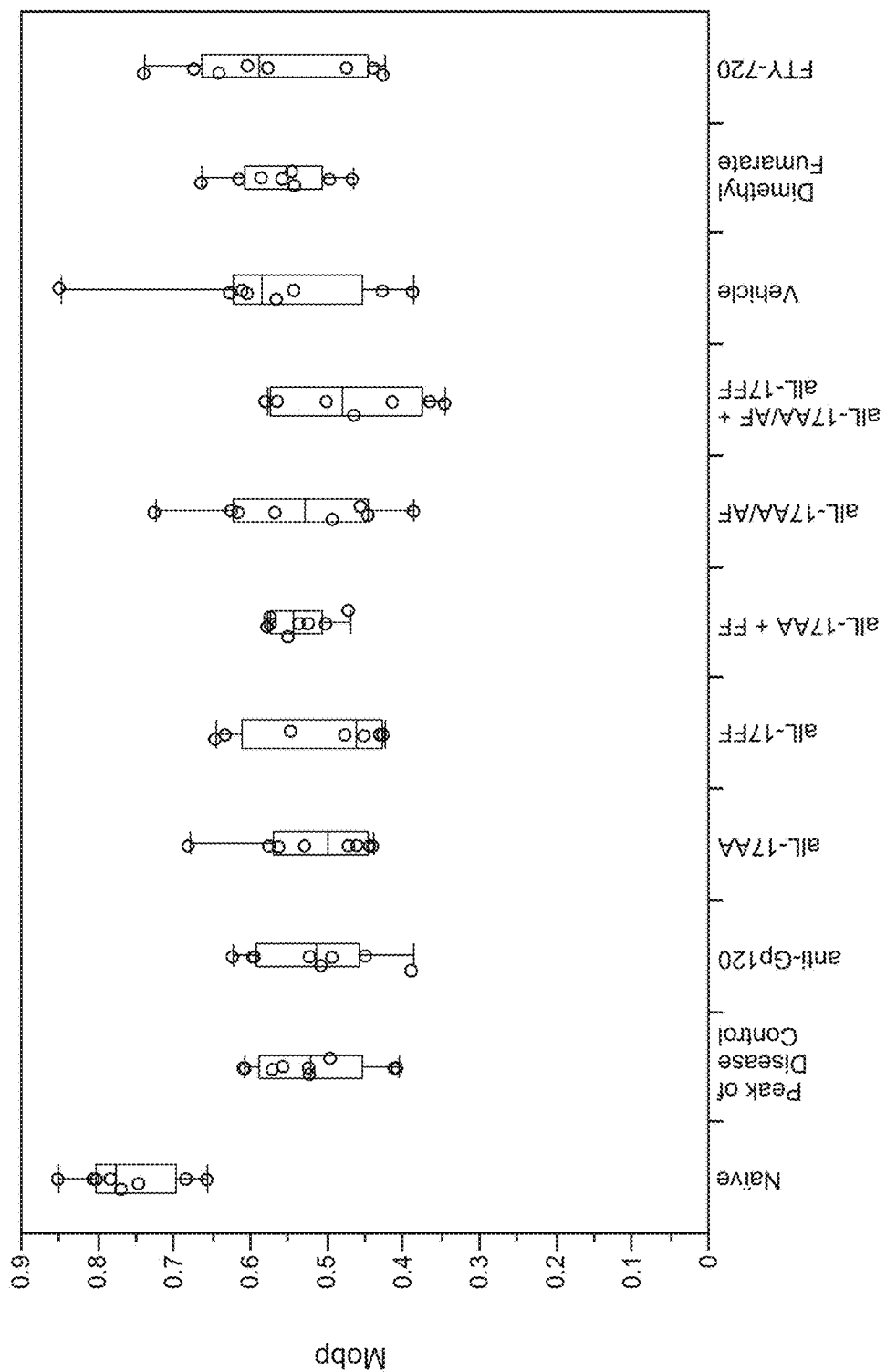
Figures 2, 10B:
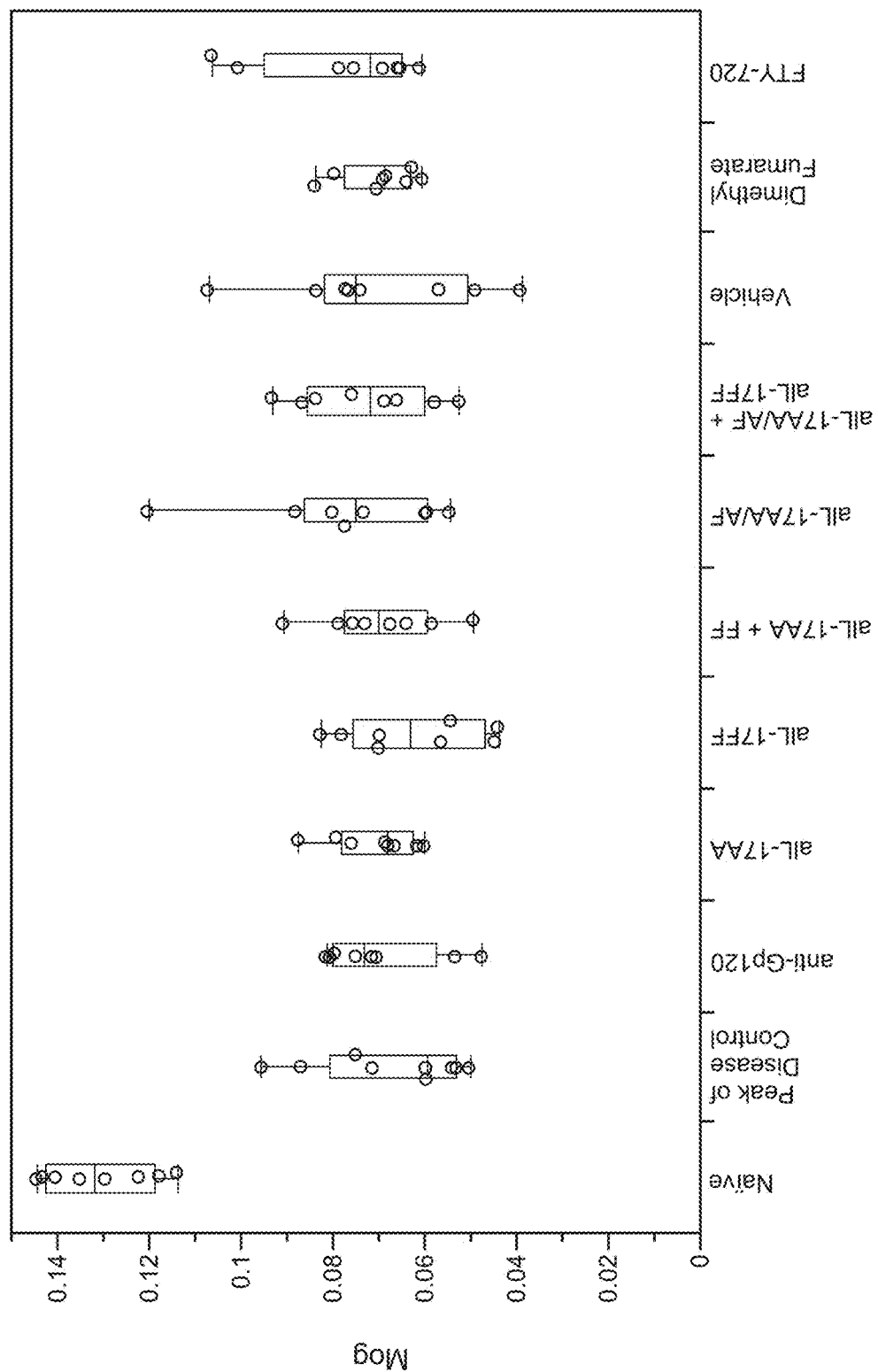

FIG. 10A shows that lymphocytes levels were increased as measured by markers such as CD4 and CD45 at peak EAE disease, while FIG. 10B shows that transcript abundance of myelin components such as those of the myelin-associated oligodendrocytic basic protein (Mobp) and myelin oligodendrocyte glycoprotein (Mog) were decreased at peak EAE disease, p<0.0007 vs. naïve controls for all genes (Wilcoxon test on each pair). The changes in the expression levels of inflammation- and myelination-related genes shown in FIG. 10 correlated with induction of the disease and thus confirmed the EAE animal model for MS; however, the changes in gene expression were not modulated by anti-IL17 treatments.

Figure 11:
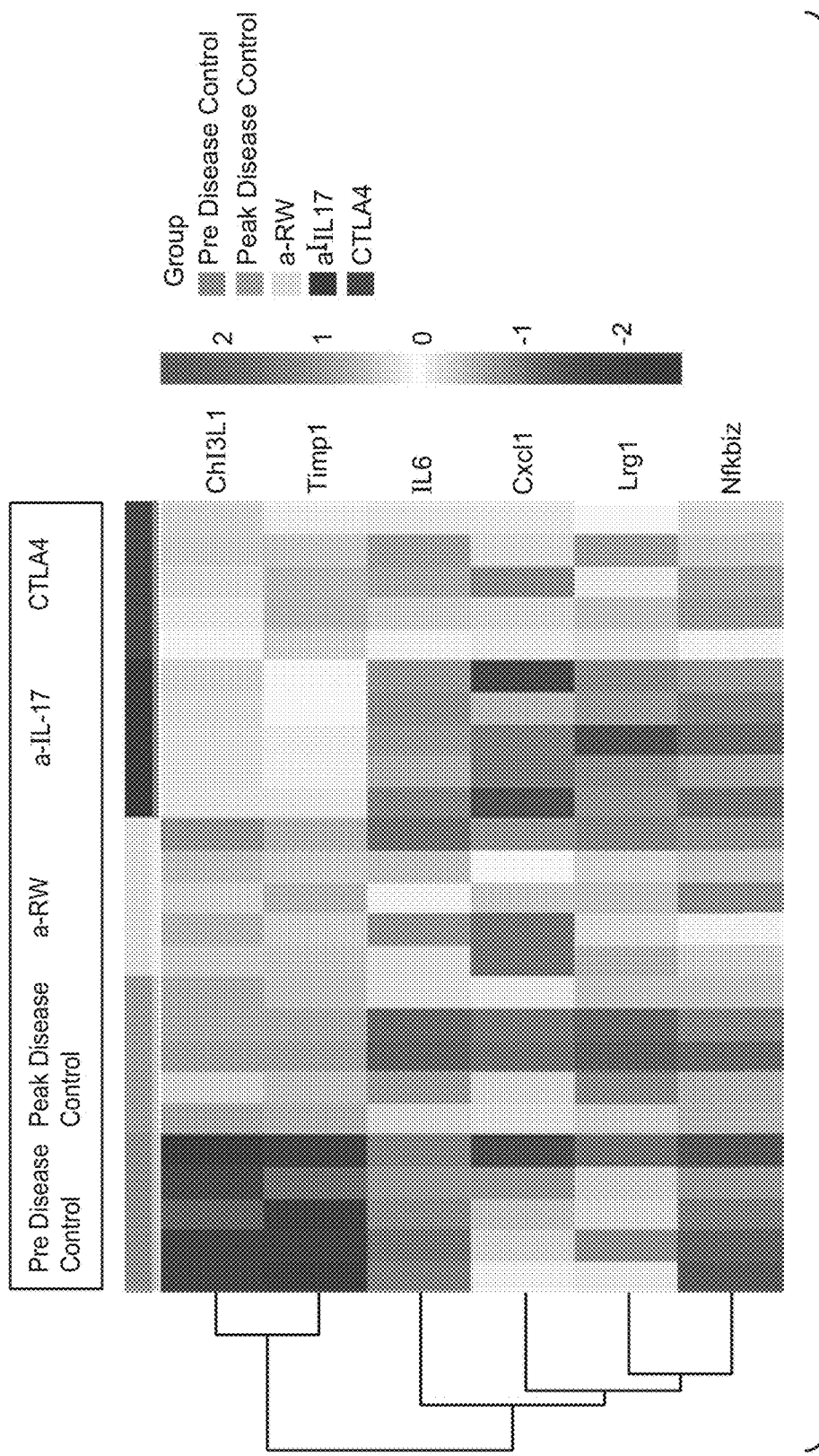
FIG. 11 shows upregulation of CHI3L1, TIMP1, IL-6, CXCL1, LRG1, and NFκB1 in EAE spinal cords at the peak of disease, and blockage of gene expression with anti-IL-17AA/AF+anti-IL-17 FF antibody as described in Example 3 below.
Figure 12A:
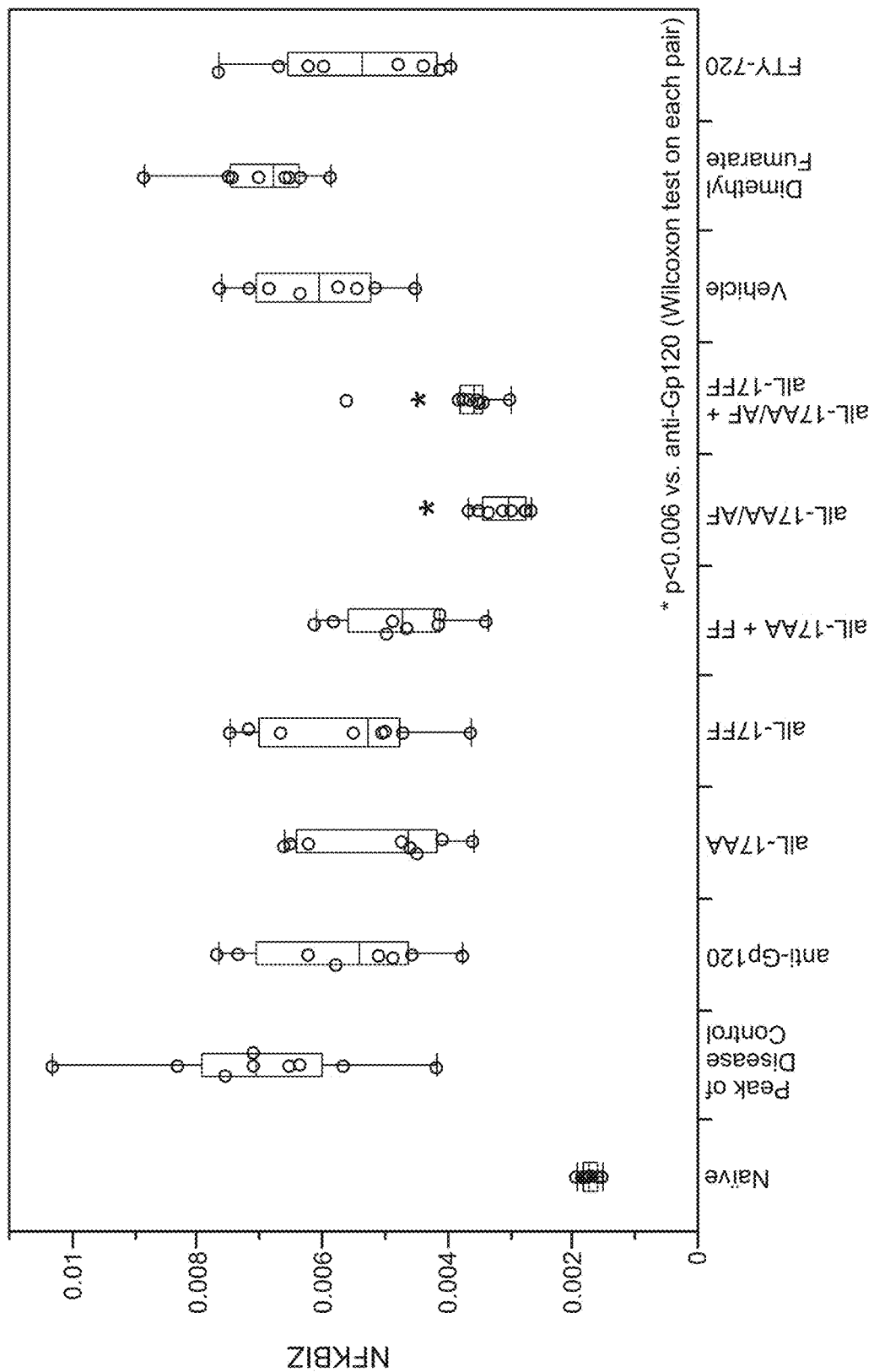
FIG. 12A-12F show transcript abundance plots of genes of (A) NFκBIZ, (B) CXCL1, (C) IL-6, (D) YKL40 (CHI3L1), (E) TIMP1, and (F) LRG1 in an EAE model with various treatments as described in Example 3 below.
Figure 12B:
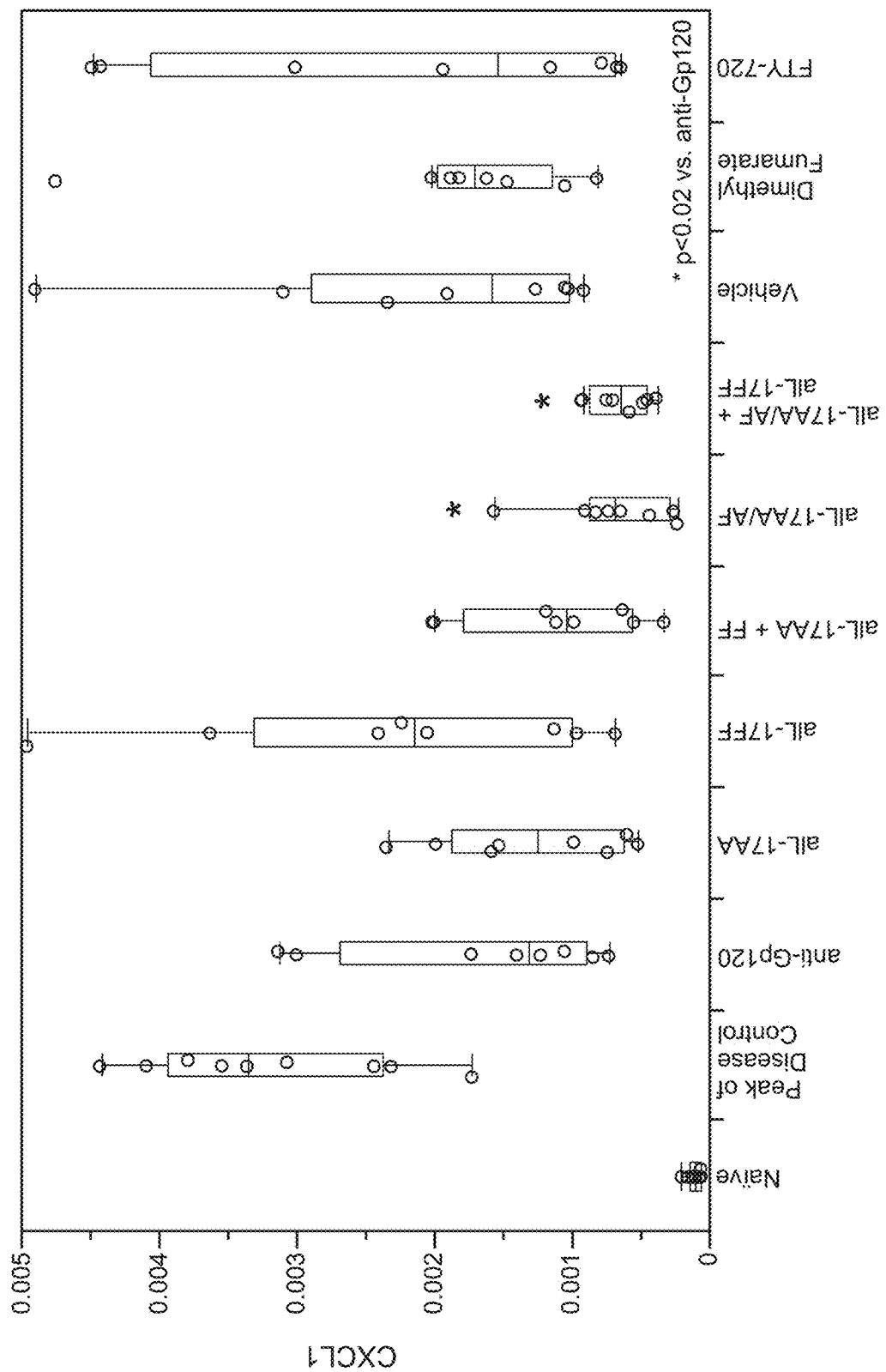
Figure 12C:
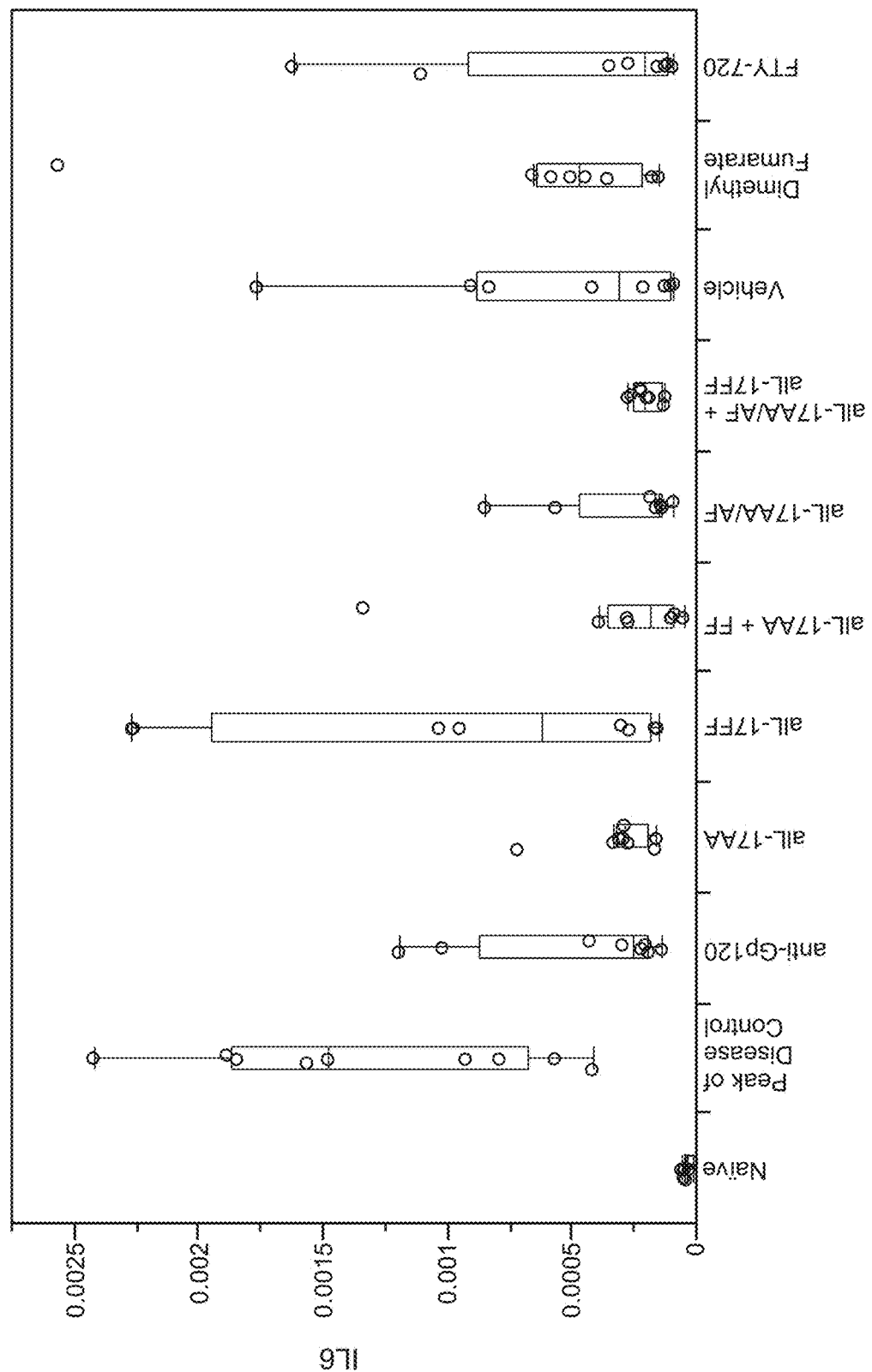
Figure 12D:
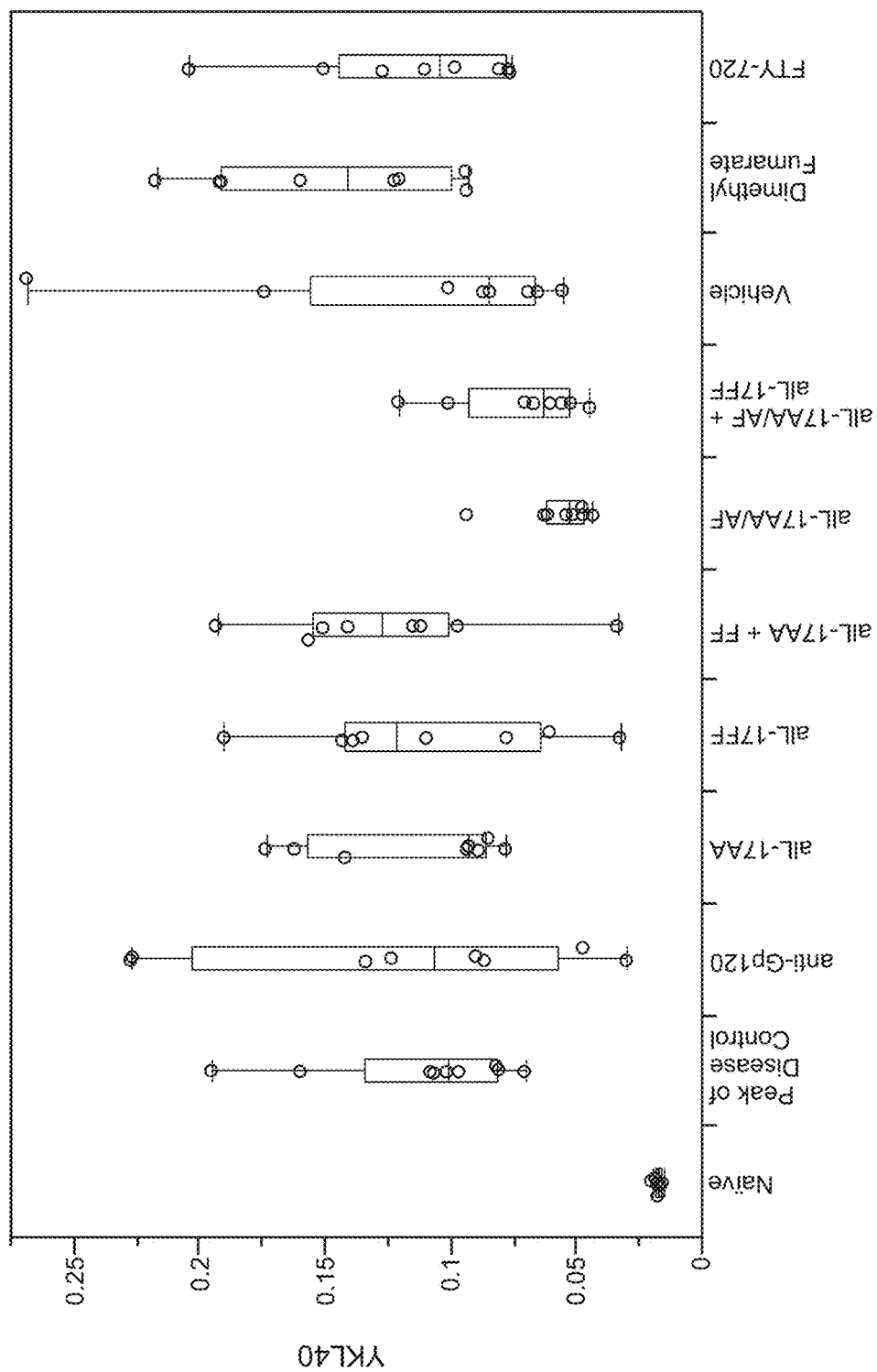
Figure 12E:
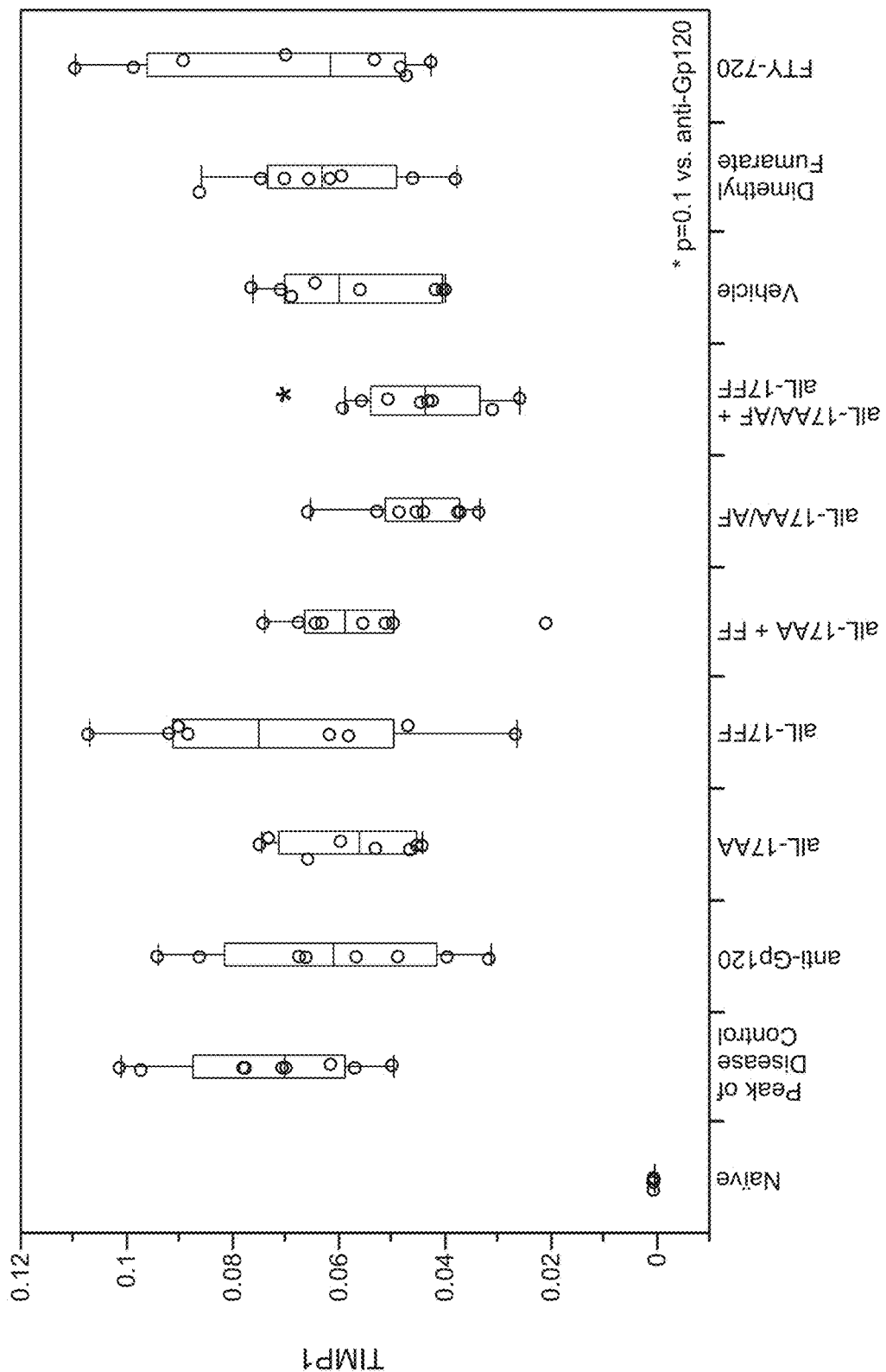
Figure 12F:
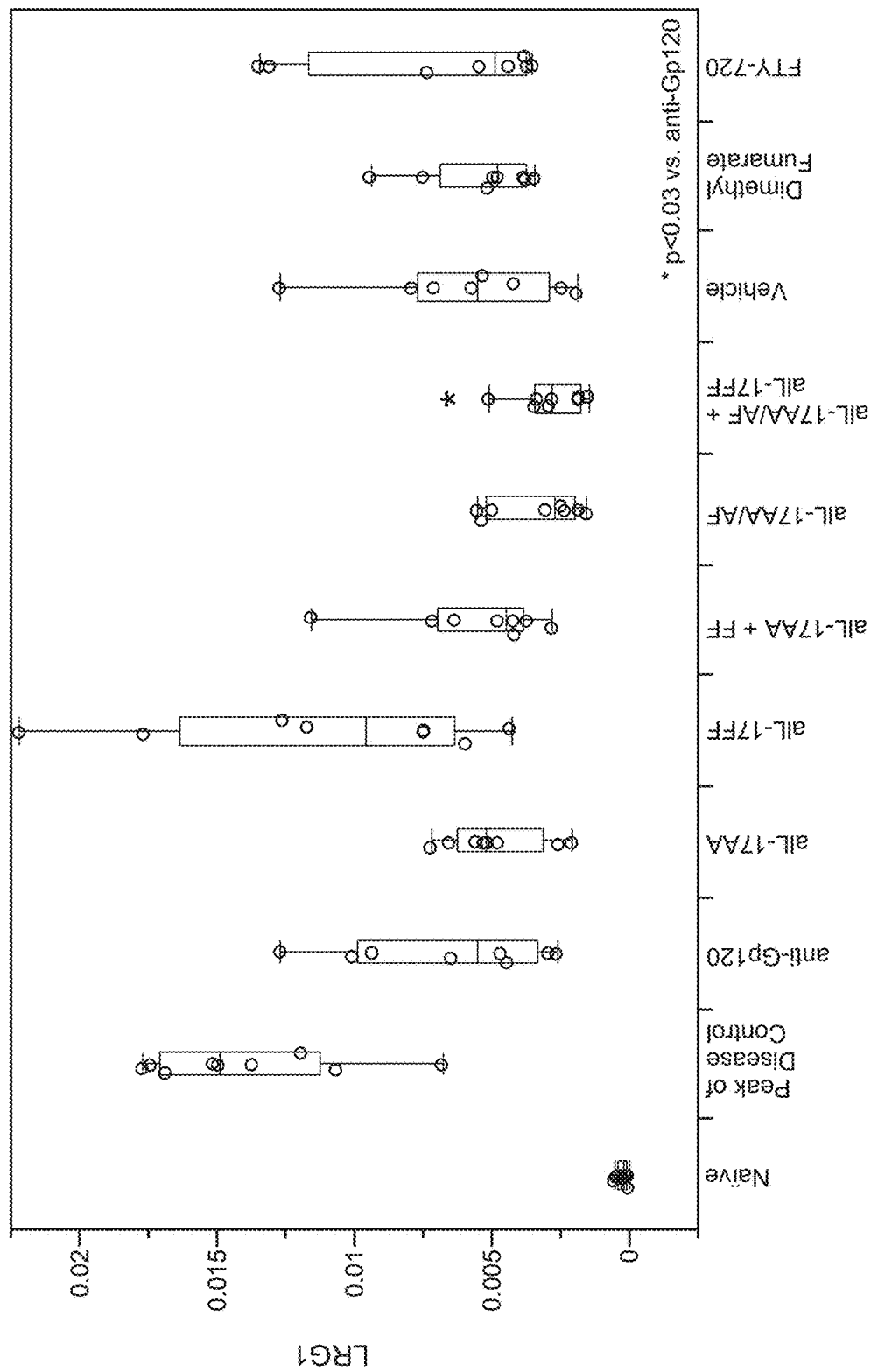
Figure 13:
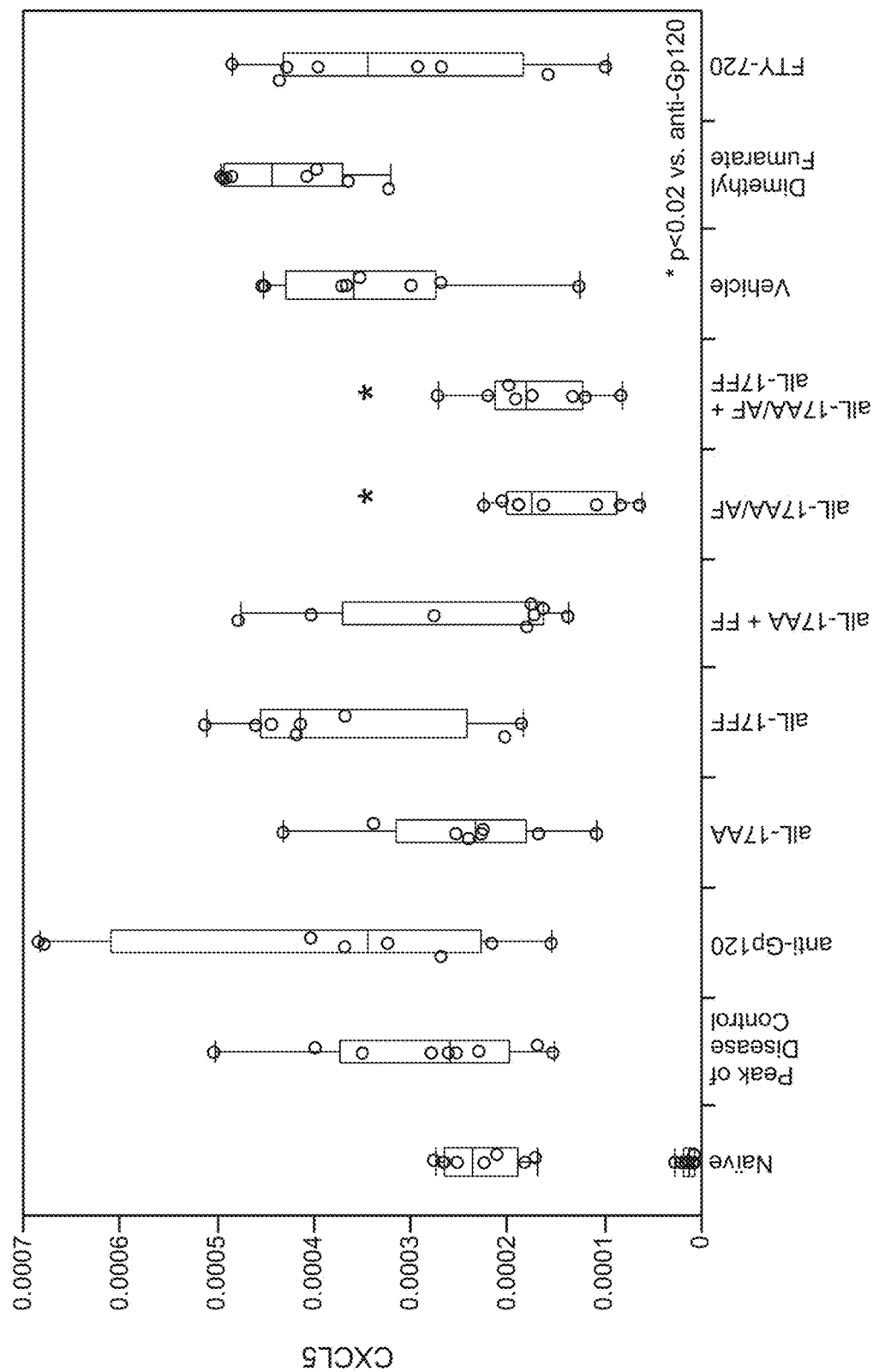
FIG. 13 shows the transcript abundance plot of CXCL5 in an EAE model with various treatments as described in Example 3 below.

FIG. 11A shows a heat map of selected additional genes upregulated in EAE spinal cords at the peak of disease and decrease of the expression of those genes with an anti-IL-17AA/AF+anti-IL-17FF antibody. The goal of the studies was to identify genes not previously identified as being associated with IL-17 or not associated with RRMS or other neurodegenerative diseases. The results in FIG. 11 show that the RNA levels of CHI3L1, TIMP1, IL-6, CXCL1, LRG1, and NFκBIZ were increased at the peak of disease (as compared to pre disease control) and were decreased upon treatment of anti-IL-17AA/AF and anti-IL-17FF antibodies, as compared to control treatment (anti-ragweed and CTLA-4-Ig immunoadhesin). FIGS. 12A-F show the transcript abundance plots of each of these genes with each treatment. FIG. 13 shows that treatments with anti-IL-17 antibodies also reduced the gene expression of CXCL5. Blockage of IL-17 target genes in EAE spinal cords was better achieved in some cases with treatments that included an anti-IL-17AA/AF antibody compared to those with the anti-IL-17AA antibody or anti-IL-FF antibody alone. See FIGS. 12 and 13.

Example 4

RRMS Biomarkers in Human Samples

IL-17A, IL-17F and various target proteins were measured in cerebrospinal fluid (CSF) and serum from 50 RRMS patients and 20 healthy donors (HD) using the Erenna® Immunoassay platform (Singulex, Inc.) or sandwich immunoassays as described in Example 1.

Table 4 below shows protein levels of selected genes that were tested in the human CSF samples, including LRG1, TIMP1, YKL40 (CHI3L1), CXCL1, CXCL10, IL-6, and IL-8. The protein levels of all genes showed a significant elevation in RRMS vs. healthy control (see "Differential level by diagnosis" column in Table 4). With the exception of IL-6, the protein levels of all the genes in Table 4 showed good correlation with the protein levels of IL-17AA in the human RRMS CSF samples (see "Spearman correlation with IL17 CSF" column).

TABLE 4

| | | | Differential level by diagnosis | | Spearman correlation with IL17 CSF | |
| --- | --- | --- | --- | --- | --- | --- |
| | | | Wilcoxon | | (RRMS only) | |
| Biomarker | units | location | p-value | logFC | p-value | rho |
| LRG1 | ng/ml | CSF | 0.07 | 0.45 | 0.1255 | 0.22 |
| TIMP1 | ng/ml | CSF | 0.004 | 0.26 | 0.0005 | 0.48 |
| YKL40 | ng/ml | CSF | 0.01 | 0.42 | 0.6522 | 0.07 |
| CXCL1 | pg/ml | CSF | 0.005 | −0.49 | 0.0428 | 0.29 |
| CXCL10 | pg/ml | CSF | 0.0005 | 1.05 | 0.0262 | 0.31 |
| IL6 | pg/ml | CSF | 0.13 | 0.66 | 0.2437 | −0.17 |
| IL8 | pg/ml | CSF | 0.15 | 0.23 | 0.0042 | 0.40 |

Figure 14:
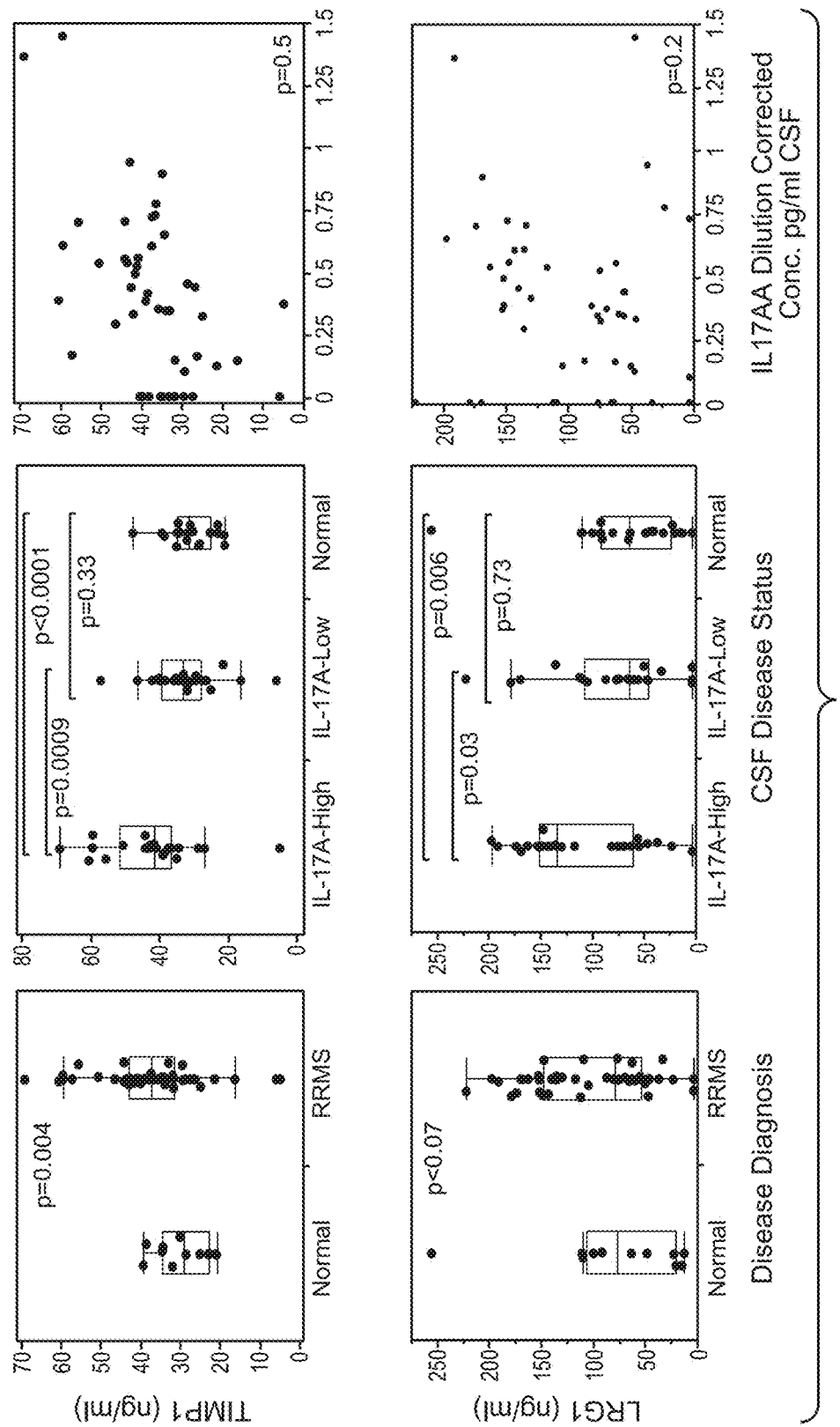
FIG. 14 shows that TIMP1 and LRG1 are elevated in RRMS CSF and correlate with CSF IL-17AA as described in Example 4 below.

In particular, the correlations of TIMP1 and LRG1 with IL-17AA are shown in FIG. 14. FIG. 14 shows that TIMP1 and LRG1 protein levels were elevated in the CSF samples of human RRMS patients, and their protein levels in CSF also correlated with the protein levels of IL-17AA in CSF of human RRMS patients, confirming the results from the mouse EAE model. In addition, the levels of IL17A, TIMP1 and LRG1 in CSF correlated with CSF/serum albumin ratio, a measure of blood-brain barrier permeability. The serum and CSF albumin was measured using a Sigma albumin ELISA kit (Catalog #RAB0603) using the manufacturer's directions. Serum was diluted 1/1,000,000 and CSF was diluted to 1/5,000 for the assay. The results are shown below in Table 5.

TABLE 5

| Variable | by variable | Spearman rho | p-value |
| --- | --- | --- | --- |
| CSF/serum Albumin | IL17AA in CSF | 0.3 | 0.02 |
| CSF/serum Albumin | TIMP1 in CSF | 0.4 | 0.008 |
| CSF/serum Albumin | LRG1 in CSF | 0.6 | <0.0001 |

Example 5

G-CSF as a Serum Marker of RRMS

G-CSF (CSF3) is a cytokine that is regulated by IL-17 in multiple cell lineages and is a key factor for neutrophil proliferation. G-CSF was not detectable in CSF but was detectable in serum. Thus, the correlation of G-CSF serum levels to IL-17AA was investigated in both the EAE model and in human serum samples.

Figure 9:
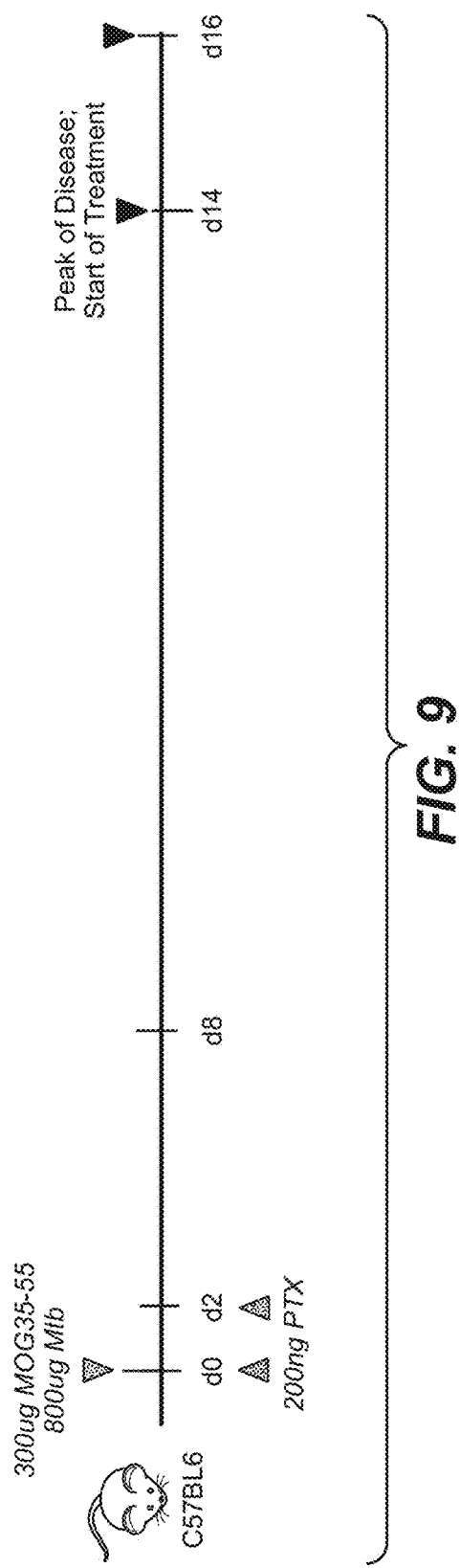
FIG. 9 shows the method used to assess gene expression in the experimental autoimmune encephalomyelitis (EAE) model for MS and the effect of IL-17 antibody on gene expression pathways as described in Example 3 below.

Serum was obtained from the EAE mice described above in Example 3 at the time points indicated and shown in FIG. 9. G-CSF was measured using a sandwich ELISA with monoclonal antibodies specific for G-CSF.

Figure 15:
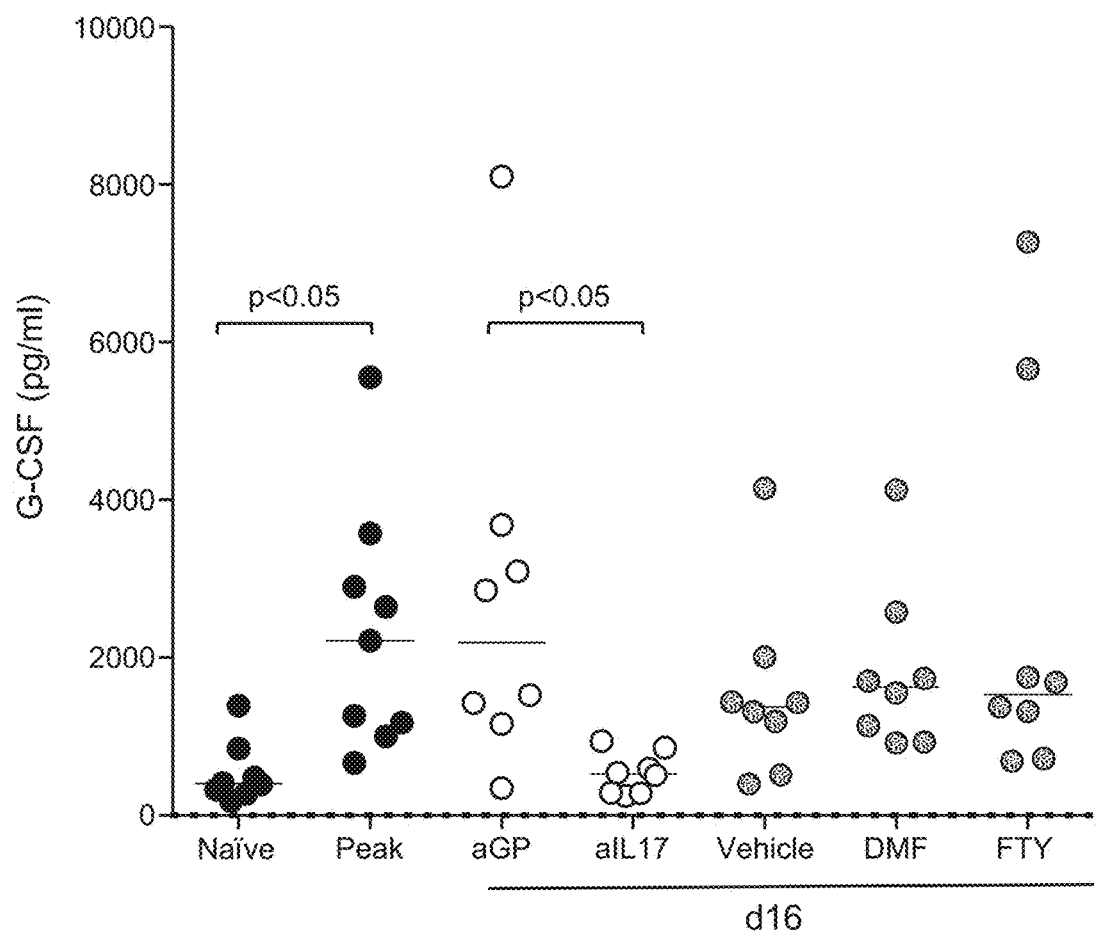
FIG. 15 shows serum G-CSF levels in an EAE model with various treatments as described in Example 5 below.

As shown in FIG. 15, peak levels of G-CSF were observed prior to clinical disease manifestation in the EAE model (at day 8, when clinical scores were 0). The serum G-CSF decreased after treatment with a cocktail of anti-IL-17 antibodies comprising aIL-17AA/AF+aIL-17FF (combination of aIL-17AA/AF and aIL-17FF) described in Table 3 above, but not after treatment with DMF or FTY-720.

Figure 16:
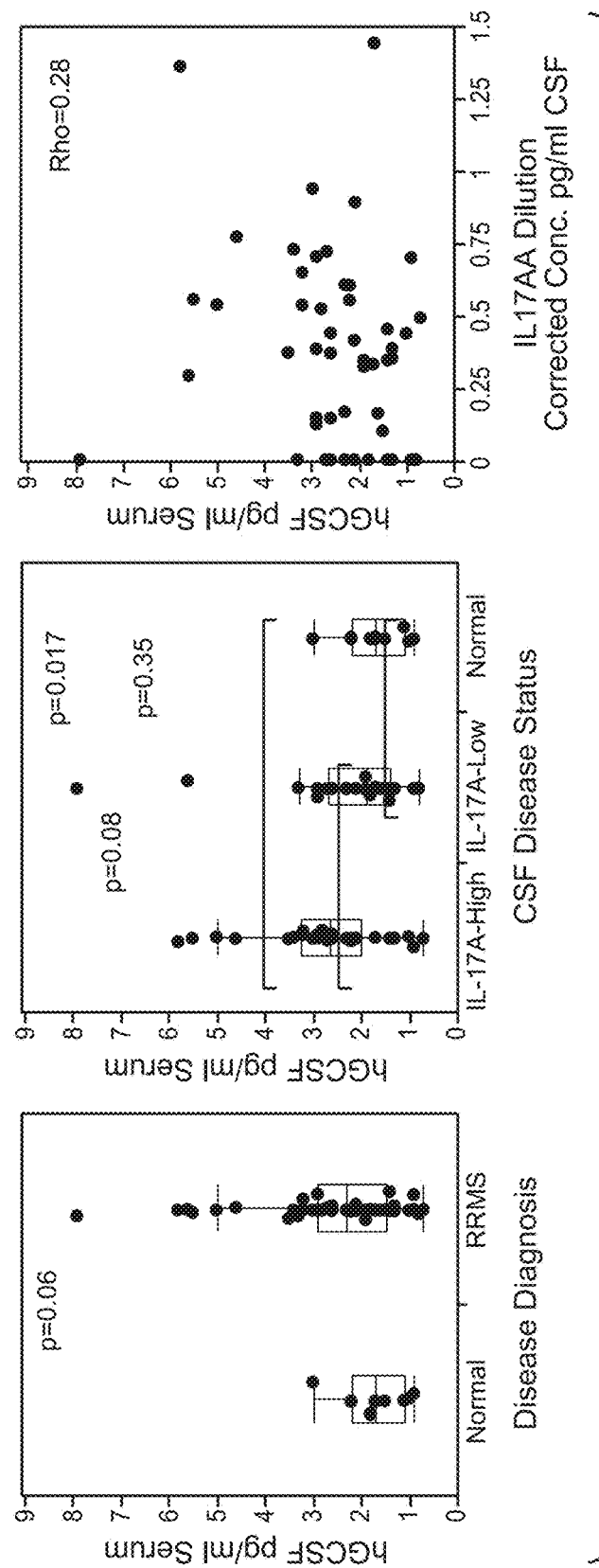
FIG. 16 shows human G-CSF levels in serum from normal and RRMS patients as described in Example 5 below.

In human serum samples, G-CSF was elevated in IL-17AA-high RRMS patients and showed a correlation with CSF IL-17AA levels. See FIG. 16.

Thus, serum G-CSF levels could be used as a serum marker in identifying IL-17AA-high RRMS patients, especially IL-17AA-high RRMS patients that can benefit from the treatment targeting IL-17AA, IL-17FF and/or IL-17AF.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All references cited throughout the specification, and the references cited therein, are hereby expressly incorporated by reference in their entirety.

---

What is claimed is:

1. A method of treating a mammalian subject suffering from multiple sclerosis (MS), comprising:
   a) measuring, in a cerebrospinal fluid (CSF) sample of the subject, an expression level of tissue inhibitor of metalloproteinase 1 (TIMP1);
   b) comparing the expression level measured in a) to a reference expression level of TIMP1 in a CSF sample of an MS-negative control;
   c) identifying the subject as more likely to have an increased expression level of interleukin-17 (IL-17) as compared to an MS-negative control when the expression level measured in a) is above the reference expression level; and
   d) administering an effective amount of an IL-17 antagonist to the subject identified in c),
   wherein the IL-17 antagonist is an anti-IL-17 antibody or an anti-IL-17 receptor antibody.

2. The method of claim 1, wherein the mammalian subject is a human.

3. The method of claim 1, wherein the multiple sclerosis is characterized by an increased expression level of IL-17.

4. The method of claim 3, wherein the expression level of IL-17 is elevated in the CSF of the subject.

5. The method of claim 1, wherein the IL-17 having the increased expression level is IL-17AA.

6. The method of claim 1, wherein the a) comprises measuring the expression level of the RNA transcript or the protein product of TIMP1.

7. The method of claim 1, further comprising:
   measuring, in a biological sample of the subject, an expression level of at least one gene selected from the group consisting of LRG1, CXCL1, CXCL5, CXCL10, IL-8, NFκBIZ, YKL40, and G-CSF;
   comparing the measured expression level of the at least one gene to a reference expression level of the at least one gene of an MS-negative control; and
   administering an effective amount of the IL-17 antagonist to the subject whose expression level of TIMP1 measured in a) and the measured expression level of the at least one gene are above the reference expression level of TIMP1 and the reference expression level of the at least one gene.

8. The method of claim 7, wherein the at least one gene
   i) comprises NFκBIZ;
   ii) is selected from the group consisting of CXCL1, CXCL5, and CXCL10, or
   ii) is selected from the group consisting of LRG1 and G-CSF.

9. The method of claim 1, wherein the IL-17 antagonist is an anti-IL-17 antibody and the anti-IL-17 antibody binds to an IL-17A homodimer, IL-17F homodimer, and/or IL-17AF heterodimer.

10. The method of claim 1, wherein the anti-IL-17 antibody or the anti-IL-17 receptor antibody is selected from the group consisting of brodalumab, secukinumab, ixekizumab, bimekizumab, CNTO 6785, ALX-0761, afasevikumab, and combinations thereof.

11. The method of claim 1, further comprising administering to the subject at least one MS-treating agent selected from the group consisting of dimethyl fumarate, FTY-720, nataluzimab, corticosteroids, β-interferon, glatiramer acetate, teriflunomide, mitoxantrone, anti-CD20 antibody, and combinations thereof.

12. A method of treating a mammalian subject suffering from multiple sclerosis (MS), comprising: administering an interleukin-17 (IL-17) antagonist to a subject who has been identified as more likely to have an increased expression level of IL-17 as compared to an MS-negative control, wherein the identification comprises detecting, in a cerebrospinal fluid (CSF) sample of the subject, an increased expression level of tissue inhibitor of metalloproteinase 1 (TIMP1) relative to a reference expression level of TIMP1 in a CSF sample of an MS-negative control, and wherein the IL-17 antagonist is an anti-IL-17 antibody or an anti-IL-17 receptor antibody.

13. The method of claim 12, wherein the mammalian subject is a human.

14. The method of claim 12, wherein the multiple sclerosis is characterized by an increased expression level of IL-17.

15. The method of claim 12, wherein the identification further comprises detecting, in a biological sample of the subject, an increased expression level of at least one gene selected from the group consisting of LRG1, CXCL1, CXCL5, CXCL10, IL-8, NFκBIZ, YKL40, and G-CSF relative to a reference expression level of the at least one gene of an MS-negative control.

16. The method of claim 15, wherein the biological sample is a biological fluid selected from the group consisting of CSF, serum, plasma, and combinations thereof.

17. The method of claim 12, wherein the anti-IL-17 antibody or the anti-IL-17 receptor antibody is selected from the group consisting of brodalumab, secukinumab, ixekizumab, bimekizumab, CNTO 6785, ALX-0761, afasevikumab, and combinations thereof.

18. The method of claim 12, further comprising administering to the subject at least one MS-treating agent selected from the group consisting of dimethyl fumarate, FTY-720, nataluzimab, corticosteroids, β-interferon, glatiramer acetate, teriflunomide, mitoxantrone, anti-CD20 antibody, and combinations thereof.

\* \* \* \* \*